US012577591B2

(12) United States Patent
Nagarajan et al.

(10) Patent No.: US 12,577,591 B2
(45) Date of Patent: Mar. 17, 2026

(54) MICROORGANISMS AND METHODS FOR INCREASING CO-FACTORS

(71) Applicant: Genomatica, Inc., San Diego, CA (US)

(72) Inventors: Harish Nagarajan, San Diego, CA (US); Gionata Scalcinati, Carlsbad, CA (US); Tae Hoon Yang, Encinitas, CA (US)

(73) Assignee: Genomatica, Inc., San Diego, CA (US)

( * ) Notice: Subject to any disclaimer, the term of this patent is extended or adjusted under 35 U.S.C. 154(b) by 754 days.

(21) Appl. No.: 17/770,233

(22) PCT Filed: Oct. 22, 2020

(86) PCT No.: PCT/US2020/056831
§ 371 (c)(1),
(2) Date: Apr. 19, 2022

(87) PCT Pub. No.: WO2021/081185
PCT Pub. Date: Apr. 29, 2021

(65) Prior Publication Data

US 2022/0403420 A1 Dec. 22, 2022

Related U.S. Application Data

(60) Provisional application No. 62/925,150, filed on Oct. 23, 2019.

(51) Int. Cl.
*C12P 7/18* (2006.01)
*C12N 9/02* (2006.01)
(Continued)

(52) U.S. Cl.
CPC .............. *C12P 7/18* (2013.01); *C12N 9/0006* (2013.01); *C12N 9/0008* (2013.01);
(Continued)

(58) Field of Classification Search
CPC .. C12P 7/18; C12P 7/625; C12P 13/04; C12P 19/36; C12P 7/62; C12N 9/0006;
(Continued)

(56) References Cited

U.S. PATENT DOCUMENTS 4,278,765 A 7/1981 Debabov et al.
6,180,373 B1 1/2001 Which et al.
(Continued)

FOREIGN PATENT DOCUMENTS

WO WO 2002/055995 A2 7/2002
WO WO 2003/106998 A1 12/2003
(Continued)

OTHER PUBLICATIONS

Sadowski MI, Jones DT. The sequence-structure relationship and protein function prediction. Curr Opin Struct Biol. Jun. 2009;19(3):357-62. doi: 10.1016/j.sbi.2009.03.008. Epub May 4, 2009. PMID: 19406632. (Year: 2009).*
(Continued)

*Primary Examiner* — Robert B Mondesi
(74) *Attorney, Agent, or Firm* — Greenberg Traurig, LLP

(57) ABSTRACT

The present disclosure provides microbial organisms having increased availability of co-factors, such as NADPH, for increasing production of various products, including 1,3-BDO, MMA, (3R)-hydroxybutyl (3R)-hydroxybutyrate, amino acids, 3HB-CoA, adipate, caprolactam, 6-ACA, HMD A, or MAA, and products made from any of these. Also provided are one or more exogenous nucleic acids encoding an enzyme expressed in a sufficient amount to increase availability of NADPH, where the exogenous nucleic acid includes one or more of ATP-NADH kinase, pntAB, nadK, and gapN. Also provided are one or more gene attenuations occurring in genes, such as NDH-2, that result in an increased ratio of NADPH to NADH. Various
(Continued)

combinations of the exogenous nucleic acids and gene deletions are also provided in the present disclosure. The present disclosure also provides methods of making and using the same, including methods for culturing cells, and for the production of the various products.

25 Claims, 17 Drawing Sheets

(51) Int. Cl.
*C12N 9/04* (2006.01)
*C12N 9/12* (2006.01)

(52) U.S. Cl.
CPC ......... *C12N 9/0036* (2013.01); *C12N 9/1205* (2013.01); *C12Y 101/01036* (2013.01); *C12Y 102/01009* (2013.01); *C12Y 106/01002* (2013.01); *C12Y 207/01023* (2013.01)

(58) Field of Classification Search
CPC .. C12N 9/0008; C12N 9/0036; C12N 9/1205; C12N 15/52; C12Y 101/01036; C12Y 102/01009; C12Y 106/01002; C12Y 207/01023
USPC .......... 435/158
See application file for complete search history.

(56) References Cited

U.S. PATENT DOCUMENTS

| | | | | |
|---|---|---|---|---|
| 7,127,379 | B2 | 10/2006 | Palsson et al. | |
| 8,048,651 | B2 | 11/2011 | Zelder et al. | |
| 9,133,487 | B2 | 9/2015 | Burk et al. | |
| 9,346,902 | B2 | 5/2016 | Burgard et al. | |
| 2002/0012939 | A1 | 1/2002 | Palsson | |
| 2002/0168654 | A1 | 11/2002 | Maranas et al. | |
| 2003/0059792 | A1 | 3/2003 | Palsson et al. | |
| 2003/0224363 | A1 | 12/2003 | Park et al. | |
| 2003/0233218 | A1 | 12/2003 | Schilling et al. | |
| 2004/0009466 | A1 | 1/2004 | Maranas et al. | |
| 2004/0029149 | A1 | 2/2004 | Palsson et al. | |
| 2004/0072723 | A1 | 4/2004 | Palsson et al. | |
| 2008/0293101 | A1* | 11/2008 | Peters .................. | C12N 9/0036 435/157 |
| 2009/0047719 | A1 | 2/2009 | Burgard et al. | |
| 2012/0190089 | A1 | 7/2012 | Buelter et al. | |
| 2013/0065279 | A1 | 3/2013 | Burk et al. | |
| 2014/0024087 | A1 | 1/2014 | Lee et al. | |
| 2015/0147788 | A1 | 5/2015 | Lee et al. | |
| 2016/0108442 | A1 | 4/2016 | Adelstein et al. | |
| 2016/0326553 | A1 | 11/2016 | Burgard et al. | |
| 2017/0145446 | A1* | 5/2017 | Aliprandi ............. | C12N 9/0006 |

FOREIGN PATENT DOCUMENTS

| | | | | |
|---|---|---|---|---|
| WO | WO-2009144245 A1 * | 12/2009 | ............. | C12P 21/02 |
| WO | WO 2012/177721 A1 | 12/2012 | | |

OTHER PUBLICATIONS

Seffernick JL, de Souza ML, Sadowsky MJ, Wackett LP. Melamine deaminase and atrazine chlorohydrolase: 98 percent identical but functionally different. J Bacteriol. Apr. 2001;183(8):2405-10. doi: 10.1128/JB.183.8.2405-2410.2001. PMID: 11274097; PMCID: PMC95154. (Year: 2001).*

Tang S, Edwards EA. Identification of Dehalobacter reductive dehalogenases that catalyse dechlorination of chloroform, 1,1,1-trichloroethane and 1,1-dichloroethane. Philos Trans R Soc Lond B Biol Sci. Mar. 11, 2013;368(1616):20120318. doi: 10.1098/rstb.2012.0318. PMID: 23479748; PMCID: PMC3638459. (Year: 2013).*

Witkowski A, Joshi AK, Lindqvist Y, Smith S. Conversion of a beta-ketoacyl synthase to a malonyl decarboxylase by replacement of the active-site cysteine with glutamine. Biochemistry. Sep. 7, 1999;38(36):11643-50. doi: 10.1021/bi990993h. PMID: 10512619. (Year: 1999).*

Sousa S et al. The ARO4 gene of Candida albicans encodes a tyrosine-sensitive DAHP synthase: evolution, functional conservation and phenotype of Aro3p-, Aro4p-deficient mutants. Microbiology (Reading). May 2002;148(Pt 5):1291-1303. doi: 10.1099/00221287-148-5-1291. PMID: 11988503 (Year: 2002).*

Bergquist et al., "Degenerate oligonucleotide gene shuffling (DOGS) and random drift mutagenesis (RNDM): two complementary techniques for enzyme evolution," *Biomol. Eng.*, 22(1-3):63-72 (2005).

Bergquist et al., "Degenerate oligonucleotide gene shuffling," *Methods Mol. Biol.*, 352:191-204 (2007).

Burgard et al., "Minimal reaction sets for *Escherichia coli* metabolism under different growth requirements and uptake environments," *Biotechnol. Prog.* 17(5):791-797 (2001).

Burgard et al., "Optknock: a bilevel programming framework for identifying gene knockout strategies for microbial strain optimization," *Biotechnol. Bioeng.*, 84(6):647-657 (2003).

Coco et al., "DNA shuffling method for generating highly recombined genes and evolved enzymes," *Nat. Biotechnol.*, 19(4):354-359 (2001).

Fujii et al., "Error-prone rolling circle amplification: the simplest random mutagenesis protocol," *Nat. Protoc.*, 1(5):2493-2497 (2006).

Fujii et al., "One-step random mutagenesis by error-prone rolling circle amplification," *Nucleic Acids Res.*, 32(19):e145 (2004).

Gibbs et al., "Degenerate oligonucleotide gene shuffling (DOGS): a method for enhancing the frequency of recombination with family shuffling," *Gene*, 271(1):13-20 (2001).

Hayes et al., "Combining computational and experimental screening for rapid optimization of protein properties," *Proc. Natl. Acad. Sci. USA*, 99(25):15926-15931 (2002).

Hibbert et al., "Directed evolution of biocatalytic processes," *Biomol. Eng.*, 22(1-3):11-19 (2005).

Hoffmeister et al., "Mitochondrial trans-2-enoyl-CoA reductase of wax ester fermentation from Euglena gracilis defines a new family of enzymes involved in lipid synthesis," *J. Biol. Chem.*, 280(6):4329-4338 (2005).

Huisman et al., "Enzyme Evoluation for Chemical Process Applications," *Biocatalysis in the Pharmaceutical and Biotechnology Industries*, Patel ed., CRC Press, Boca Raton, FL, pp. 717-742 (2007).

Ichikawa et al., "Catalytic reaction of 1,3-butanediol over solid acids," *J. Mol. Catalysis A-Chemical*, 256:106-112 (2006).

Ichikawa et al., "PIO study on 1, 3-butanediol dehydration over CeO2 (1 1 1) surface," *J. Mol. Catalysis A-Chemical*, 231:181-189 (2005).

Kretz et al., "Gene site saturation mutagenesis: a comprehensive mutagenesis approach," *Methods Enzymol.*, 388:3-11 (2004).

Lee et al., "A new approach to directed gene evolution by recombined extension on truncated templates (RETT)," *J. Molec. Catalysis*, 26:119-129 (2003).

Lin et al., "Fed-batch culture of a metabolically engineered *Escherichia coli* strain designed for high-level succinate production and yield under aerobic conditions," *Biotechnol. Bioeng.*, 90(6):775-779 (2005).

Low et al., "Mimicking somatic hypermutation: affinity maturation of antibodies displayed on bacteriophage using a bacterial mutator strain," *J. Mol. Biol.*, 260(3):359-368 (1996).

Lutz et al., "Creating multiple-crossover DNA libraries independent of sequence identity," *Proc. Natl. Acad. Sci. USA*, 98(20):11248-11253 (2001).

Lutz et al., "Rapid generation of incremental truncation libraries for protein engineering using alpha-phosphothioate nucleotides," *Nucleic Acids Res.*, 29(4):E16 (2001).

Mori et al., "Molecular Conversion of NAD Kinase to NADH Kinase Through Single Amino Acid Residue Substitution," *J. Biol. Chem.*, 280(25):24104-24112 (2005).

Muller et al., "Nucleotide exchange and excision technology (NExT) DNA shuffling: a robust method for DNA fragmentation and directed evolution," *Nucleic Acids Res.*, 33(13):e117 (2005).

(56) References Cited

OTHER PUBLICATIONS

Ness et al., "Synthetic shuffling expands functional protein diversity by allowing amino acids to recombine independently," *Nat. Biotechnol.*, 20(12):1251-1255 (2002).
Ostermeier et al., "A combinatorial approach to hybrid enzymes independent of DNA homology," *Nat. Biotechnol.*, 17(12):1205-1209 (1999).
Ostermeier et al., "Combinatorial protein engineering by incremental truncation," *Proc. Natl. Acad. Sci. USA*, 96(7):3562-3567 (1999).
Otten et al., "Directed evolution: selecting today's biocatalysts," *Biomol. Eng.*, 22(1-3):1-9 (2005).
Pritchard et al., "A general model of error-prone PCR," *J. Theor. Biol.*, 234(4):497-509 (2005).
Rajpal et al., "A general method for greatly improving the affinity of antibodies by using combinatorial libraries," *Proc. Natl. Acad. Sci. USA*, 102(24):8466-8471 (2005).
Reetz et al., "Directed Evolution of an Enantioselective Enzyme through Combinatorial Multiple-Cassette Mutagenesis," *Angew. Chem. Int. Ed. Engl.*, 40(19):3589-3591 (2001).
Reetz et al., "Iterative saturation mutagenesis (ISM) for rapid directed evolution of functional enzymes," *Nat. Protoc.*, 2(4):891-903 (2007).
Reetz et al., "Iterative saturation mutagenesis on the basis of B factors as a strategy for increasing protein thermostability," *Angew. Chem. Int. Ed. Engl.*, 45(46):7745-7751 (2006).
Reidhaar-Olson et al., "Combinatorial cassette mutagenesis as a probe of the informational content of protein sequences," *Science*, 241(4861):53-57 (1988).
Reidhaar-Olson et al.,"Random mutagenesis of protein sequences using oligonucleotide cassettes," *Methods Enzymol.*, 208:564-586 (1991).
Selifonova et al., "Rapid evolution of novel traits in microorganisms," *Appl. Environ. Microbiol.*, 67(8):3645-3649 (2001).
Sen et al., "Developments in directed evolution for improving enzyme functions," *Appl. Biochem. Biotechnol.*, 143(3):212-223 (2007).
Shao et al., "Random-priming in vitro recombination: an effective tool for directed evolution," *Nucleic Acids Res.*, 26(2):681-683 (1998).
Sieber et al., "Libraries of hybrid proteins from distantly related sequences," *Nat. Biotechnol.*, 19(5):456-460 (2001).
Spaans et al., "NADPH-generating systems in bacteria and archaea," *Front. Microbiol.*, 6:1-27 (2015).
Stemmer, "DNA shuffling by random fragmentation and reassembly: in vitro recombination for molecular evolution," *Proc. Natl. Acad. Sci. USA*, 91(22):10747-10751 (1994).
Stemmer, "Rapid evolution of a protein in vitro by DNA shuffling," *Nature*, 370(6488):389-391 (1994).
Umbarger, "Amino acid biosynthesis and its regulation," *Ann. Rev. Biochem.*, 47: 533-606 (1978).
Volkov et al., "Recombination and chimeragenesis by in vitro heteroduplex formation and in vivo repair," *Nucleic Acids Res.*, 27(18):e18 (1999).
Volkov et al., "Random chimeragenesis by heteroduplex recombination," *Methods Enzymol.*, 328:456-463 (2000).
Wong et al., "Sequence saturation mutagenesis (SeSaM): a novel method for directed evolution," *Nucleic Acids Res.*, 32(3):e26 (2004).
Wong et al., "Sequence saturation mutagenesis with tunable mutation frequencies," *Anal. Biochem.*, 341(1):187-189 (2005).
Wong et al., "Transversion-enriched sequence saturation mutagenesis (SeSaM-Tv+): a random mutagenesis method with consecutive nucleotide exchanges that complements the bias of error-prone PCR," *Biotechnol. J.*, 3(1):74-82 (2008).
Zhao et al., "Molecular evolution by staggered extension process (StEP) in vitro recombination," *Nat. Biotechnol.*, 16(3):258-261 (1998).

* cited by examiner

L16933 – med
L16933 – high
L17786 – med
L17786 – high

MICROORGANISMS AND METHODS FOR INCREASING CO-FACTORS

CROSS-REFERENCE TO RELATED APPLICATIONS

This application is a U.S. National Stage Application under 35 U.S.C. § 371 of International Patent Application No. PCT/US2020/056831, filed Oct. 22, 2020, which claims the benefit of priority of U.S. Provisional Application No. 62/925,150, filed Oct. 23, 2019, each of which is incorporated by reference herein in its entirety.

FIELD

The present invention relates generally to organisms engineered to produce desired products, engineered enzymes that facilitate production of a desired product, and more specifically to non-naturally occurring organisms that can increase the availability of co-factors, such as NADPH, for increasing production of desired products, such as 1,3-butanediol, methyl methacrylate, (3R)-hydroxybutyl (3R)-hydroxybutyrate, amino acids, and related products and products derived therefrom.

BACKGROUND

Microbial organisms can be used for the production of chemical compounds, such as 1,3-butanediol (1,3-BDO), methyl methacrylate (MMA), (3R)-hydroxybutyl (3R)-hydroxybutyrate, and amino acids. The titer, rate, and yield of such production can be limited by co-factor availability. In particular, limited cofactors, such as the reducing agent reduced nicotinamide adenine dinucleotide phosphate (NADPH), can result in limited redox availability. For example, NADPH provides the reducing equivalents for biosynthetic reactions, such as lipid and nucleic acid synthesis, and the oxidation-reduction involved in protecting against the toxicity of reactive oxygen species (ROS). NADPH is also used for anabolic pathways, such as cholesterol synthesis and fatty acid chain elongation. An imbalance in redox levels can lead to deleterious effects on the production of chemical compounds, such as 1,3-butanediol (1,3-BDO), methyl methacrylate (MMA), (3R)-hydroxybutyl (3R)-hydroxybutyrate, and amino acids. Accordingly, increased availability of co-factors, such as NADPH, can help to increase the titer, rate, and yield of chemical compounds, such as 1,3-butanediol (1,3-BDO), methyl methacrylate (MMA), (3R)-hydroxybutyl (3R)-hydroxybutyrate, and amino acids.

1,3-BDO is a four carbon diol traditionally produced from acetylene via its hydration. The resulting acetaldehyde is then converted to 3-hydroxybutyraldehyde which is subsequently reduced to form 1,3-BDO. More recently, acetylene has been replaced by the less expensive ethylene as a source of acetaldehyde. 1,3-BDO is commonly used as an organic solvent for food flavoring agents. It is also used as a co-monomer for polyurethane and polyester resins and is widely employed as a hypoglycemic agent. Optically active 1,3-BDO is a useful starting material for the synthesis of biologically active compounds and liquid crystals. Another use of 1,3-butanediol is that its dehydration affords 1,3-butadiene (Ichikawa et al. Journal of Molecular Catalysis A-Chemical 256:106-112 (2006); Ichikawa et al. Journal of Molecular Catalysis A-Chemical 231:181-189 (2005), which is useful in the manufacture synthetic rubbers (e.g., tires), latex, and resins. The reliance on petroleum based feedstocks for either acetylene or ethylene warrants the development of a renewable feedstock based route to 1,3-butanediol and to butadiene.

MMA is an organic compound with the formula $CH_2{=}C(CH_3)CO_2CH_3$. This colorless liquid is the methyl ester of methacrylic acid (MMA) and is the monomer for the production of the transparent plastic polymethyl methacrylate (PMMA). The principal application of methyl methacrylate is the production of polymethyl methacrylate acrylic plastics. Also, methyl methacrylate is used for the production of the co-polymer methyl methacrylate-butadiene-styrene (MBS), used as a modifier for PVC. Methyl methacrylate polymers and co-polymers are used for waterborne coatings, such as latex paint. Uses are also found in adhesive formulations. Contemporary applications include the use in plates that keep light spread evenly across liquid crystal display (LCD) computer and TV screens. Methyl methacrylate is also used to prepare corrosion casts of anatomical organs, such as coronary arteries of the heart.

The intake of compounds and compositions containing (R)-3-hydroxybutyrate derivatives, e.g. (3R)-hydroxybutyl (3R)-hydroxybutyrate, have been shown to boost the levels of ketone bodies in the blood. Ketone bodies are chemical compounds which are produced when fatty acids are metabolized by the body for energy, which can in turn lead to the ketone bodies themselves being used for energy. Ketone bodies have been shown as being suitable for reducing the levels of free fatty acids circulating in the plasma of an individual. Ingestion of ketone bodies can also lead to various clinical benefits, including an enhancement of physical and cognitive performance and treatment of cardiovascular conditions, diabetes and treatment of mitochondrial dysfunction disorders and in treating muscle fatigue and impairment. However, direct administration of ketone bodies is impractical and dangerous. For example, direct administration of either (R)-3-hydroxybutyrate can result in significant acidosis following rapid absorption from the gastrointestinal tract. Administration of the sodium salt of these compounds is also unsuitable due to a potentially dangerous sodium overload that would accompany administration of therapeutically relevant amounts of these compounds. Administration of (R)-3-hydroxybutyrate derivatives in oligomeric form has been used to circumvent this problem. To gain desirable therapeutic and other benefits, the ketone body generally needs to be present in the blood plasma of an individual at a threshold level, for example at least 1 mM (3R)-hydroxybutyl (3R)-hydroxybutyrate. However, low yields, or impracticability on a large scale have hindered production.

Amino acids are attractive and promising biochemicals with market capacity requirements constantly increasing. The amino acids market is expected to grow from $10.3 billion in 2019 to $13.4 billion by 2024, with a growth rate of 5.3% for the period of 2019-2024 (see, e.g, Elder, M. 2019, World Markets for Fermentation Ingredients, BCC Research Report Overview). Amino acids are used in many industrial applications such as in pharmaceuticals, food additives, feed supplements, cosmetics, polymer materials, medical products, and agricultural chemicals. Fermentation of microorganisms, such as *Corynebacterium glutamicum* or *Escherichia coli*, play a significant role in the industrial production of amino acids. However, the industrial processes to produce amino acids still need to be optimized and find more cost-effective and sustainable routes to produce amino acids.

Thus, there exists a need for the development of methods to increase the availability of co-factors, such as NADPH, for effectively producing commercial quantities of compounds such as 1,3-butanediol, methyl methacrylate (MMA), ketone ester 3R-hydroxybutyric acid-3R-hydroxybutryrate, as well as amino acids. The present invention satisfies these needs and provides related advantages as well. Additional product molecules that can be produced by the teachings of this invention include but are not limited to adipate, caprolactam, 6-aminocaproic acid (6-ACA), hexamethylenediamine (HMPA), or methacrylic acid (MAA).

SUMMARY OF INVENTION

In some aspects, the present disclosure provides a non-naturally occurring microbial organism having an increased availability of reduced nicotinamide adenine dinucleotide phosphate (NADPH). In some embodiments, the microbial organism having increased availability of NADPH includes (a) one or more exogenous nucleic acids encoding an enzyme expressed in a sufficient amount to increase availability of NADPH, (b) one or more gene attenuations occurring in genes encoding proteins or enzymes that result in an increased ratio of NADPH to NADH present in the cytosol of said non-naturally occurring microbial organism following said disruptions, or (c) a combination of one or more exogenous nucleic acids encoding an enzyme expressed in a sufficient amount to increase availability of NADPH, and one or more gene attenuations occurring in genes encoding proteins or enzymes that result in an increased ratio of NADPH to NADH present in the cytosol of said non-naturally occurring microbial organism following said disruptions. In certain embodiments, the at least one exogenous nucleic acid is selected from: (i) ATP-NADH kinase, NAD(P) transhydrogenase subunit alpha part 2 (pntAB); (ii) ATP-NAD+kinase (nadK), or (iii) NADP-dependent glyceraldehyde-3-phosphate dehydrogenase (gapN). In certain embodiments, the ATP-NADH kinase is a variant ATP-NAD+kinase.

In some embodiments, the non-naturally occurring microbial organism having an increased availability of NADPH includes one exogenous nucleic acid. In some embodiments, the one exogenous nucleic acid encodes an ATP-NADH kinase. In other embodiments, the exogenous nucleic acid encodes a gapN. In certain embodiments, the ATP-NADH kinase is a variant ATP-NAD+kinase.

In some embodiments, the non-naturally occurring microbial organism having an increased availability of NADPH includes two exogenous nucleic acids. In some embodiments, the two exogenous nucleic acid encode a pntAB and a nadK. In other embodiments, the two exogenous nucleic acid encode an ATP-NADH kinase and a gapN. In certain embodiments, the ATP-NADH kinase is a variant ATP-NAD+kinase.

In some embodiments, the non-naturally occurring microbial organism having an increased availability of NADPH includes three exogenous nucleic acids. In some embodiments, the three exogenous nucleic acids encode an ATP-NADH kinase, a pntAB and a nadK. In some embodiments, the three exogenous nucleic acids encode a gapN, a pntAB and a nadK. In certain embodiments, the ATP-NADH kinase is a variant ATP-NAD+kinase.

In some embodiments, the non-naturally occurring microbial organism having an increased availability of NADPH includes four exogenous nucleic acids. In some embodiments, the four exogenous nucleic acids encode a gapN, an ATP-NADH kinase, a pntAB, and a nadK. In certain embodiments, the ATP-NADH kinase is a variant ATP-NAD+kinase.

In some embodiments, the non-naturally occurring microbial organism having an increased availability of NADPH has an increased ratio of NADPH/NADP.

In some embodiments, the non-naturally occurring microbial organism having an increased availability of NADPH and an exogenous nucleic acid encoding a gapN has a gapN that is expressed at a higher level than an endogenous glyceraldehyde-3-phosphate dehydrogenase A (gapA). In some embodiment, the ratio of the gapN to an endogenous gapA plus said gapN [gapN/(gapN+gap A)] is at least about 10% to about 90%. In some embodiments, the endogenous gapA comprises an attenuated gapA. In some embodiments, the attenuated gapA comprises reduced expression of gapA. In some embodiments, gapN increases production of NADPH. In certain embodiments, the gapN is from a methanotrophic bacteria. In specific embodiments, the gapN is from *Bacillus methanolicus.*

In some embodiments, the non-naturally occurring microbial organism having an increased availability of NADPH with one of more gene attenuations includes a gene attenuation in a gene encoding non-proton-translocating NADH dehydrogenase II (NDH-2). In some embodiments, the gene attenuation in a gene encoding NDH-2 comprises a deletion of NDH-2. In some embodiments, the attenuation of NDH-2 decreases NADPH consumption.

In some embodiments, the non-naturally occurring microbial organism having an increased availability of NADPH with an exogenous nucleic acid encoding an enzyme, the exogenous nucleic acid is regulated by a promoter selected from the group consisting of an endogenous promoter, a constitutive promoter, and an inducible promoter.

In some embodiments, the non-naturally occurring microbial organism having an increased availability of NADPH further includes a 1,3-butanediol (1,3-BDO) pathway, a methyl methacrylate (MMA) pathway, a (3R)-hydroxybutyl (3R)-hydroxybutyrate pathway, an amino acid production pathway, a 3-hydroxybutyryl-coenzyme A (3HB-CoA), an adipate pathway, a caprolactam pathway, a 6-aminocaproic acid (6-ACA) pathway, a hexametheylenediamine (HMDA) pathway, or a methacrylic acid (MAA) pathway.

In some embodiments, the non-naturally occurring microbial organism comprises an 1,3-BDO pathway. In specific embodiments, the 1,3-BDO pathway comprises an acetoacetyl-CoA reductase (CoA-dependent, aldehyde forming); a 3-oxobutyraldehyde reductase (ketone reducing); a 3-hydroxybutyraldehyde reductase; an acetoacetyl-CoA reductase (CoA-dependent, alcohol forming); a 3-oxobutyraldehyde reductase (aldehyde reducing); a 4-hydroxy, 2-butanone reductase; an acetoacetyl-CoA reductase (ketone reducing); a 3-hydroxybutyryl-CoA reductase (aldehyde forming); and a 3-hydroxybutyryl-CoA reductase (alcohol forming). In some embodiments, the microbial organism comprises a nucleic acid encoding an acetoacetyl-CoA reductase (phaB). In specific embodiments, the acetoacetyl-CoA reductase is a mutant acetoacetyl-CoA reductase. In some embodiments, the mutant acetoacetyl-CoA reductase uses NADH as a substrate.

In some embodiments, the non-naturally occurring microbial organism comprises an (3R)-hydroxybutyl (3R)-hydroxybutyrate pathway. In specific embodiments, the (3R)-hydroxybutyl (3R)-hydroxybutyrate pathway comprises a (3R)-hydroxybutyl (3R)-hydroxybutyrate ester forming enzyme; a (3R)-hydroxybutyryl-CoA:(R)-1,3-butanediol alcohol transferase; a (3R)hydroxybutyl 3-oxobutyrate ester forming enzyme; an acetoacetyl-CoA:(R)-1,3-butanediol alcohol transferase; a (3R)-hydroxybutyl 3-oxobutyrate reductase; a (3R)-hydroxybutyryl-ACP:(R)-1,3-butanediol ester synthase, and an acetoacetyl-ACP:(R)-1,3-butanediol ester synthase. In some embodiments, the microbial organism comprises a nucleic acid encoding an acetoacetyl-CoA reductase (phaB). In specific embodiments, the acetoacetyl-CoA reductase is a mutant acetoacetyl-CoA reductase. In some embodiments, the mutant acetoacetyl-CoA reductase uses NADH as a substrate.

In some embodiments, the non-naturally occurring microbial organism comprises a 3HB-CoA pathway. In specific embodiments, the 3HB-CoA pathway comprises an acetyl-CoA thiolase, and a 3-hydroxybutyryl-CoA dehydrogenase.

In some embodiments, the non-naturally occurring microbial organism comprises a MMA pathway. In some embodiments, the MMA pathway comprises: (a) a 4-hydroxybutyryl-CoA dehydratase, a crotonase, a 2-hydroxyisobutyryl-CoA mutase, a 2-hydroxyisobutyryl-CoA dehydratase, and a methacrylic acid (MAA)-CoA: methanol transferase; or (b) a 4-hydroxybutyryl-CoA dehydratase, a crotonase, a 2-hydroxyisobutyryl-CoA mutase, a 3-hydroxyisobutyryl-CoA: methanol transferase, and a methyl-2-hydroxyisobutyrate dehydratase. In some embodiments, the microbial organism further comprises a second MMA pathway comprising: (c) a methacrylic acid (MAA)-CoA: methanol transferase, a 4-hydroxybutyryl-CoA mutase, and a 3-hydroxyisobutyryl-CoA dehydratase; or (d) a 4-hydroxybutyryl-CoA mutase, a 3-hydroxyisobutyryl-CoA: methanol transferase, and a methyl-3-hydroxyisobutyrate dehydratase.

In some embodiments, the non-naturally occurring microbial organism comprises an amino acid production pathway. In specific embodiments, the amino acid production pathway comprises a tryptophan production pathway, a threonine production pathway, a lysine production pathway, or a glutamate production pathway.

In some embodiments, the non-naturally occurring microbial organism comprises a 6-ACA pathway. In specific embodiments, the 6-ACA pathway comprises a 2-amino-7-oxosubarate keto-acid decarboxylase, a 2-amino-7-oxoheptanoate decarboxylase, a 2-amino-7-oxoheptanoate oxidoreductase, a 2-aminopimelate decarboxylase, a 6-aminohexanal oxidoreductase, a 2-amino-7-oxoheptanoate decarboxylase, or a 2-amino-7-oxosubarate amino acid decarboxylase.

In some embodiments, the non-naturally occurring microbial organism comprises a caprolactam pathway. In specific embodiments, the caprolactam pathway comprises 3-oxoadipyl-CoA thiolase, 3-oxoadipyl-CoA reductase, 3-hydroxyadipyl-CoA dehydratase, 5-carboxy-2-pentenoyl-CoA reductase, adipyl-CoA reductase (aldehyde forming), 6-aminocaproate transaminase, 6-aminocaproate dehydrogenase, 6-aminocaproyl-CoA/acyl-CoA transferase, and 6-aminocaproyl-CoA synthase.

In some embodiments, the non-naturally occurring microbial organism comprises an adipate pathway. In specific embodiments, the adipate pathway comprises 3-oxoadipyl-CoA thiolase, 3-oxoadipyl-CoA reductase, 3-hydroxyadipyl-CoA dehydratase, 5-carboxy-2-pentenoyl-CoA reductase, adipyl-CoA hydrolase, adipyl-CoA ligase, adipyl-CoA transferase and phosphotransadipylase/adipate kinase.

In some embodiments, the non-naturally occurring microbial organism comprises a HMDA pathway. In specific embodiments, the HMDA pathway comprise 3-oxoadipyl-CoA thiolase, 3-oxoadipyl-CoA reductase, 3-hydroxyadipyl-CoA dehydratase, 5-carboxy-2-pentenoyl-CoA reductase, adipyl-CoA reductase (aldehyde forming), 6-aminocaproate transaminase, 6-aminocaproate dehydrogenase, 6-aminocaproyl-CoA/acyl-CoA transferase, 6-aminocaproyl-CoA synthase, 6-aminocaproyl-CoA reductase (aldehyde forming), HMDA transaminase, and HMDA dehydrogenase.

In some embodiments, the non-naturally occurring microbial organism comprises a MAA pathway. In specific embodiments, the MAA pathway comprises: (a) (i) a succinyl-CoA transferase, ligase, or synthetase; (ii) a methylmalonyl-CoA mutase; (iii) a methylmalonyl-CoA epimerase; (iv) a methylmalonyl-CoA reductase (aldehyde forming); (v) a methylmalonate semialdehyde reductase; and (vi) a 3-hydroxyisobutyrate dehydratase; (ii) (i) a succinyl-CoA transferase, ligase, or synthetase; (ii) a methylmalonyl-CoA mutase; (iii) a methylmalonyl-CoA reductase (aldehyde forming); (iv) a methylmalonate semialdehyde reductase; and (v) a 3-hydroxyisobutyrate dehydratase; or (iii) (i) a succinyl-CoA transferase, ligase, or synthetase; (ii) a methylmalonyl-CoA mutase; (iii) a methylmalonyl-CoA reductase (alcohol forming); and (iv) a 3-hydroxyisobutyrate dehydratase.

In some embodiments, the microbial organism is a species of bacteria, yeast, or fungus.

In some embodiments, the non-naturally occurring microbial organism is in a substantially anaerobic culture medium.

In another aspect, provided herein is a method for increasing the availability of NADPH in a non-naturally occurring microbial organism, comprising culturing any of the non-naturally occurring microbial organisms provided herein under conditions and for a sufficient period of time to increase the availability of NADPH. In some embodiments, increasing the availability of NADPH yields an increase in one or more compounds selected from the group consisting of 1,3-BDO, MMA, (3R)-hydroxybutyl (3R)-hydroxybutyrate, amino acids, 3HB-CoA, adipate, caprolactam, 6-ACA, HMDA, and MAA.

In yet another aspect, provided herein is a method for increasing the availability of NADPH in a non-naturally occurring microbial organism thereby increasing the yield of one or more compounds selected from the group consisting of 1,3-BDO, MMA, (3R)-hydroxybutyl (3R)-hydroxybutyrate, amino acids, 3HB-CoA, adipate, caprolactam, 6-ACA, HMDA, and MAA via carbohydrate-based carbon feedstock, the method comprising culturing any of the non-naturally occurring microbial organisms provided herein under conditions and for a sufficient period of time to produce a product.

DETAILED DESCRIPTION OF THE INVENTION

Figure 1:
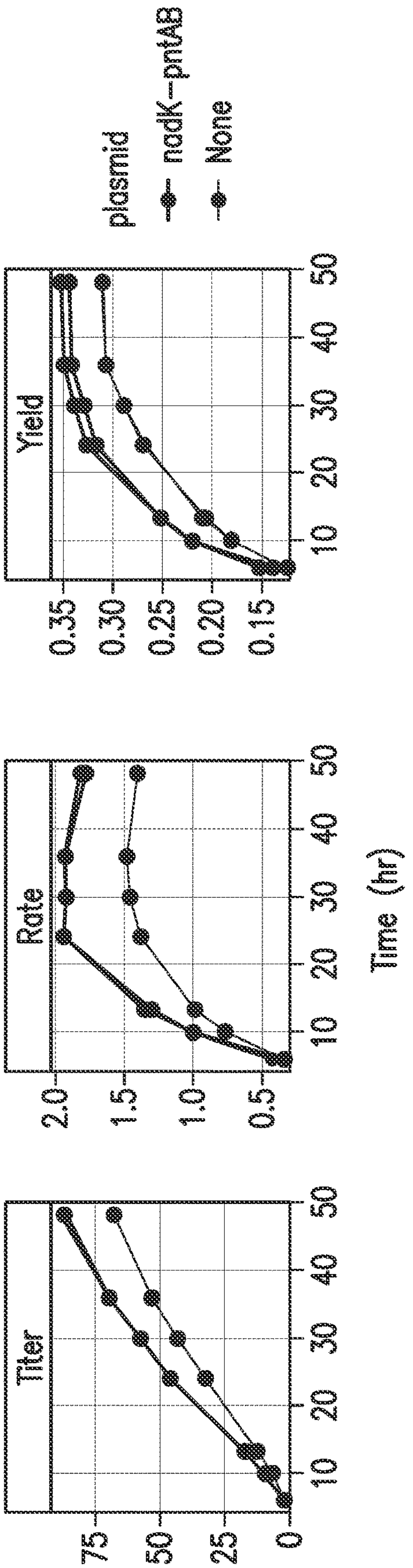
FIG. 1 shows that the L16182 strain (p115-nadK-p115-pntAB) exhibits greater titer, rate, and yield of 1,3-BDO, as compared to the L15863 stain (no plasmid).

This invention is directed, in part, to engineered biosynthetic routes to increased availability of cofactors, such as NADPH, for increased production of product molecules. Exemplary product molecules include, without limitation, 1,3-BDO, MMA, (3R)-hydroxybutyl (3R)-hydroxybutyrate, amino acids, isopropanol, adipate, caprolactam, 6-aminocaproic acid (6-ACA, hexametheylenediamine (HMDA), or methacrylic acid (MAA), although given the teachings and guidance provided herein, it will be recognized by one skilled in the art that any product molecule that has an NADPH dependent enzyme can exhibit enhanced product production through increased availability of NADPH. The present invention provides non-naturally occurring microbial organisms having one or more exogenous genes encoding enzymes that can catalyze increased production of NADPH. In some embodiments, these non-naturally occurring microbial organisms also have one of more exogenous genes encoding enzymes that can catalyze the production of a desired product, such as 1,3-BDO, MMA, (3R)-hydroxybutyl (3R)-hydroxybutyrate, amino acids, isopropanol, adipate, caprolactam, 6-aminocaproic acid (6-ACA, hexametheylenediamine (HMDA), or methacrylic acid (MAA).

In numerous engineered pathways, realization of maximum product yields based on carbohydrate feedstock is hampered by insufficient co-factors, such as reducing equivalents like NADPH, or by loss of co-factors, such as reducing equivalents like NADPH. In accordance with some embodiments, the present invention increases the yields of products by (i) enhancing the availability of NADPH, and (ii) increasing reducing equivalents for redox reactions. Products that can be produced by non-naturally occurring organisms and methods described herein include by way of example, but without limitation, 1,3-BDO, MMA, (3R)-hydroxybutyl (3R)-hydroxybutyrate, amino acids, isopropanol, adipate, caprolactam, 6-aminocaproic acid (6-ACA, hexametheylenediamine (HMDA), or methacrylic acid (MAA).

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins that result in an increase or decrease of a metabolic factor, for example. One exemplary metabolic factor includes NADPH. Exemplary metabolic factors also include, for example, 1,3-butanediol (1,3-BDO), methyl methacrylate (MMA), and/or (3R)-hydroxybutyl (3R)-hydroxybutyrate. A further exemplary metabolic factor includes, for example, non-proton-translocating NADH dehydrogenase II (NDH-2).

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "increased availability" or equivalents thereof, is intended to mean that the organism has greater production, reduced consumption, or both, of the referenced molecule such that the total amount of the referenced molecule is increased in the non-naturally occurring microbial organism. NADPH is an exemplary referenced molecule for increasing its availability in an organism. Exemplary reactions to increase availability of NADPH are disclosed herein. Exemplary pathways to increase production of, for example, 1,3-butanediol (1,3-BDO), a methyl methacrylate (MMA), and/or (3R)-hydroxybutyl (3R)-hydroxybutyrate are also disclosed herein.

As used herein, the term "attenuate," or grammatical equivalents thereof, is intended to mean to weaken, reduce or diminish the activity or amount of an enzyme or protein. Attenuation of the activity or amount of an enzyme or protein can mimic complete disruption if the attenuation causes the activity or amount to fall below a critical level required for a given pathway, reaction, or series of reactions to function. However, the attenuation of the activity or amount of an enzyme or protein that mimics complete disruption for one pathway, reaction, or series of reactions, can still be sufficient for a separate pathway, reaction, or series of reactions to continue to function. For example, attenuation of an endogenous enzyme or protein can be sufficient to mimic the complete disruption of the same enzyme or protein for production of a NADH of the invention, but the remaining activity or amount of enzyme or protein can still be sufficient to maintain other pathways, reactions, or series of reactions, such as a pathway, reaction, or series of reactions critical for the host microbial organism to survive, reproduce or grow. Attenuation of an enzyme or protein can also be weakening, reducing or diminishing the activity or amount of the enzyme or protein in an amount that is sufficient to increase yield of a factor, such as NADPH, of the invention, but does not necessarily mimic complete disruption of the enzyme or protein.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired enzyme or protein required for a pathway, reaction, or series of reactions. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

As used herein, the term "inducible promoter" is intended to mean a nucleotide sequence which, when operably linked with an exogenous nucleic acid encoding an enzyme, causes the amount of an enzyme in a cell to be dynamically expressed only when an inducer which corresponds to the promoter is present in the cell. An exemplary inducible promoter can be bound by a transcription regulatory protein that either represses or activates gene expression. The repressor or activator protein in turn is responsible to the stimulus, such as the presence or absence of a nutrient, a protein, or some other environmental signal.

As used herein, the term "variant" is intended to mean a form or version of an enzyme that differs from the wild-type enzyme. An exemplary variant is a mutant version of the enzyme where the amino acid sequence of the variant enzyme differs from the amino acid sequence at one of more at one or more of the homologous amino acids. A variant may have a different function or activity relative to the wild-type enzyme. However, a variant need not be a mutant, and can encompass polymorphisms, paralogs or orthologs.

As used herein, the term "unaltered" is intended to mean something that is not significantly changed relative to an analogous naturally occurring organism. A co-factor said to be unaltered refers to the co-factor being produced at the same or similar levels as would be observed in a naturally occurring organism.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "gene disruption," or grammatical equivalents thereof, is intended to mean a genetic alteration that renders the encoded gene product inactive. The genetic alteration can be, for example, deletion of the entire gene, deletion of a regulatory sequence required for transcription or translation, deletion of a portion of the gene that results in a truncated gene product, or by any of various mutation strategies that inactivate the encoded gene product. One particularly useful method of gene disruption is complete gene deletion because it reduces or eliminates the occurrence of genetic reversions in the non-naturally occurring microorganisms of the invention.

The non-naturally occurring microbial organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

As used herein, the term "1,3-butanediol," or "1,3-BDO" is intended to mean one of four stable isomers of butanediol having the chemical formula $C4H_{10}O_2$ and a molecular mass of 90.12 g/mol. The chemical compound 1,3-butanediol is known in the art as 1,3-butylene glycol (1,3-BG) and is also a chemical intermediate or precursor for a family of compounds commonly referred to as the BDO family of compounds.

As used herein, "methyl methacrylate," or "MMA," having the chemical formula $CH_2{=}C(CH_3)CO_2CH_3$ and a molecular mass of 100.12 g/mol, is the methyl ester of methacrylic acid (MAA). MMA is used as the monomer for the production of the transparent plastic polymethyl methacrylate (PMMA).

As used herein, the term "(3R)-hydroxybutyl (3R)-hydroxybutyrate" refers to a compound of formula (I):

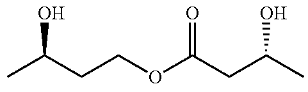
,

The term (3R)-hydroxybutyl (3R)-hydroxybutyrate is used interchangeably throughout with the terms (R)-(R)-3-hydroxybutyl 3-hydroxybutanoate, (3R) hydroxybutyl(3R)-hydroxybutyrate, and (R)-3-hydroxybutyl (R)-3hydroxybutanoate.

A metabolic modification refers to a biochemical reaction that is altered from its naturally occurring state. Therefore, non-naturally occurring microorganisms can have genetic modifications to nucleic acids encoding metabolic polypeptides, or functional fragments thereof. Exemplary metabolic modifications are disclosed herein.

In the case of gene disruptions, a particularly useful stable genetic alteration is a gene deletion. The use of a gene deletion to introduce a stable genetic alteration is particularly useful to reduce the likelihood of a reversion to a phenotype prior to the genetic alteration. For example, stable growth-coupled production of a biochemical can be achieved, for example, by deletion of a gene encoding an enzyme catalyzing one or more reactions within a set of metabolic modifications. The stability of growth-coupled production of a biochemical can be further enhanced through multiple deletions, significantly reducing the likelihood of multiple compensatory reversions occurring for each disrupted activity.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway, reaction, or series of reactions. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less than 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of *mycoplasma* 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having an increase in co-factor availability, such as NADPH, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionally related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST® algorithm, Clustal W and others compare and determine a raw sequence similarity or identity, and also determine the presence or significance of gaps in the sequence that can be assigned a weight or score. Such algorithms also are known in the art and are similarly applicable for determining nucleotide sequence similarity or identity. Parameters for sufficient similarity to determine relatedness are computed based on well-known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity that is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST® algorithm, for example, can be as set forth below. Briefly, amino acid sequence alignments can be performed using BLASTP® algorithm version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN® algorithm version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In certain embodiments, provided herein is a non-naturally occurring microbial organism having an increased availability of reduced nicotinamide adenine dinucleotide phosphate (NADPH). In certain embodiments, the organism includes one or more exogenous nucleic acids encoding an enzyme expressed in a sufficient amount to increase availability of NADPH, wherein said at least one exogenous nucleic acid is selected from ATP-NADH kinase, NAD(P) transhydrogenase subunit alpha part 2 (pntAB), ATP-NAD+ kinase (nadK), and NADP-dependent glyceraldehyde-3-phosphate dehydrogenase (gapN). In other embodiments, the microbial organism comprises one or more gene attenuations occurring in genes encoding proteins or enzymes that result in an increased ratio of NADPH to NADH present in the cytosol of said non-naturally occurring microbial organism following said disruptions. In certain embodiments, the microbial organism comprises a combination of one or more exogenous nucleic acids encoding an enzyme expressed in a sufficient amount to increase availability of NADPH, wherein said at least one exogenous nucleic acid is selected from ATP-NADH kinase, NAD(P) transhydrogenase subunit alpha part 2 (pntAB), ATP-NAD+kinase (nadK), and NADP-dependent glyceraldehyde-3-phosphate dehydrogenase (gapN), and one or more gene attenuations occurring in genes encoding proteins or enzymes that result in an increased ratio of NADPH to NADH present in the cytosol of said non-naturally occurring microbial organism following said disruptions.

In some embodiments, the microbial organism comprises one exogenous nucleic acid encoding an enzyme expressed in a sufficient amount to increase availability of NADPH. In one embodiment, the one exogenous nucleic acid encodes ATP-NADH kinase. In another embodiment, the one exogenous nucleic acid encodes gapN.

In other embodiments, the microbial organism comprises two exogenous nucleic acids each encoding an enzyme expressed in a sufficient amount to increase availability of NADPH. In one embodiment, the two exogenous nucleic acids encode pntAB and nadK. In another embodiment, the two exogenous nucleic acids encode ATP-NADH kinase and gapN.

In further embodiments, the microbial organism comprises three exogenous nucleic acids each encoding an enzyme expressed in a sufficient amount to increase availability of NADPH. In some embodiments, the three exogenous nucleic acids encode ATP-NADH kinase, pntAB and nadK. In other embodiments, the three exogenous nucleic acids encode gapN, pntAB and nadK.

In certain embodiments, the microbial organism comprises four exogenous nucleic acids each encoding an enzyme expressed in a sufficient amount to increase availability of NADPH. In one embodiment, the four exogenous nucleic acids encode gapN, ATP-NADH kinase, pntAB, and nadK.

As disclosed herein, the ATP-NADH kinase catalyzes the conversion of NAD into NADPH. In specific embodiments, the ATP-NADH kinase activity is equivalent to the combined activity of a NAD(P) transhydrogenase, and a ATP-NAD+kinase. In some embodiments, the ATP-NADH is a variant of ATP-NAD+kinase.

It is understood that the ATP-NADH kinase need not have substrate specificity for only NADH. In some embodiments, the ATP-NADH has substrate specificities for both NAD+ and NADH. It is also understood that the ATP-NADH can be a natural variant of ATP-NAD+kinase, or a mutant of ATP-NAD+. For example, the ATP-NAD kinase can be from *S. cerevisiae* (Utr1p, Yef1p, and Pos5p) and exhibit NADH kinase activity in addition to NAD kinase activity. In other embodiments, the ATP-NAD+kinase variant can be converted into a ATP-NADH by mutation. For example, a single arginine (Arg) residue near the amino acids participating in the binding of the nicotinamide ring of NAD+ can be substituted for a glycine (Gly) or polar amino acid in ATP-NAD+ to convert the substrate specificity into an ATP-NADH.

It is also understood that the ATP-NADH variant can have increased NADH kinase activity relative to ATP-NAD. In some embodiments, the NADH kinase activity of the ATP-NADH variant is about 5%, about 10%, about 15%, about 20%, about 25%, about 30%, about 40%, about 50%, about 60%, about 70%, about 80%, about 90%, about 100%, about 125%, about 150%, about 175%, about 200%, or greater. In yet further embodiments, the ratio of NADH kinase activity to NAD kinase activity is about 5%, about 10%, about 15%, about 20%, about 25%, about 30%, about 40%, about 50%, about 60%, about 70%, about 80%, about 90%, about 100%, about 125%, about 150%, about 175%, about 200%, or greater. In some embodiments, the non-naturally occurring microbial organism provided herein has an increased ratio of NADPH/NADP ratio. In some embodiments, the increased ratio is about 1.5 fold. In other embodiments, the increased ratio is about 2.0 fold. In further embodiments, the increased ratio is about 2.5 fold. In some embodiments, the increased ratio is about 3.0 fold. In yet further embodiments, the increased ratio is about 3.5 fold. In some embodiments, the increased ratio is about 4.0 fold. In other embodiments, the increased ratio is about 5.0 fold.

As described previously, the microbial organism can also express an exogenous nucleic acid encoding an enzyme expressed in a sufficient amount to produce gapN. In some embodiments, gapN is expressed at a higher level than an endogenous glyceraldehyde-3-phosphate dehydrogenase A (gapA). In certain embodiments, the ratio of gapN to gapA+gapN is at least about 10%, about 15%, about 20%, about 25%, about 30%, about 40%, about 50%, about 60%, about 70%, about 80%, about 90%, about 95%, or more.

It is understood that a higher expression of gapN relative to gapA will result in a greater activity of gapN relative to the activity of gapA. In some embodiments, a greater activity of gapN can be achieved by an attenuated gapA. In specific embodiments, attenuated gapA comprises reduced expression of gapA.

As provided herein, gapN is an NADP dependent enzyme that catalyzes the oxidation of glyceraldehyde-3-phosphate (GAP) to 3-phosphoglycerate (3-PG or 3-PGA) during glycolysis, and generates NADPH in the process. Therefore, in some embodiments, the gapN increases production of NADPH. In certain embodiments, the exogenous gapN is from a methanotrophic bacteria. In further embodiments, gapN is from *Bacillus methanolicus*. It is understood that homologs of *B. methanolicus* gapN that produce NADPH are also suitable. Therefore, in some embodiments, gapN is a homolog of *B. methanolicus* gapN. Exemplary homologs and their relative homology to gapN are provided in Table 1 below.

TABLE 1

| Accession | Organism | % ID to *B. methanolicus* gapN |
|---|---|---|
| WP_003346738 | *Bacillus methanolicus* | 100 |
| WP_003351798 | *Bacillus methanolicus* | 95.01 |
| WP_026964094 | *Alicyclobacillus pomorum* | 68.75 |
| WP_089533800 | *Virgibacillus necropolis* | 66.527 |
| WP_011983786 | *Bacillus cytotoxicus* | 65.89 |
| WP_097894576 | *Bacillus* | 65.89 |
| WP_087097851 | *Bacillus cytotoxicus* | 65.678 |
| WP_068447188 | *Lentibacillus amyloliquefaciens* | 65.546 |
| WP_098359346 | *Bacillus cereus* | 65.466 |
| WP_098558080 | *Bacillus cereus* | 65.466 |
| EEL51944 | *Bacillus cereus* Rock3-44 | 65.254 |
| WP_000208150 | *Bacillus cereus* | 65.254 |
| WP_088038585 | *Bacillus mycoides* | 65.254 |
| WP_000213646 | *Bacillus cereus* group | 65.042 |
| WP_000213650 | *Bacillus cereus* group | 65.042 |
| WP_002010835 | *Bacillus* | 65.042 |
| WP_002125495 | *Bacillus cereus* group | 65.042 |
| WP_002134606 | *Bacillus cereus* | 65.042 |
| WP_002140513 | *Bacillus cereus* | 65.042 |
| WP_016093244 | *Bacillus cereus* | 65.042 |
| WP_017153122 | *Bacillus bingmayongensis* | 65.042 |
| WP_025150283 | *Bacillus* sp. H1a | 65.042 |
| WP_070141032 | *Bacillus cereus* group | 65.042 |
| WP_078178206 | *Bacillus mycoides* | 65.042 |
| WP_088035237 | *Bacillus thuringiensis* | 65.042 |
| WP_088106515 | *Bacillus cereus* | 65.042 |
| WP_088292461 | *Bacillus mycoides* | 65.042 |
| WP_105585763 | *Bacillus* sp. MYb209 | 65.042 |
| WP_105989975 | *Bacillus* sp. M21 | 65.042 |
| WP_077328816 | *Virgibacillus siamensis* | 64.916 |
| ABK84147 | *Bacillus thuringiensis* str. Al Hakam | 64.831 |
| WP_000213613 | *Bacillus* | 64.831 |
| WP_000213620 | *Bacillus cereus* | 64.831 |
| WP_000213631 | *Bacillus* | 64.831 |
| WP_000213637 | *Bacillus* | 64.831 |
| WP_000213642 | *Bacillus cereus* | 64.831 |
| WP_000213643 | *Bacillus thuringiensis* | 64.831 |
| WP_002063972 | *Bacillus cereus* | 64.831 |
| WP_002087376 | *Bacillus cereus* | 64.831 |
| WP_003205982 | *Bacillus cereus* group | 64.831 |
| WP_016113266 | *Bacillus cereus* group | 64.831 |
| WP_018783531 | *Bacillus* | 64.831 |
| WP_048373546 | *Bacillus* sp. LK2 | 64.831 |
| WP_052943462 | *Bacillus thuringiensis* | 64.831 |
| WP_070169862 | *Bacillus mycoides* | 64.831 |
| WP_074615306 | *Bacillus cereus* | 64.831 |
| WP_076869997 | *Bacillus cereus* | 64.831 |
| WP_078985830 | *Bacillus anthracis* | 64.831 |
| WP_086388821 | *Bacillus thuringiensis* | 64.831 |
| WP_097786660 | *Bacillus pseudomycoides* | 64.831 |
| WP_097793698 | *Bacillus pseudomycoides* | 64.831 |
| WP_097955132 | *Bacillus toyonensis* | 64.831 |
| WP_098116852 | *Bacillus pseudomycoides* | 64.831 |
| WP_098162831 | *Bacillus toyonensis* | 64.831 |
| WP_098335345 | *Bacillus cereus* | 64.831 |
| WP_098492658 | *Bacillus cereus* | 64.831 |
| WP_098925877 | *Bacillus anthracis* | 64.831 |
| WP_101195307 | *Bacillus* sp. HBCD-sjtu | 64.831 |
| WP_101218479 | *Bacillus cereus* | 64.831 |
| EEM06723 | *Bacillus mycoides* Rock1-4 | 64.619 |
| WP_000213623 | *Bacillus cereus* | 64.619 |
| WP_000213628 | *Bacillus thuringiensis* | 64.619 |
| WP_000213640 | *Bacillus anthracis* | 64.619 |
| WP_002114874 | *Bacillus cereus* | 64.619 |
| WP_002201632 | *Bacillus cereus* group | 64.619 |

TABLE 1-continued

| Accession | Organism | % ID to *B. methanolicus* gapN |
|---|---|---|
| WP_018767657 | *Bacillus* | 64.619 |
| WP_033798237 | *Bacillus mycoides* | 64.619 |
| WP_040119176 | *Bacillus mycoides* | 64.619 |
| WP_041488274 | *Bacillus cereus* group | 64.619 |
| WP_042982143 | *Bacillus mycoides* | 64.619 |
| WP_062821571 | *Bacillus cereus* | 64.619 |
| WP_070172070 | *Bacillus cereus* group | 64.619 |
| WP_071771128 | *Bacillus* sp. NH11B | 64.619 |
| WP_088077715 | *Bacillus mycoides* | 64.619 |
| WP_088312506 | *Bacillus cereus* | 64.619 |
| WP_097831246 | *Bacillus cereus* | 64.619 |
| WP_097926598 | *Bacillus toyonensis* | 64.619 |
| WP_097988492 | *Bacillus pseudomycoides* | 64.619 |
| WP_098017785 | *Bacillus pseudomycoides* | 64.619 |
| WP_098040080 | *Bacillus pseudomycoides* | 64.619 |
| WP_098101492 | *Bacillus pseudomycoides* | 64.619 |
| WP_098135232 | *Bacillus pseudomycoides* | 64.619 |
| WP_098187957 | *Bacillus pseudomycoides* | 64.619 |
| WP_098226164 | *Bacillus toyonensis* | 64.619 |
| WP_098362014 | *Bacillus cereus* | 64.619 |
| WP_098610496 | *Bacillus pseudomycoides* | 64.619 |
| WP_098639221 | *Bacillus anthracis* | 64.619 |
| WP_098716171 | *Bacillus pseudomycoides* | 64.619 |
| WP_101168380 | *Bacillus* sp. SN10 | 64.619 |
| AIE81030 | *Bacillus cereus* | 64.482 |
| WP_000213645 | *Bacillus cereus* | 64.407 |
| WP_002116502 | *Bacillus cereus* | 64.407 |
| WP_002159137 | *Bacillus cereus* group | 64.407 |
| WP_006093663 | *Bacillus* | 64.407 |
| WP_097834495 | *Bacillus pseudomycoides* | 64.407 |
| WP_097849866 | *Bacillus pseudomycoides* | 64.407 |
| WP_098160819 | *Bacillus pseudomycoides* | 64.407 |
| WP_085965931 | *Bacillus cereus* | 64.271 |
| WP_098814110 | *Bacillus pseudomycoides* | 64.195 |
| WP_098929011 | *Bacillus pseudomycoides* | 64.195 |

It is understood that the expression of the exogenous nucleic acids disclosed herein can be regulated by various promoters, such as an endogenous promoter, a constitutive promoter, or an inducible promoter. A person of average skill in the art would understand which type of promoter to use given the level and duration of expression desired. For example, if the level of expression desired was the endogenous level, a person of average skill would understand that an endogenous promoter could be used to control the expression of the exogenous nucleic acid. Further, if the expression was desired to be, for example, temporary or at a specific point during fermentation, an endogenous promoter could be used to control the expression of the exogenous nucleic acid. However, if the expression was desired to be, for example, constant and robust, a constitutive promoter could be used to control the expression of the exogenous nucleic acid. Therefore, in some embodiments, the exogenous nucleic acid encoding an enzyme is regulated by an endogenous promoter, a constitutive promoter, or an inducible promoter.

As disclosed herein, the microbial organism having an increased availability of NADPH can further include a 1,3-butanediol (1,3-BDO) pathway, a methyl methacrylate (MMA) pathway, a (3R)-hydroxybutyl (3R)-hydroxybutyrate pathway, an amino acid biosynthesis pathway, a 3HB-CoA pathway, a methyl methacrylate (MMA) pathway, an adipate pathway, a caprolactam pathway, a 6-aminocaproic acid (6-ACA) pathway, a hexametheylenediamine (HMDA) pathway, or a methacrylic acid (MAA) pathway.

In certain embodiments, the microbial organism having an increased availability of NADPH further includes a 1,3-butanediol (1,3-BDO) pathway. In some embodiments, the 1,3-BDO pathway comprises an enzyme selected from: 1) an acetoacetyl-CoA reductase (CoA-dependent, aldehyde forming), 2) a 3-oxobutyraldehyde reductase (ketone reducing), 3) a 3-hydroxybutyraldehyde reductase, 4) an acetoacetyl-CoA reductase (CoA-dependent, alcohol forming), 5) a 3-oxobutyraldehyde reductase (aldehyde reducing), 6) a 4-hydroxy, 2-butanone reductase, 7) an acetoacetyl-CoA reductase (ketone reducing), 8) a 3-hydroxybutyryl-CoA reductase (aldehyde forming), and 9) a 3-hydroxybutyryl-CoA reductase (alcohol forming). In some embodiments, the 1,3-BDO pathway comprises a nucleic acid encoding an acetoacetyl-CoA reductase (phaB). In specific embodiments, the acetoacetyl-CoA reductase is a mutant acetoacetyl-CoA reductase. In some embodiments, the mutant acetoacetyl-CoA reductase uses NADH as a substrate. Any number of nucleic acids encoding these enzymes can be further introduced into a host microbial organism including one, two, three, four, five, six, seven, eight, up to all nine of the nucleic acids that encode these enzymes. Where one, two, three, four, five, six, seven, or eight exogenous nucleic acids are introduced, such nucleic acids can be any permutation of the additional nine nucleic acids.

In certain embodiments, the microbial organism having an increased availability of NADPH further includes a (3R)-hydroxybutyl (3R)-hydroxybutyrate pathway. In some embodiments, the (3R)-hydroxybutyl (3R)-hydroxybutyrate pathway comprises at least one exogenous nucleic acid encoding an enzyme selected from: 1) a (3R)-hydroxybutyl (3R)-hydroxybutyrate ester forming enzyme, 2) a (3R)-hydroxybutyryl-CoA:(R)-1,3-butanediol alcohol transferase, 3) a (3R)hydroxybutyl 3-oxobutyrate ester forming enzyme, 4) an acetoacetyl-CoA:(R)-1,3-butanediol alcohol transferase, 5) a (3R)-hydroxybutyl 3-oxobutyrate reductase, 6) a (3R)-hydroxybutyryl-ACP:(R)-1,3-butanediol ester synthase, and 7) an acetoacetyl-ACP:(R)-1,3-butanediol ester synthase. In some embodiments, the (3R)-hydroxybutyl (3R)-hydroxybutyrate pathway comprises a nucleic acid encoding an acetoacetyl-CoA reductase (phaB). In specific embodiments, the acetoacetyl-CoA reductase is a mutant acetoacetyl-CoA reductase. In some embodiments, the mutant acetoacetyl-CoA reductase uses NADH as a substrate. Any number of nucleic acids encoding these enzymes can be further introduced into a host microbial organism including one, two, three, four, five, six, seven, up to all eight of the nucleic acids that encode these enzymes. Where one, two, three, four, five, six, or seven exogenous nucleic acids are introduced, such nucleic acids can be any permutation of the additional eight nucleic acids.

In certain embodiments, the microbial organism having an increased availability of NADPH can further include a MMA pathway. In specific embodiments, the MMA pathway comprises at least one exogenous nucleic acid encoding an enzyme selected from: (a) a 4-hydroxybutyryl-CoA dehydratase, a crotonase, a 2-hydroxyisobutyryl-CoA mutase, a 2-hydroxyisobutyryl-CoA dehydratase, and a methacrylic acid (MAA)-CoA: methanol transferase; or (b) a 4-hydroxybutyryl-CoA dehydratase, a crotonase, a 2-hydroxyisobutyryl-CoA mutase, a 3-hydroxyisobutyryl-CoA: methanol transferase, and a methyl-2-hydroxyisobutyrate dehydratase. In some embodiments, the MMA pathway further comprises at least one exogenous nucleic acid encoding an enzyme selected from (c) a methacrylic acid (MAA)-CoA: methanol transferase, a 4-hydroxybutyryl-CoA mutase, and a 3-hydroxyisobutyryl-CoA dehydratase; or (d) a 4-hydroxybutyryl-CoA mutase, a 3-hydroxyisobutyryl-CoA: methanol transferase, and a methyl-3-hydroxyisobutyrate dehydratase.

In other embodiments, the microbial organism having an increased availability of NADPH can further include an amino acid production pathway. The biosynthesis of amino acids in organisms capable of producing them, such as bacteria, has been well characterized (for review of bacterial amino acid biosynthesis and regulation thereof, see Umbarger, H. E. (1978) Ann. Rev. Biochem. 47: 533-606). Glutamate is synthesized by the reductive amination of α-ketoglutarate, an intermediate in the citric acid cycle. Glutamine, proline, and arginine are each subsequently produced from glutamate. The biosynthesis of serine is a three-step process beginning with 3-phosphoglycerate (an intermediate in glycolysis), and resulting in this amino acid after oxidation, transamination, and hydrolysis steps. Both cysteine and glycine are produced from serine; the former by the condensation of homocysteine with serine, and the latter by the transferal of the side-chain (3-carbon atom to tetrahydrofolate, in a reaction catalyzed by serine transhydroxymethylase. Phenylalanine, and tyrosine are synthesized from the glycolytic and pentose phosphate pathway precursors erythrose 4-phosphate and phosphoenolpyruvate in a 9-step biosynthetic pathway that differ only at the final two steps after synthesis of prephenate. Tryptophan is also produced from these two initial molecules, but its synthesis is an 11-step pathway. Tyrosine may also be synthesized from phenylalanine, in a reaction catalyzed by phenylalanine hydroxylase. Alanine, valine, and leucine are all biosynthetic products of pyruvate, the final product of glycolysis. Aspartate is formed from oxaloacetate, an intermediate of the citric acid cycle. Asparagine, methionine, threonine, and lysine are each produced by the conversion of aspartate. Isoleucine is formed from threonine. A complex 9-step pathway results in the production of histidine from 5-phosphoribosyl-1-pyrophosphate, an activated sugar.

In some embodiments, the amino acid production pathway comprises a tryptophan production pathway that comprises at least one exogenous nucleic acid encoding an enzyme selected from trpE, trpG-D, trpC-F, trpB or trpA. Production of tryptophan using microorganisms is known in the art, as exemplified in U.S. Pat. No. 6,180,373, and U.S. application Ser. No. 14/371,465, published as U.S. 2015-0147788 A1, each of which are incorporated herein by reference in their entirety. In other embodiments, embodiments, the amino acid production pathway comprises a threonine production pathway that comprises at least one exogenous nucleic acid encoding an enzyme selected from: thrA, thrB, or thrC. Production of threonine using microorganisms is known in the art, as exemplified in U.S. Pat. No. 4,278,765, which is incorporated herein by reference in its entirety embodiments. In some embodiments, the amino acid production pathway comprises a lysine production pathway that comprises at least one exogenous nucleic acid encoding an enzyme selected from: ask, dapA, lysC, asd, dapA, dapB, dapD, dapC/argD, dapE, dapF, dapL, ddh, or lysA. Production of lysine using microorganisms is known in the art, as exemplified in U.S. Pat. No. 8,048,651, which is incorporated herein by reference in its entirety. However, it is understood that any amino acid production pathway that utilizes NADPH can benefit and that the above exemplified pathway are not intended to be limiting.

In other embodiments, the microbial organism having an increased availability of NADPH can further include a 3HB-CoA pathway. In specific embodiments, the 3HB-CoA pathway comprises at least one exogenous nucleic acid encoding an enzyme selected from: an acetyl-CoA thiolase, and a 3-hydroxybutyryl-CoA dehydrogenase.

In some embodiments, the microbial organism having an increased availability of NADPH can further include a MMA pathway. Production of MMA using microorganisms is known in the art, as exemplified in U.S. Pat. Nos. 9,133,487, and 9,346,902, each of which are incorporated herein by reference in their entirety. In certain embodiments, the MMA pathway comprises an MAA pathway that is then esterified with methanol to produce MMA. In specific embodiments, the MMA pathway comprises at least one exogenous nucleic acid encoding an enzyme selected from (a) a 4-hydroxybutyryl-CoA dehydratase, a crotonase, a 2-hydroxyisobutyryl-CoA mutase, a 2-hydroxyisobutyryl-CoA dehydratase, and a methacrylic acid (MAA)-CoA: methanol transferase; or (b) a 4-hydroxybutyryl-CoA dehydratase, a crotonase, a 2-hydroxyisobutyryl-CoA mutase, a 3-hydroxyisobutyryl-CoA: methanol transferase, and a methyl-2-hydroxyisobutyrate dehydratase. In certain embodiments, the MMA pathway further comprises at least one exogenous nucleic acid encoding an enzyme selected from a second MMA pathway comprising: (c) a methacrylic acid (MAA)-CoA: methanol transferase, a 4-hydroxybutyryl-CoA mutase, and a 3-hydroxyisobutyryl-CoA dehydratase; or (d) a 4-hydroxybutyryl-CoA mutase, a 3-hydroxyisobutyryl-CoA: methanol transferase, and a methyl-3-hydroxyisobutyrate dehydratase.

In certain embodiments, the microbial organism having an increased availability of NADPH can further include a 6-ACA pathway. In specific embodiments, the 6-ACA pathway comprises at least one exogenous nucleic acid encoding an enzyme selected from 2-amino-7-oxosubarate keto-acid decarboxylase, 2-amino-7-oxoheptanoate decarboxylase, 2-amino-7-oxoheptanoate oxidoreductase, 2-aminopimelate decarboxylase, 6-aminohexanal oxidoreductase, 2-amino-7-oxoheptanoate decarboxylase, or 2-amino-7-oxosubarate amino acid decarboxylase. In other embodiments, the 6-ACA pathway comprises at least one exogenous nucleic acid encoding an enzyme selected from 3-oxo-6-aminohexanoyl-CoA thiolase; 3-oxo-6-aminohexanoyl-CoA reductase; 3-hydroxy-6-aminohexanoyl-CoA dehydratase; 6-aminohex-2-enoyl-CoA reductase; and 6-aminocaproyl-CoA/acyl-CoA transferase, 6-aminocaproyl-CoA synthase, or 6-aminocaproyl-CoA hydrolase.

In other embodiments, the microbial organism having an increased availability of NADPH can further include a caprolactam pathway. In specific embodiments, the caprolactam pathway comprises at least one exogenous nucleic acid encoding an enzyme selected from 3-oxoadipyl-CoA thiolase, 3-oxoadipyl-CoA reductase, 3-hydroxyadipyl-CoA dehydratase, 5-carboxy-2-pentenoyl-CoA reductase, adipyl-CoA reductase (aldehyde forming), 6-aminocaproate transaminase, 6-aminocaproate dehydrogenase, 6-aminocaproyl-CoA/acyl-CoA transferase, and 6-aminocaproyl-CoA synthase.

In certain embodiments, the microbial organism having an increased availability of NADPH can further include an adipate pathway. In specific embodiments, the adipate pathway comprises at least one exogenous nucleic acid encoding an enzyme selected from 3-oxoadipyl-CoA thiolase, 3-oxoadipyl-CoA reductase, 3-hydroxyadipyl-CoA dehydratase, 5-carboxy-2-pentenoyl-CoA reductase, adipyl-CoA hydrolase, adipyl-CoA ligase, adipyl-CoA transferase and phosphotransadipylase/adipate kinase.

In other embodiments, the microbial organism having an increased availability of NADPH can further include a hexamethylenediamine (HMDA) pathway. In specific embodiments, the HMDA pathway comprises at least one exogenous nucleic acid encoding an enzyme selected from 3-oxoadipyl-CoA thiolase, 3-oxoadipyl-CoA reductase, 3-hydroxyadipyl-CoA dehydratase, 5-carboxy-2-pentenoyl-CoA reductase, adipyl-CoA reductase (aldehyde forming), 6-aminocaproate transaminase, 6-aminocaproate dehydrogenase, 6-aminocaproyl-CoA/acyl-CoA transferase, 6-aminocaproyl-CoA synthase, 6-aminocaproyl-CoA reductase (aldehyde forming), HMDA transaminase, and HMDA dehydrogenase. In other embodiments, the HMDA pathway comprises at least one exogenous nucleic acid encoding an enzyme selected from 6-aminocaproyl-CoA/acyl-CoA transferase or 6-aminocaproyl-CoA synthase; 6-aminocaproyl-CoA reductase (aldehyde forming); and hexamethylenediamine transaminase or hexamethylenediamine dehydrogenase.

In some embodiments, the microbial organism having an increased availability of NADPH can further include a MAA pathway. In specific embodiments, the MAA pathway comprises at least one exogenous nucleic acid encoding an enzyme selected from (1) (i) a succinyl-CoA transferase, ligase, or synthetase; (ii) a methylmalonyl-CoA mutase; (iii) a methylmalonyl-CoA epimerase; (iv) a methylmalonyl-CoA reductase (aldehyde forming); (v) a methylmalonate semialdehyde reductase; and (vi) a 3-hydroxyisobutyrate dehydratase; (2) (i) a succinyl-CoA transferase, ligase, or synthetase; (ii) a methylmalonyl-CoA mutase; (iii) a methylmalonyl-CoA reductase (aldehyde forming); (iv) a methylmalonate semialdehyde reductase; and (v) a 3-hydroxyisobutyrate dehydratase; or (3) (i) a succinyl-CoA transferase, ligase, or synthetase; (ii) a methylmalonyl-CoA mutase; (iii) a methylmalonyl-CoA reductase (alcohol forming); and (iv) a 3-hydroxyisobutyrate dehydratase.

As provided herein, the microbial organism can also be modified so as to reduce the consumption of NADPH. Accordingly, one or more NADPH dependent enzymes can be attenuated, and/or deleted. In certain embodiments, the microbial organism having an increased availability of NADPH can further include one or more gene attenuations. In specific embodiments, the one or more gene attenuations occur in genes encoding proteins or enzymes that result in an increased ratio of NADPH to NADH present in the cytosol of said non-naturally occurring microbial organism following the disruptions. In further embodiments, the one or more gene attenuations comprise a gene attenuation in a gene encoding non-proton-translocating NADH dehydrogenase II (NDH-2). In yet further embodiments, the gene attenuation in a gene encoding NDH-2 comprises a deletion of NDH-2 and the attenuation of NDH-2 decreases NADPH consumption.

In certain embodiments, the invention provides a non-naturally occurring microbial organism having an increased availability of NADPH, wherein the non-naturally occurring microbial organism has at least one exogenous nucleic acid encoding an enzyme or protein that converts a substrate to a product selected from the group consisting of NADP+ to NADPH, NAD+ to NADP+, NADH to NAD+, NAD+ to NADH, D-glyceraldehyde 3-phosphate to 3-phospho-D-glycerate, and D-glyceraldehyde 3-phosphate to 3-phospho-D-glyceroyl phosphate.

In some embodiments, the non-naturally occurring microbial organism having an increased availability of NADPH further includes a 1,3-butanediol pathway. In some embodiments, the 1,3-butanediol pathway includes at least one exogenous nucleic acid encoding an enzyme or protein that converts a substrate to a product selected from the group consisting of glucose to pyruvate, pyruvate to acetyl-CoA, acetyl-CoA to acetoacetyl-CoA, acetoacetyl-CoA to 3-hydroxybutyryl-CoA, 3-hydroxybutyryl-CoA to 3-hydroxybutryaldehyde, and 3-hydroxybutryaldehyde to 1,3-BDO.

In some embodiments, the non-naturally occurring microbial organism having an increased availability of NADPH further includes a (3R)-hydroxybutyl (3R)-hydroxybutyrate pathway. In some embodiments, the (3R)-hydroxybutyl (3R)-hydroxybutyrate pathway includes at least one exogenous nucleic acid encoding an enzyme or protein that converts a substrate to a product selected from the group consisting of (R)-1,3-butanediol and (3R)-hydroxybutyrate to (3R)-hydroxybutyl (3R)-hydroxybutyrate, (R)-1,3-butanediol and (3R)-hydroxybutyryl-CoA to (3R)-hydroxybutyl (3R)-hydroxybutyrate, (R)-1,3-butanediol and (3R)-hydroxybutyl-ACP to (3R)-hydroxybutyl (3R)-hydroxybutyrate, (R)-1,3-butanediol and acetoacetate to (3R)-hydroxybutyl 3-oxobutyrate, (R)-1,3-butanediol and acetoacetyl-CoA to (3R)-hydroxybutyl 3-oxobutyrate, (R)-1,3-butanediol and acetoacetyl-ACP to (3R)-hydroxybutyl 3-oxobutyrate, (3R)-hydroxybutyl 3-oxobutyrate to (3R)-hydroxybutyl (3R)-hydroxybutyrate, acetyl-CoA to malonyl-CoA, malonyl-CoA to acetoacetyl-CoA, acetyl-CoA to acetoacetyl-CoA, acetoacetyl-CoA to acetoacetate, acetoacetyl-CoA to (3 S)-hydroxybutyryl-CoA, (3 S)-hydroxybutyryl-CoA to (3R)-hydroxybutyryl-CoA, (3R)-hydroxybutyryl-CoA to (3R)-hydroxybutyrate, (3R)-hydroxybutyryl-CoA to (3R)-hydroxybutyraldehyde, (3R)-hydroxybutyrate to (3R)-hydroxybutyraldehyde, (3R)-hydroxybutyraldehyde to (R)-1,3-butanediol, malonyl-ACP to acetoacetyl-ACP, acetoacetyl-ACP to acetoacetyl-CoA, acetoacetyl-ACP to (3R)-hydroxybutyryl-ACP, (3R)-hydroxybutyryl-ACP to (3R)-hydroxybutyryl-CoA, (3R)-hydroxybutyryl-ACP to (3R)-hydroxybutyrate, (3R)-hydroxybutyryl-ACP to (3R)-hydroxybutyraldehyde, and (3R)-hydroxybutyryl-ACP to (R)-1,3-butanediol. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of a (3R)-hydroxybutyl (3R)-hydroxybutyrate pathway, such as those disclosed in U.S. application Ser. No. 14/893,510, published as U.S. 2016-0108442 A1, which is incorporated herein by reference in its entirety.

In some embodiments, the non-naturally occurring microbial organism having an increased availability of NADPH further includes a MMA pathway. In some embodiments, the MMA pathway includes at least one exogenous nucleic acid encoding an enzyme or protein that converts a substrate to a product selected from the group consisting of 4-HB-CoA to crotonyl-CoA and 3HIB-CoA, crotonyl-CoA to 3HB-CoA, 3HIB-CoA to MAA-CoA or methyl-3HIB, and MAA-CoA or methyl-3HIB to MMA. In a further embodiment, the invention provides a non-naturally occurring microbial organism having a MMA pathway, wherein the non-naturally occurring microbial organism comprises at least one exogenous nucleic acid encoding an enzyme or protein that converts a substrate to a product selected from the group consisting of 4HB-CoA to crotonyl-CoA, crotonyl-CoA to (3R)—HB-CoA or (3S)-HB-CoA, (3R)—HB-CoA or (3S)—HB-CoA to 2-HIB-CoA, 2-HIB-CoA to MAA-CoA or 2HIB-Me, and MAA-CoA or 2HIB-Me to MMA. In yet a further embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of 4HB-CoA to crotonyl-CoA, crotonyl-CoA to (3R)—HB-CoA or (3 S)—HB-CoA, (3R)—HB-CoA or (3S)-HB-CoA to (3R)- or (3S)-1,3 BDO.

In some embodiments, the non-naturally occurring microbial organism having an increased availability of NADPH further includes an amino acid biosynthesis pathway. As described above, the biosynthesis of amino acids in organisms capable of producing them, such as bacteria, has been well characterized (for review of bacterial amino acid biosynthesis and regulation thereof, see Umbarger, H. E. (1978) Ann. Rev. Biochem. 47: 533-606). Glutamate is synthesized by the reductive amination of α-ketoglutarate, an intermediate in the citric acid cycle. Glutamine, proline, and arginine are each subsequently produced from glutamate. The biosynthesis of serine is a three-step process beginning with 3-phosphoglycerate (an intermediate in glycolysis), and resulting in this amino acid after oxidation, transamination, and hydrolysis steps. Both cysteine and glycine are produced from serine; the former by the condensation of homocysteine with serine, and the latter by the transferal of the side-chain (3-carbon atom to tetrahydrofolate, in a reaction catalyzed by serine transhydroxymethylase. Phenylalanine, and tyrosine are synthesized from the glycolytic and pentose phosphate pathway precursors erythrose 4-phosphate and phosphoenolpyruvate in a 9-step biosynthetic pathway that differ only at the final two steps after synthesis of prephenate. Tryptophan is also produced from these two initial molecules, but its synthesis is an 11-step pathway. Tyrosine may also be synthesized from phenylalanine, in a reaction catalyzed by phenylalanine hydroxylase. Alanine, valine, and leucine are all biosynthetic products of pyruvate, the final product of glycolysis. Aspartate is formed from oxaloacetate, an intermediate of the citric acid cycle. Asparagine, methionine, threonine, and lysine are each produced by the conversion of aspartate. Isoleucine is formed from threonine. A complex 9-step pathway results in the production of histidine from 5-phosphoribosyl-1-pyrophosphate, an activated sugar.

In an additional embodiment, the invention provides a non-naturally occurring microbial organism having a methacrylic acid pathway, wherein the non-naturally occurring microbial organism comprises at least one exogenous nucleic acid encoding an enzyme or protein that converts a substrate to a product selected from the group consisting of acetyl-CoA and pyruvate to citramalate, citramalate to citraconate, and citraconate to methacrylate; acetyl-CoA and pyruvate to citramalyl-CoA, citramalyl-CoA to citramalate, citramalate to citraconate, and citraconate to methyacrylate; aconitate to itaconate, itaconate to itaconyl-CoA, itaconyl-CoA to citramalyl-CoA, citramalyl-CoA to citramalate, citramalate to mesaconate, mesaconate to methacrylate, and so forth such as the reactions described herein. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of a methacrylic acid pathway, such as the pathway described herein. Additionally provided is a methacrylic acid pathway comprising acetoacetyl-CoA thiolase, acetoacetyl-CoA reductase, crotonase, 4-hydroxybutyryl-CoA dehydratase (or crotonyl-CoA hydratase, 4-hydroxy), 4-hydroxybutyryl-CoA mutase, 3-hydroxyisobutyryl-CoA synthetase or 3-hydroxyisobutyryl-CoA hydrolase or 3-hydroxyisobutyryl-CoA transferase, and 3-hydroxyisobutyrate dehydratase. Also provided is a methacrylic acid pathway comprising acetoacetyl-CoA thiolase, acetoacetyl-CoA reductase, crotonase, 4-hydroxybutyryl-CoA dehydratase, 4-hydroxybutyryl-CoA mutase, 3-hydroxyisobutyryl-CoA dehydratase, and methacrylyl-CoA synthetase or methacrylyl-CoA hydrolase or methacrylyl-CoA transferase. The production of MAA is known in the art and can be found, for example, in U.S. application Ser. No. 13/436,811, published as U.S. 2013-0065279A1, which is incorporated herein by reference in its entirety.

In an additional embodiment, the invention provides a non-naturally occurring microbial organism having a caprolactam pathway, wherein the non-naturally occurring microbial organism comprises at least one exogenous nucleic acid encoding an enzyme or protein that converts a substrate to a product selected from the group consisting of adipyl-CoA to adipate, adipyl-CoA to adipate semialdehyde, adipate to adipate semialdehyde, adipate semialdehyde to 6-hydroxyhexanoate, 6-hydroxyhexanoate to 6-hydroxyhexanoyl-CoA, 6-hydroxyhexanoate to 6-hydroxyhexanoyl-phosphate, 6-hydroxyhexanoate to caprolactone, 6-hydroxyhexanoyl-CoA to 6-hydroxyhexanoyl phosphate, 6-hydroxyhexanoyl phosphate to caprolactone, 6-hydroxyhexanoyl-CoA to caprolactone, 4-hydroxybutyryl-CoA to 3-oxo-6-hydroxy hexanoyl-CoA, to 3-oxo-6-hydroxy hexanoyl-CoA to 3,6-dihydroxy hexanoyl-CoA, 3,6-dihydroxy hexanoyl-CoA to 6-hydroxyhex-2-enoyl-CoA, 6-hydroxyhex-2-enoyl-CoA to 6-hydroxyhexanoyl-CoA, 6-hydroxyhexanoyl-CoA to 6-hydroxyhexanoate, cyclohexanon to caprolactone, adipate semialdehyde to cyclohexane-1,2-dione, cyclohexane-1,2-dione to 2-hydroxycyclohexanone, to 2-hydroxycyclohexanone to cyclohexane-1,2-diol, cyclohexane-1,2-diol to cyclohexone, pimeloyl-CoA to 2-ketocyclohexone-1-carboxoyl-CoA, 2-ketocyclohexone-1-carboxoyl-CoA to 2-ketocyclohexane-1-carboxylate, 2-ketocyclohexane-1-carboxylate to cyclohexanone, cyclohexanone to cyclohexanoxime, and cyclohexanoxime to caprolactam. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of a caprolactam pathway.

In some embodiments, the non-naturally occurring microbial organism provided herein having increased NADPH can have an adipate pathway, wherein the microbial organism contains at least one exogenous nucleic acid encoding a polypeptide that converts a substrate to a product selected from succinyl-CoA and acetyl-CoA to 3-oxoadipyl-CoA; 3-oxoadipyl-CoA to 3-hydroxyadipyl-CoA; 3-hydroxyadipyl-CoA to 5-carboxy-2-pentenoyl-CoA; 5-carboxy-2-pentenoyl-CoA to adipyl-CoA; adipyl-CoA to adipate (see, e.g., WO2012/177721, which is incorporated herein in its entirety). Additionally, a non-naturally occurring microbial organism can have an adipate pathway, wherein the microbial organism contains at least one exogenous nucleic acid encoding a polypeptide that converts a substrate to a product selected from succinyl-CoA and acetyl-CoA to 3-oxoadipyl-CoA; 3-oxoadipyl-CoA to 3-oxoadipate; 3-oxoadipate to 3-hydroxyadipate; 3-hydroxyadipate to hexa-2-enedioate (also referred to herein as 5-carboxy-2-pentenoate); hexa-2-enedioate to adipate. Also, a non-naturally occurring microbial organism can have a 6-aminocaproic acid pathway, wherein the microbial organism contains at least one exogenous nucleic acid encoding a polypeptide that converts a substrate to a product selected from adipyl-CoA to adipate semialdehyde; and adipate semialdehyde to 6-aminocaproate. Furthermore, a non-naturally occurring microbial organism can have a caprolactam pathway, wherein the microbial organism contains at least one exogenous nucleic acid encoding a polypeptide that converts a substrate to a product selected from adipyl-CoA to adipate semialdehyde; adipate semialdehyde to 6-aminocaproate; and 6-aminocaproate to caprolactam. Additionally, a non-naturally occurring microbial organism can have an adipate pathway, wherein the microbial organism contains at least one exogenous nucleic acid encoding a polypeptide that converts a substrate to a product selected from alpha-ketoadipate to alpha-ketoadipyl-CoA; alpha-ketoadipyl-CoA to 2-hydroxyadipyl-CoA; 2-hydroxyadipyl-CoA to 5-carboxy-2-pentenoyl-CoA; 5-carboxy-2-pentenoyl-CoA to adipyl-CoA; and adipyl-CoA to adipate. Also, a non-naturally occurring microbial organism can have an adipate pathway, wherein the microbial organism contains at least one exogenous nucleic acid encoding a polypeptide that converts a substrate to a product selected from alpha-ketoadipate to 2-hydroxyadipate; 2-hydroxyadipate to 2-hydroxyadipyl-CoA; 2-hydroxyadipyl-CoA to 5-carboxy-2-pentenoyl-CoA; 5-carboxy-2-pentenoyl-CoA to adipyl-CoA; and adipyl-CoA to adipate.

Additionally, a non-naturally occurring microbial organism can have a 6-aminocaproyl-CoA pathway, wherein the microbial organism contains at least one exogenous nucleic acid encoding a polypeptide that converts a substrate to a product selected from 4-aminobutyryl-CoA and acetyl-CoA to 3-oxo-6-aminohexanoyl-CoA; 3-oxo-6-aminohexanoyl-CoA to 3-hydroxy-6-aminohexanoyl-CoA; 3-hydroxy-6-aminohexanoyl-CoA to 6-aminohex-2-enoyl-CoA; 6-aminohex-2-enoyl-CoA to 6-aminocaproyl-CoA. Additional substrates and products of such a pathway can include 6-aminocaproyl-CoA to 6-aminocaproate; 6-aminocaproyl-CoA to caprolactam; or 6-aminocaproyl-CoA to 6-aminocaproate semialdehyde and 6-aminocaproate semialdehyde to hexamethylenediamine. A non-naturally occurring microbial organism also can have a 6-aminocaproic acid pathway, wherein the microbial organism contains at least one exogenous nucleic acid encoding a polypeptide that converts a substrate to a product selected from 4-aminobutyryl-CoA and acetyl-CoA to 3-oxo-6-aminohexanoyl-CoA; 3-oxo-6-aminohexanoyl-CoA to 3-oxo-6-aminohexanoate; 3-oxo-6-aminohexanoate to 3-hydroxy-6-aminohexanoate; 3-hydroxy-6-aminohexanoate to 6-aminohex-2-enoate; and 6-aminohex-2-enoate to 6-aminocaproate. Additional substrates and products of such a pathway can include 6-aminocaproate to caprolactam or 6-aminocaproate to 6-aminocaproyl-CoA, 6-aminocaproyl-CoA to 6-aminocaproate semialdehyde, and 6-aminocaproate semialdehyde to hexamethylenediamine.

Additionally, a non-naturally occurring microbial organism can have a 6-aminocaproic acid pathway, wherein the microbial organism contains at least one exogenous nucleic acid encoding a polypeptide that converts a substrate to a product selected from pyruvate and succinic semialdehyde to 4-hydroxy-2-oxoheptane-1,7-dioate; 4-hydroxy-2-oxoheptane-1,7-dioate (HODH) to 2-oxohept-4-ene-1,7-dioate (OHED): 2-oxohept-4-ene-1,7-dioate (OHED) to 2-oxoheptane-1,7-dioate (2-OHD); 2-oxoheptane-1,7-dioate (2-OHD) to adipate semialdehyde; and adipate semialdehyde to 6-aminocaproate. A non-naturally occurring microbial organism alternatively can have a 6-aminocaproic acid pathway, wherein the microbial organism contains at least one exogenous nucleic acid encoding a polypeptide that converts a substrate to a product selected from pyruvate and succinic semialdehyde to 4-hydroxy-2-oxoheptane-1,7-dioate; 4-hydroxy-2-oxoheptane-1,7-dioate (HODH) to 2-oxohept-4-ene-1,7-dioate (OHED); 2-oxohept-4-ene-1,7-dioate (OHED) to 6-oxohex-4-enoate (6-OHE): 6-oxohex-4-enoate (6-OHE) to adipate semialdehyde; and adipate semialdehyde to 6-aminocaproate. A non-naturally occurring microbial organism alternatively can have a 6-aminocaproic acid pathway, wherein the microbial organism contains at least one exogenous nucleic acid encoding a polypeptide that converts a substrate to a product selected from pyruvate and succinic semialdehyde to 4-hydroxy-2-oxoheptane-1,7-dioate; 4-hydroxy-2-oxoheptane-1,7-dioate (HODH) to 2-oxohept-4-ene-1,7-dioate (OHED); 2-oxohept-4-ene-1,7-dioate (OHED) to 2-aminohept-4-ene-1,7-dioate (2-AHE); 2-aminohept-4-ene-1,7-dioate (2-AHE) to 2-aminoheptane-1,7-dioate (2-AHD); and 2-aminoheptane-1,7-dioate (2-AHD) to 6-aminocaproate. A non-naturally occurring microbial organism alternatively can have a 6-aminocaproic acid pathway, wherein the microbial organism contains at least one exogenous nucleic acid encoding a polypeptide that converts a substrate to a product selected from pyruvate and succinic semialdehyde to 4-hydroxy-2-oxoheptane-1,7-dioate; 4-hydroxy-2-oxoheptane-1,7-dioate (HODH) to 2-oxohept-4-ene-1,7-dioate (OHED); 2-oxohept-4-ene-1,7-dioate (OHED) to 2-oxoheptane-1,7-dioate (2-OHD); 2-oxoheptane-1,7-dioate (2-OHD) to 2-aminoheptane-1,7-dioate (2-AHD); and 2-aminoheptane-1,7-dioate (2-AHD) to 6-aminocaproate. A non-naturally occurring microbial organism alternatively can have a 6-aminocaproic acid pathway, wherein the microbial organism contains at least one exogenous nucleic acid encoding a polypeptide that converts a substrate to a product selected from pyruvate and succinic semialdehyde to 4-hydroxy-2-oxoheptane-1,7-dioate; 4-hydroxy-2-oxoheptane-1,7-dioate (HODH) to 3-hydroxyadipyl-CoA; 3-hydroxyadipyl-CoA to 2,3-dehydroadipyl-CoA; 2,3-dehydroadipyl-CoA to adipyl-CoA; adipyl-CoA to adipate semialdehyde; and adipate semialdehyde to 6-aminocaproate. A non-naturally occurring microbial organism alternatively can have a 6-aminocaproic acid pathway, wherein the microbial organism contains at least one exogenous nucleic acid encoding a polypeptide that converts a substrate to a product selected from pyruvate and succinic semialdehyde to 4-hydroxy-2-oxoheptane-1,7-dioate; 4-hydroxy-2-oxoheptane-1,7-dioate (HODH) to 2-oxohept-4-ene-1,7-dioate (OHED); 2-oxohept-4-ene-1,7-dioate (OHED) to 2,3-dehydroadipyl-CoA; 2,3-dehydroadipyl-CoA to adipyl-CoA; adipyl-CoA to adipate semialdehyde; and adipate semialdehyde to 6-aminocaproate. A non-naturally occurring microbial organism alternatively can have a 6-aminocaproic acid pathway, wherein the microbial organism contains at least one exogenous nucleic acid encoding a polypeptide that converts a substrate to a product selected from pyruvate and succinic semialdehyde to 4-hydroxy-2-oxoheptane-1,7-dioate; 4-hydroxy-2-oxoheptane-1,7-dioate (HODH) to 2-oxohept-4-ene-1,7-dioate (OHED); 2-oxohept-4-ene-1,7-dioate (OHED) to 2-oxoheptane-1,7-dioate (2-OHD); 2-oxoheptane-1,7-dioate (2-OHD) to adipyl-CoA; adipyl-CoA to adipate semialdehyde; and adipate semialdehyde to 6-aminocaproate.

Additionally, a non-naturally occurring microbial organism can have a 6-aminocaproic acid pathway, wherein the microbial organism contains at least one exogenous nucleic acid encoding a polypeptide that converts a substrate to a product selected from glutamate to glutamyl-CoA; glutamyl-coA to 3-oxo-6-amino-pimeloyl-CoA; 3-oxo-6-amino-pimeloyl-CoA to 3-hydroxy-6-amino-pimeloyl-CoA; 3-hydroxy-6-amino-pimeloyl-CoA to 6-amino-7-carboxy-hept-2-enoyl-CoA; 6-amino-7-carboxy-hept-2-enoyl-CoA to 6-aminopimeloyl-CoA; 6-aminopimeloyl-CoA to 2-aminopimelate; and 2-aminopimelate to 6-aminocaproate. A non-naturally occurring microbial organism alternatively can have a 6-aminocaproic acid pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-aminopimelate; 3-aminopimelate to 2-aminopimelate; and 2-aminopimelate to 6-aminocaproate. A non-naturally occurring microbial organism alternatively can have a 6-aminocaproic acid pathway, wherein the microbial organism contains at least one exogenous nucleic acid encoding a polypeptide that converts a substrate to a product selected from homolysine to 6-aminohexanamide; and 6-aminohexanamide to 6-aminocaproate. A non-naturally occurring microbial organism alternatively can have a 6-aminocaproic acid pathway, wherein the microbial organism contains at least one exogenous nucleic acid encoding a polypeptide that converts a substrate to a product selected from adipate to adipate semialdehyde; adipate to adipylphospate; and adipylphospate to adipate semialdehyde.

Additionally, a non-naturally occurring microbial organism can have a 6-aminocaproic acid pathway, wherein the microbial organism contains at least one exogenous nucleic acid encoding a polypeptide that converts a substrate to a product selected from 2-amino-7-oxosubarate to 2-amino-7-oxoheptanoate; 2-amino-7-oxoheptanoate to 6-aminohexanal; 6-aminohexanal to 6-aminocaproate; 2-amino-7-oxosubarate to 2-amino-7-oxoheptanoate; 2-amino-7-oxoheptanoate to 6-aminohexanal; 2-amino-7-oxoheptanoate to 2-aminopimelate; and 2-aminopimelate to 6-aminocaproate. A non-naturally occurring microbial organism can further have a 2-amino-7-oxosubarate pathway, wherein the microbial organism contains at least one exogenous nucleic acid encoding a polypeptide that converts a substrate to a product selected from glutamate-5-semialdehyde to 2-amino-5-hydroxy-7-oxosubarate; 2-amino-5-hydroxy-7-oxosubarate to 2-amino-5-ene-7-oxosubarate; and 2-amino-5-ene-7-oxosubarate to 2-amino-7-oxosubarate.

Additionally, a non-naturally occurring microbial organism can have an hexamethylenediamine (HMDA) pathway, wherein the microbial organism contains at least one exogenous nucleic acid encoding a polypeptide that converts a substrate to a product selected from 6-aminocaproate to [(6-aminohexanoyl)oxy]phosphonate (6-AHOP); [(6-aminohexanoyl)oxy]phosphonate (6-AHOP) to 6-aminocaproaic semialdehyde; and 6-aminocaproaic semialdehyde to hexamethylenediamine. A non-naturally occurring microbial organism alternatively can have a HMDA pathway, wherein the microbial organism contains at least one exogenous nucleic acid encoding a polypeptide that converts a substrate to a product selected from 6-aminocaproate to [(6-aminohexanoyl)oxy]phosphonate (6-AHOP); [(6-aminohexanoyl)oxy]phosphonate (6-AHOP) to 6-aminocaproyl-CoA; 6-aminocaproyl-CoA to 6-aminocaproaic semialdehyde; and 6-aminocaproaic semialdehyde to hexamethylenediamine. A non-naturally occurring microbial organism alternatively can have a HMDA pathway, wherein the microbial organism contains at least one exogenous nucleic acid encoding a polypeptide that converts a substrate to a product selected from 6-aminocaproate to 6-aminocaproyl-CoA; 6-aminocaproyl-CoA to 6-aminocaproic semialdehyde; and 6-aminocaproic semialdehyde to hexamethylenediamine. A non-naturally occurring microbial organism alternatively can have a HMDA pathway, wherein the microbial organism contains at least one exogenous nucleic acid encoding a polypeptide that converts a substrate to a product selected from 6-aminocaproate to 6-acetamidohexanoate; 6-acetamidohexanoate to [(6-acetamidohexanoy)oxy]phosphonate (6-AAHOP); [(6-acetamidohexanoy)oxy]phosphonate (6-AAHOP) to 6-acetamidohexanal; 6-acetamidohexanal to 6-acetamidohexanamine; and 6-acetamidohexanamine to hexamethylenediamine. A non-naturally occurring microbial organism alternatively can have a HMDA pathway, wherein the microbial organism contains at least one exogenous nucleic acid encoding a polypeptide that converts a substrate to a product selected from 6-aminocaproate to 6-acetamidohexanoate; 6-acetamidohexanoate to 6-acetamidohexanoyl-CoA; 6-acetamidohexanoyl-CoA to 6-acetamidohexanal; 6-acetamidohexanal to 6-acetamidohexanamine; and 6-acetamidohexanamine to hexamethylenediamine. A non-naturally occurring microbial organism alternatively can have a HMDA pathway, wherein the microbial organism contains at least one exogenous nucleic acid encoding a polypeptide that converts a substrate to a product selected from 6-aminocaproate to 6-acetamidohexanoate; 6-acetamidohexanoate to [(6-acetamidohexanoy)oxy]phosphonate (6-AAHOP); [(6-acetamidohexanoy)oxy]phosphonate (6-AAHOP) to 6-acetamidohexanoyl-CoA; 6-acetamidohexanoyl-CoA to 6-acetamidohexanal; 6-acetamidohexanal to 6-acetamidohexanamine; and 6-acetamidohexanamine to hexamethylenediamine.

Additionally, a non-naturally occurring microbial organism can have an hexamethylenediamine (HMDA) pathway, wherein the microbial organism contains at least one exogenous nucleic acid encoding a polypeptide that converts a substrate to a product selected from glutamate to glutamyl-CoA; glutamyl-coA to 3-oxo-6-amino-pimeloyl-CoA; 3-oxo-6-amino-pimeloyl-CoA to 3-hydroxy-6-amino-pimeloyl-CoA; 3-hydroxy-6-amino-pimeloyl-CoA to 6-amino-7-carboxy-hept-2-enoyl-CoA; 6-amino-7-carboxy-hept-2-enoyl-CoA to 6-aminopimeloyl-CoA; 6-aminopimeloyl-CoA to 2-amino-7-oxoheptanoate; -amino-7-oxoheptanoate to homolysine; and homolysine to HMDA. A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-oxo-1-carboxy heptanal; 3-oxo-1-carboxy heptanal to 3-oxo-7-amino heptanoate; 3-oxo-7-amino heptanoate to 3,7-diamino heptanoate; 3,7-diamino heptanoate to homolysine; and homolysine to HMDA. A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 5-oxopimeloyl phosponate; 5-oxopimeloyl phosponate to 3-oxo-1-carboxy heptanal; 3-oxo-1-carboxy heptanal to 3-oxo-7-amino heptanoate; 3-oxo-7-amino heptanoate to 3,7-diamino heptanoate; 3,7-diamino heptanoate to homolysine and homolysine to HMDA. A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 5-oxopimeloyl-CoA; 5-oxopimeloyl-CoA to 3-oxo-1-carboxy heptanal; 3-oxo-1-carboxy heptanal to 3-oxo-7-amino heptanoate; 3-oxo-7-amino heptanoate to 3,7-diamino heptanoate; 3,7-diamino heptanoate to homolysine and homolysine to HMDA. A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-oxo-1-carboxy heptanal; 3-oxo-1-carboxy heptanal to 3-amino-7-oxoheptanoate; 3-amino-7-oxoheptanoate to 3,7-diamino heptanoate; 3,7-diamino heptanoate to homolysine; and homolysine to HMDA. A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 5-oxopimeloyl-CoA; 5-oxopimeloyl-CoA to 3-oxo-1-carboxy heptanal; 3-oxo-1-carboxy heptanal to 3-amino-7-oxoheptanoate; 3-amino-7-oxoheptanoate to 3,7-diamino heptanoate; 3,7-diamino heptanoate to homolysine; and homolysine to HMDA. A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 5-oxopimeloyl phosponate; 5-oxopimeloyl phosponate to 3-oxo-1carboxy heptanal; 3-oxo-1-carboxy heptanal to 3-amino-7-oxoheptanoate; 3-amino-7-oxoheptanoate to 3,7-diamino heptanoate; 3,7-diamino heptanoate to homolysine; and homolysine to HMDA. A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-aminopimelate; 3-aminopimelate to 3-amino-7-oxoheptanoate; 3-amino-7-oxoheptanoate to 2-amino-7-axoheptanoate; 2-amino-7-axoheptanoate to homolysine; and homolysine to HMDA. A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-aminopimelate; 3-aminopimelate to 5-aminopimeloyl phosphonate; 5-aminopimeloyl phosphonate to 3-amino-7-oxoheptanoate; 3-amino-7-oxoheptanoate to 2-amino-7-axoheptanoate; 2-amino-7-axoheptanoate to homolysine; and homolysine to HMDA. A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 5-aminopimeloyl-CoA; 5-aminopimeloyl-CoA to 3-amino-7-oxoheptanoate; 3-amino-7-oxoheptanoate to 2-amino-7-axoheptanoate; 2-amino-7-axoheptanoate to homolysine; and homolysine to HMDA. A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-aminopimelate; 3-aminopimelate to 3-amino-7-oxoheptanoate; 3-amino-7-oxoheptanoate to 3,7-diamino heptanoate; 3,7-diamino heptanoate to homolysine; and homolysine to HMDA. A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-aminopimelate; 3-aminopimelate to 5-aminopimeloyl-CoA; 5-aminopimeloyl-CoA to 3-amino-7-oxoheptanoate; 3-amino-7-oxoheptanoate to 3,7-diamino heptanoate; 3,7-diamino heptanoate to homolysine; and homolysine to HMDA. A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-aminopimelate; 3-aminopimelate to 5-aminopimeloyl phosphonate; 5-aminopimeloyl phosphonate to 3-amino-7-oxoheptanoate; 3-amino-7-oxoheptanoate to 3,7-diamino heptanoate; 3,7-diamino heptanoate to homolysine; and homolysine to HMDA. A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-aminopimelate; 3-aminopimelate to 2-aminopimelate; 2-aminopimelate to 2-amino-7-oxoheptanoate; 2-amino-7-oxoheptanoate to homolysine; and homolysine to HMDA. A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-aminopimelate; 3-aminopimelate to 2-aminopimelate; 2-aminopimelate to 6-aminopimeloylphosphonate; 6-aminopimeloylphosphonate to 2-amino-7-oxoheptanoate; 2-amino-7-oxoheptanoate to homolysine; and homolysine to HMDA. A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-aminopimelate; 3-aminopimelate to 2-aminopimelate; 2-aminopimelate to 6-aminopimeloyl-CoA; 6-aminopimeloyl-CoA to 2-amino-7-oxoheptanoate; 2-amino-7-oxoheptanoate to homolysine; and homolysine to HMDA. A non-naturally occurring microbial organism alternatively can have a HMDA pathway, wherein the microbial organism contains at least one exogenous nucleic acid encoding a polypeptide that converts a substrate to a product selected from pyruvate and 4-aminobutanal to 2-oxo-4-hydroxy 7-aminoheptanoate; 2-oxo-4-hydroxy 7-aminoheptanoate to 2-oxo-7-amino hept-3-enoate; 2-oxo-7-amino hept-3-enoate to 2-oxo-7-amino heptanoate; 2-oxo-7-amino heptanoate to homolysine; and homolysine to HMDA. A non-naturally occurring microbial organism alternatively can have a HMDA pathway, wherein the microbial organism contains at least one exogenous nucleic acid encoding a polypeptide that converts a substrate to a product selected from pyruvate and 4-aminobutanal to 2-oxo-4-hydroxy 7-aminoheptanoate; 2-oxo-4-hydroxy 7-aminoheptanoate to 2-oxo-7-amino hept-3-enoate; 2-oxo-7-amino hept-3-enoate to 2-oxo-7-amino heptanoate; 2-oxo-7-aminoheptanoate to 6-aminohexanal; and 6-aminohexanal to HMDA. A non-naturally occurring microbial organism alternatively can have a HMDA pathway, wherein the microbial organism contains at least one exogenous nucleic acid encoding a polypeptide that converts a substrate to a product selected from 6-aminocaproate to 6-aminocaproic semialdehyde; and 6-aminocaproic semialdehyde to HMDA. A non-naturally occurring microbial organism alternatively can have a HMDA pathway, wherein the microbial organism contains at least one exogenous nucleic acid encoding a polypeptide that converts a substrate to a product selected from 6-aminocaproate to 6-acetamidohexanoate; 6-acetamidohexanoate to 6-acetamidohexanal; 6-acetamidohexanal to 6-acetamidohexanamine; 6-acetamidohexanamine to HMDA. A non-naturally occurring microbial organism alternatively can have a HMDA pathway, wherein the microbial organism contains at least one exogenous nucleic acid encoding a polypeptide that converts a substrate to a product selected from 2-amino-7-oxosubarate to 2-amino-7-oxoheptanoate; 2-amino-7-oxoheptanoate to 6-aminohexanal; 6-aminohexanal to HMDA; 2-amino-7-oxosubarate to 2-oxo-7-aminoheptanoate; 2-amino-7-oxoheptanoate to homolysine; homolysine to HMDA; 2-oxo-7-aminoheptanoate to homolysine; 2-oxo-7-aminoheptanoate to 6-aminohexanal; 2-amino-7-oxosubarate to 2,7-diaminosubarate; and 2,7-diaminosubarate to homolysine. A non-naturally occurring microbial organism can further have a 2-amino-7-oxosubarate pathway, wherein the microbial organism contains at least one exogenous nucleic acid encoding a polypeptide that converts a substrate to a product selected from glutamate-5-semialdehyde to 2-amino-5-hydroxy-7-oxosubarate; 2-amino-5-hydroxy-7-oxosubarate to 2-amino-5-ene-7-oxosubarate; and 2-amino-5-ene-7-oxosubarate to 2-amino-7-oxosubarate.

Figure 6A:
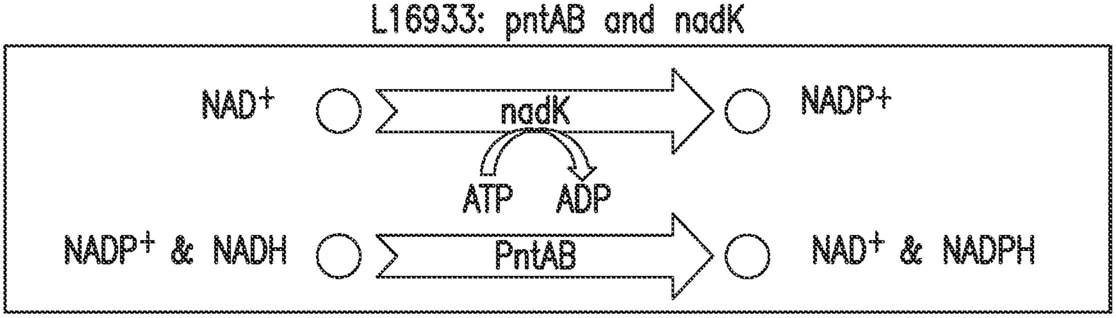
FIG. 6A and FIG. 6B show exemplary reactions for the L16933 strain overexpressing pntAB and nadK (FIG. 6A) and the L17786 strain overexpressing the nadK variant (FIG. 6B).

While generally described herein as a microbial organism that contains an increased availability of NADPH, it is understood that the invention additionally provides a non-naturally occurring microbial organism comprising at least one exogenous nucleic acid encoding an enzyme expressed in a sufficient amount to increase availability of an NADPH intermediate. For example, as disclosed herein, NADPH can be produced by a two step process that is exemplified by the conversion of NAD+ to NADP+ by nadK, and then NADP+ and NADH to NAD+ and NADPH by PntAB (FIG. 6A). In some embodiments, the present invention provides a non-naturally occurring microbial organism comprising at least one exogenous nucleic acid encoding an enzyme expressed in a sufficient amount to increase availability of NADPH, where the microbial organism produces an NADPH intermediate.

It is also understood that the increased availability of NADPH can be used to increase the production of a product, such as 1,3-BDO, (3R)-hydroxybutyl (3R)-hydroxybutyrate, MMA, or amino acids. Accordingly, it is understood that the invention additionally provides in some embodiments a non-naturally occurring microbial organism that includes a 1,3-BDO, (3R)-hydroxybutyl (3R)-hydroxybutyrate, MMA, or amino acid biosynthesis pathway enzyme, wherein the pathway contains at least one NADPH dependent enzyme, and the pathway enzyme is expressed in a sufficient amount to produce an intermediate of a 1,3-BDO, (3R)-hydroxybutyl (3R)-hydroxybutyrate, MMA, or amino acids pathway, or other product intermediate. Therefore, in addition to a microbial organism containing a 1,3-BDO, (3R)-hydroxybutyl (3R)-hydroxybutyrate, MMA, or amino acid biosynthesis pathway that produces 1,3-BDO, (3R)-hydroxybutyl (3R)-hydroxybutyrate, MMA, or amino acid, the invention additionally provides a non-naturally occurring microbial organism, where the microbial organism produces a 1,3-BDO, (3R)-hydroxybutyl (3R)-hydroxybutyrate, MMA, or amino acid biosynthesis pathway intermediate.

It is further understood that the invention additionally provides a non-naturally occurring microbial organism comprising at least one exogenous nucleic acid encoding an enzyme expressed in a sufficient amount to increase availability of an NADPH byproduct. For example, NADPH can be produced by the enzymatic conversion of NADP+ and D-glyceraldehyde 3-phosphate to 3-phospho-D-glycerate and NADPH and 2 molecules of hydrogen by gapN, where 3-phospho-D-glycerate is a NADPH byproduct. Similarly, for example, an ATP-NADH kinase can convert NADH and NAD+ to NADPH and NADP+, where NADP+ is a NADPH byproduct. Accordingly, in some embodiments, the present invention provides a non-naturally occurring microbial organism comprising at least one exogenous nucleic acid encoding an enzyme expressed in a sufficient amount to increase availability of an NADPH byproduct. Therefore, in addition to a microbial organism containing an increased availability of NADPH, the invention additionally provides a non-naturally occurring microbial organism comprising at least one exogenous nucleic acid encoding an enzyme expressed in a sufficient amount to increase availability of an NADPH byproduct.

It is understood that any of the pathways disclosed herein, as described throughout and incorporated by reference in their entirety, can be utilized to generate a non-naturally occurring microbial organism that produces any pathway intermediate or product containing an NADPH dependent enzyme, as desired. As disclosed herein, such a microbial organism that produces an intermediate can be used in combination with another microbial organism expressing downstream pathway enzymes to produce a desired product. However, it is understood that a non-naturally occurring microbial organism that produces a 1,3-BDO, (3R)-hydroxybutyl (3R)-hydroxybutyrate, MMA, or amino acid biosynthesis pathway intermediate can be utilized to produce the intermediate as a desired product.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well-known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

The non-naturally occurring microbial organisms of the invention for increasing the availability of co-factors, such as NADPH, can be produced by introducing expressible nucleic acids encoding one or more of the enzymes or proteins participating in one or more biosynthetic reactions that increase availability of such co-factors, such as NADPH. The non-naturally occurring microbial organisms of the invention can be further produced by introducing expressible nucleic acids encoding one or more of the enzymes or proteins participating in, for example, one or more 1,3-BDO, (3R)-hydroxybutyl (3R)-hydroxybutyrate, MMA, or amino acid biosynthesis pathways. Depending on the host microbial organism chosen for biosynthesis, nucleic acids for some or all of a particular reaction or series of reactions that increase the availability of NADPH for the production of, for example, either 1,3-BDO, (3R)-hydroxybutyl (3R)-hydroxybutyrate, MMA, or amino acid can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve increased availability of NADPH for the production of, for example, either 1,3-BDO, (3R)-hydroxybutyl (3R)-hydroxybutyrate, MMA, or an amino acid. Thus, a non-naturally occurring microbial organism of the invention can be produced by introducing exogenous enzyme or protein activities to obtain a desired reaction or series of reactions. Alternatively, a desired reaction or series of reactions can be obtained by introducing one or more exogenous enzyme or protein activities that, together with one or more endogenous enzymes or proteins, produces a desired product such as increased availability of NADPH for production of, for example, either 1,3-BDO, (3R)-hydroxybutyl (3R)-hydroxybutyrate, MMA, or an amino acid.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae*, and the like. *E. coli* is a particularly useful host organisms since it is a well-characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Depending on the constituents of a selected host microbial organism having increased availability of NADPH for production of, for example, either 1,3-BDO, (3R)-hydroxybutyl (3R)-hydroxybutyrate, MMA, or an amino acid, the non-naturally occurring microbial organisms of the invention will include at least one exogenous nucleic acid encoding an enzyme in a sufficient amount to increase availability of NADPH for the production of, for example, either 1,3-BDO, (3R)-hydroxybutyl (3R)-hydroxybutyrate, MMA, or an amino acid, and up to all encoding nucleic acids, including those for one or more, for example, 1,3-BDO, (3R)-hydroxybutyl (3R)-hydroxybutyrate, MMA, or an amino acid biosynthetic pathways. For example, 1,3-BDO, (3R)-hydroxybutyl (3R)-hydroxybutyrate, MMA, or an amino acid can be established in a host having increased availability of NADPH that is deficient in a pathway enzyme or protein through exogenous expression of the corresponding encoding nucleic acid. In a host deficient in all enzymes or proteins of, for example, a 1,3-BDO, (3R)-hydroxybutyl (3R)-hydroxybutyrate, MMA, or amino acid biosynthesis pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of, for example, 1,3-BDO, (3R)-hydroxybutyl (3R)-hydroxybutyrate, MMA, or an amino acid can be included in a host expressing one or more enzymes or proteins for increased production of NADPH.

Given the teachings and guidance provided herein, those skilled in the art will understand that the number of additional encoding nucleic acids to introduce in an expressible form into a non-naturally occurring microbial organism comprising at least one exogenous nucleic acid encoding an enzyme expressed in a sufficient amount to increase availability of NADPH for the production of, for example, 1,3-BDO, (3R)-hydroxybutyl (3R)-hydroxybutyrate, MMA, or an amino acid, will, at least, parallel the biosynthesis pathway deficiencies of the selected host microbial organism, such as the 1,3-BDO, (3R)-hydroxybutyl (3R)-hydroxybutyrate, MMA, or amino acid biosynthesis pathway deficiencies of the selected host microbial organism. Therefore, a non-naturally occurring microbial organism of the invention can have one, two, three, four, five, six, seven, eight, or up to all nucleic acids encoding the enzymes or proteins constituting a reaction or series of reactions for increased availability of NADPH for the production of, for example, either 1,3-BDO, (3R)-hydroxybutyl (3R)-hydroxybutyrate, MMA, or an amino acid disclosed herein. In some embodiments, the non-naturally occurring microbial organisms also can include other genetic modifications that facilitate or optimize the increased availability of NADPH for the production of, for example, either 1,3-BDO, (3R)-hydroxybutyl (3R)-hydroxybutyrate, MMA, or amino acid biosynthesis, or that confer other useful functions onto the host microbial organism. One such other functionality can include, for example, augmentation of the synthesis of one or more of the precursors required to increase availability of NADPH for the production of, for example, either 1,3-BDO, (3R)-hydroxybutyl (3R)-hydroxybutyrate, MMA, or an amino acid, or one or more of the pathway precursors required to increase availability of, for example, either 1,3-BDO, (3R)-hydroxybutyl (3R)-hydroxybutyrate, MMA, or an amino acid. For example, the precursors can be a precursor for increasing the availability of NADPH, such as NAD+ or NADP+. Alternatively, the precursor can be a pathway precursor for increasing the production of, for example, either 1,3-BDO, (3R)-hydroxybutyl (3R)-hydroxybutyrate, MMA, or an amino acid.

Generally, a host microbial organism is selected such that it produces the precursor for increasing the availability of NADPH, and/or the pathway precursor required to increase availability of a desired product, such as, either 1,3-BDO, (3R)-hydroxybutyl (3R)-hydroxybutyrate, MMA, or an amino acid, either as a naturally produced molecule or as an engineered product that either provides de novo production of a desired precursor or increased production of a precursor naturally produced by the host microbial organism. A host organism can be engineered to increase production of a precursor, as disclosed herein. In addition, a microbial organism that has been engineered to produce a desired precursor can be used as a host organism and further engineered to express enzymes or proteins for increased production of NADPH, as well as, for example, a 1,3-BDO, (3R)-hydroxybutyl (3R)-hydroxybutyrate, MMA, or amino acid biosynthesis pathway.

In some embodiments, a non-naturally occurring microbial organism of the invention is generated from a host that contains the enzymatic capability to increase the availability of NADPH for production of, for example, either 1,3-BDO, (3R)-hydroxybutyl (3R)-hydroxybutyrate, MMA, or an amino acid. In this specific embodiment it can be useful to increase the synthesis or accumulation of NADPH to, for example, drive 1,3-BDO, (3R)-hydroxybutyl (3R)-hydroxybutyrate, MMA, or amino acid biosynthesis pathway reactions toward 1,3-BDO, (3R)-hydroxybutyl (3R)-hydroxybutyrate, MMA, or amino acid production, respectively. Increased synthesis or accumulation can be accomplished by, for example, overexpression of nucleic acids encoding one or more of the enzymes or proteins provided herein for increasing the availability of NADPH. Over expression of the enzyme or enzymes and/or protein or proteins disclosed herein that are capable of increasing the availability of NADPH for production of, for example, 1,3-BDO, (3R)-hydroxybutyl (3R)-hydroxybutyrate, MMA, or an amino acid can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing increased availability of NADPH for production of, for example, 1,3-BDO, (3R)-hydroxybutyl (3R)-hydroxybutyrate, MMA, or an amino acid, through overexpression of one, two, three, four, five, six, seven, or eight, depending on the number of enzymes in the pathway, that is, up to all nucleic acids encoding enzymes or proteins disclosed herein that can increase the availability of NADPH, as well as, for example, 1,3-BDO, (3R)-hydroxybutyl (3R)-hydroxybutyrate, MMA, or amino acid biosynthetic pathway enzymes or proteins. In addition, a non-naturally occurring organism can be generated by mutagenesis of an endogenous gene that results in an increase in activity of an enzyme disclosed herein that can increase the availability of NADPH, as well as, for example, a 1,3-BDO, a (3R)-hydroxybutyl (3R)-hydroxybutyrate, a MMA, or an amino acid biosynthetic pathway enzyme.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments, such as by removing a negative regulatory effector or induction of the gene's promoter when linked to an inducible promoter or other regulatory element. Thus, an endogenous gene having a naturally occurring inducible promoter can be up regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced to confer, for example, one of more enzymes that increase the availability of NADPH. In certain embodiments, the nucleic acids can be introduced so as to confer, for example, a microbial organism with increased availability of NADPH as well as, for example, a 1,3-BDO, (3R)-hydroxybutyl (3R)-hydroxybutyrate, MMA, or an amino acid biosynthetic pathway onto the microbial organism. Alternatively, encoding nucleic acids can be introduced to produce an intermediate microbial organism having the biosynthetic capability to catalyze some of the required reactions to confer, for example, a microbial organism with increased availability of NADPH as well, for example, 1,3-BDO, (3R)-hydroxybutyl (3R)-hydroxybutyrate, MMA, or an amino acid biosynthetic capability. For example, a non-naturally occurring microbial organism having increased availability of NADPH, where the NADPH is used as a co-factor in, for example, a 1,3-BDO, (3R)-hydroxybutyl (3R)-hydroxybutyrate, MMA, or amino acid biosynthesis pathway, can include at least two exogenous nucleic acids encoding desired enzymes or proteins, such as the combination of a an ATP-NADH kinase, and an acetoacetyl-CoA reductase; a NADP-dependent glyceraldehyde-3-phosphate dehydrogenase (gapN), and (3R)-hydroxybutyryl 3-oxobutyrate reductase; and a ATP-NAD+ kinase, and a 3-hydroxybutyraldehyde reductase, and the like. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention, so long as the combination of enzymes and/or proteins of the desired biosynthetic pathway results in production of the corresponding desired product. Similarly, any combination of four or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product. Similarly, any combination of four, five, six, seven, eight, or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of, for example, 1,3-BDO, (3R)-hydroxybutyl (3R)-hydroxybutyrate, MMA, or amino acids as described herein, the non-naturally occurring microbial organisms having increased availability of NADPH and methods of the invention for increasing the availability of NADPH can also be utilized in various combinations with each other and with other microbial organisms and methods well known in the art to achieve product biosynthesis by other routes. For example, one alternative to produce, for example, 1,3-BDO, (3R)-hydroxybutyl (3R)-hydroxybutyrate, MMA, or an amino acid in a non-naturally occurring microbial organism having increased availability of NADPH other than use of the, for example, 1,3-BDO, (3R)-hydroxybutyl (3R)-hydroxybutyrate, MMA, or amino acid producers is through addition of another microbial organism capable of converting, for example, a 1,3-BDO, (3R)-hydroxybutyl (3R)-hydroxybutyrate, MMA, or amino acid biosynthesis pathway intermediate to, for example, 1,3-BDO, (3R)-hydroxybutyl (3R)-hydroxybutyrate, MMA, or an amino acid. One such procedure includes, for example, the fermentation of a microbial organism that produces a 1,3-BDO, (3R)-hydroxybutyl (3R)-hydroxybutyrate, MMA, or amino acid biosynthesis pathway intermediate. The 1,3-BDO, (3R)-hydroxybutyl (3R)-hydroxybutyrate, MMA, or amino acid biosynthesis pathway intermediate can then be used as a substrate for a second non-naturally occurring microbial organism having increased availability of NADPH, as disclosed herein, that converts the 1,3-BDO, (3R)-hydroxybutyl (3R)-hydroxybutyrate, MMA, or amino acid biosynthesis pathway intermediate to 1,3-BDO, (3R)-hydroxybutyl (3R)-hydroxybutyrate, MMA, or an amino acid. The 1,3-BDO, (3R)-hydroxybutyl (3R)-hydroxybutyrate, MMA, or amino acid biosynthesis pathway intermediate can be added directly to another culture of the second non-naturally occurring microbial organism having increased availability of NADPH or the original culture of the 1,3-BDO, (3R)-hydroxybutyl (3R)-hydroxybutyrate, MMA, or amino acid biosynthesis pathway intermediate producers can be depleted of these microbial organisms by, for example, cell separation, and then subsequent addition of the second non-naturally occurring microbial organism having increased availability of NADPH to the fermentation broth can be utilized to produce the final product without intermediate purification steps.

In other embodiments, the non-naturally occurring microbial organisms disclosed herein having increased availability of NADPH and methods of the invention for increasing the availability of NADPH can be assembled in a wide variety of subpathways to achieve biosynthesis of, for example, 1,3-BDO, (3R)-hydroxybutyl (3R)-hydroxybutyrate, MMA, or an amino acid. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of 1,3-BDO, (3R)-hydroxybutyl (3R)-hydroxybutyrate, MMA, or an amino acid, can be accomplished by constructing a microbial organism that contains biosynthetic pathways for conversion of one pathway intermediate to another pathway intermediate or the product, and one or more of the microbial organisms that perform conversion of one pathway intermediate to another pathway intermediate or the product via a NADPH dependent enzyme can be constructed to have increased availability of NADPH, as disclosed herein. Alternatively, 1,3-BDO, (3R)-hydroxybutyl (3R)-hydroxybutyrate, MMA, or an amino acid, can also be biosynthetically produced from one or more microbial organisms having increased availability of NADPH through co-culture or co-fermentation using two organisms in the same vessel, where the first microbial organism produces a MMA pathway intermediate, or a 1,3-BDO pathway intermediate and the second microbial organism converts the intermediate to 1,3-BDO, (3R)-hydroxybutyl (3R)-hydroxybutyrate, MMA, or an amino acid, respectively.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce, for example, 1,3-BDO, (3R)-hydroxybutyl (3R)-hydroxybutyrate, MMA, or an amino acid in a non-naturally occurring organism constructed to have increased availability of NADPH, as disclosed herein.

Similarly, it is understood by those skilled in the art that a host organism can be selected based on desired characteristics for introduction of one or more gene disruptions to increase availability of NADPH for production of, for example, 1,3-BDO, (3R)-hydroxybutyl (3R)-hydroxybutyrate, MMA, or an amino acid. Thus, it is understood that, if a genetic modification is to be introduced into a host organism to disrupt a gene, any homologs, orthologs or paralogs that catalyze similar, yet non-identical metabolic reactions can similarly be disrupted to ensure that a desired metabolic reaction is sufficiently disrupted. Because certain differences exist among metabolic networks between different organisms, those skilled in the art will understand that the actual genes disrupted in a given organism may differ between organisms. However, given the teachings and guidance provided herein, those skilled in the art also will understand that the methods of the invention can be applied to any suitable host microorganism constructed to have increased availability of NADPH, as disclosed herein, to identify the cognate metabolic alterations needed to construct an organism in a species of interest that will increase biosynthesis of, for example, 1,3-BDO, (3R)-hydroxybutyl (3R)-hydroxybutyrate, MMA, or an amino acid. In a particular embodiment, the increased availability of NADPH that enables increased production of, for example, 1,3-BDO, (3R)-hydroxybutyl (3R)-hydroxybutyrate, MMA, or an amino acid couples biosynthesis of 1,3-BDO, (3R)-hydroxybutyl (3R)-hydroxybutyrate, MMA, or an amino acid to growth of the organism, and can obligatorily couple production of, for example, 1,3-BDO, (3R)-hydroxybutyl (3R)-hydroxybutyrate, MMA, or an amino acid to growth of the organism if desired and as disclosed herein.

Sources of encoding nucleic acids for increasing the availability of NADPH, as well as nucleic acids for increasing, for example, a 1,3-BDO, (3R)-hydroxybutyl (3R)-hydroxybutyrate, MMA, or amino acid biosynthesis pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Escherichia fergusonii*, Methanocaldococcus jannaschii, Leptospira interrrogans, Geobacter sulfurreducens, Chloroflexus *aurantiacus*, Roseiflexus sp. RS-1, Chloroflexus aggregans, *Achromobacter* xylosoxydans, Clostrdia species, includingi *Clostridium kluyveri, Clostridium symbiosum, Clostridium acetobutylicum, Clostridium saccharoperbutylacetonicum, Clostridium ljungdahlii, Trichomonas vaginalis* G3, *Trypanosoma brucei, Acidaminococcus fermentans, Fusobacterium* species, including *Fusobacterium nucleatum, Fusobacterium* mortiferum, *Corynebacterium glutamicum, Rattus norvegicus, Homo sapiens, Saccharomyces* species, including *Saccharomyces cerevisiae*, Apsergillus species, including *Aspergillus terreus, Aspergillus oryzae, Aspergillus niger, Gibberella zeae, Pichia stipitis, Mycobacterium* species, including *Mycobacterium smegmatis, Mycobacterium avium*, including subsp. *pratuberculosis, Salinispora arenicola Pseudomonas* species, including *Pseudomonas* sp. CF600, *Pseudomonas putida, Pseudomonas fluorescens, Pseudomonas aeruginosa, Ralstonia* species, including *Ralstonia eutropha, Ralstonia eutropha* IMP134, *Ralstonia eutropha* H16, *Ralstonia pickettii, Lactobacillus plantarum, Klebsiella oxytoca, Bacillus* species, including *Bacillus methanolicus, Bacillus subtilis, Bacillus pumilus, Bacillus megaterium, Pedicoccus pentosaceus*, Chlorofexus species, including Chloroflexus *aurantiacus, Chloroflexus aggregans, Rhodobacter sphaeroides*, Methanocaldococcus jannaschii, Leptospira interrrogans, *Candida maltosa, Salmonella* species, including *Salmonella enterica* serovar *Typhimurium, Shewanella* species, including *Shewanella oneidensis, Shewanella* sp. MR-4, *Alcaligenes faecalis, Geobacillus stearothermophilus, Serratia marcescens, Vibrio cholerae, Eubacterium barkeri, Bacteroides capillosus, Archaeoglobus fulgidus, Archaeoglobus fulgidus, Haloarcula marismortui, Pyrobaculum* aerophilum str. IM2, *Rhizobium* species, including *Rhizobium leguminosarum* as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite activity to increase NADPH availability, along with genes encoding 1,3-BDO, (3R)-hydroxybutyl (3R)-hydroxybutyrate, MMA, or an amino acid biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing increased availability of NADPH for biosynthesis of, for example, 1,3-BDO, (3R)-hydroxybutyl (3R)-hydroxybutyrate, MMA, or an amino acid described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when, for example, an alternative 1,3-BDO, (3R)-hydroxybutyl (3R)-hydroxybutyrate, MMA, or an amino acid biosynthetic pathway exists in an unrelated species, 1,3-BDO, (3R)-hydroxybutyl (3R)-hydroxybutyrate, MMA, or an amino acid biosynthesis can be conferred onto the host species having increased availability of NADPH, as disclosed herein, by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will have increased availability of NADPH and synthesize, for example, 1,3-BDO, (3R)-hydroxybutyl (3R)-hydroxybutyrate, MMA, or an amino acid.

Methods for constructing and testing the expression levels of a non-naturally occurring organism having increased availability of NADPH can be performed, for example, by recombinant and detection methods well known in the art. Similarly, methods for constructing and testing the expression levels of a non-naturally occurring, for example, 1,3-BDO, (3R)-hydroxybutyl (3R)-hydroxybutyrate, MMA, or amino acid producing host with increased availability of NADPH can be performed, for example, by recombinant and detection methods well known in the art. Such methods can be found described in, for example, Sambrook et al., Molecular Cloning: A Laboratory Manual, Third Ed., Cold Spring Harbor Laboratory, New York (2001); and Ausubel et al., Current Protocols in Molecular Biology, John Wiley and Sons, Baltimore, MD (1999).

Exogenous nucleic acid sequences involved in a pathway for increasing the availability of NADPH for production of, for example, 1,3-BDO, (3R)-hydroxybutyl (3R)-hydroxybutyrate, MMA, or an amino acid, can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., J. Biol. Chem. 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more exogenous nucleic acids each encoding an enzyme expressed in a sufficient amount to increase the availability of NADPH as exemplified herein operably linked to expression control sequences functional in the host organism. In some embodiments, an expression vector or vectors can be further constructed to include one or more, for example, 1,3-BDO, (3R)-hydroxybutyl (3R)-hydroxybutyrate, MMA, or amino acid biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

In some embodiments, the present invention provides a method for increasing the availability of NADPH in a non-naturally occurring microbial organism that includes culturing the aforementioned non-naturally occurring microbial organism under conditions and for a sufficient period of time to increase the availability of NADPH. Such culturing can be in a substantially anaerobic culture medium and can include organisms having any number of exogenous nucleic acids as described herein above.

As described above, these cultured organisms having increased availability of NADPH can further have, for example, an 1,3-BDO pathway, a (3R)-hydroxybutyl (3R)-hydroxybutyrate pathway, a MMA pathway, an amino acid biosynthesis pathway, a 3HB-CoA pathway, an adipate pathway, a caprolactam pathway, a 6-ACA pathway, a HMDA pathway, or MAA pathway, or any other functional pathway that utilizes NADPH. Accordingly, in some embodiments, the present invention provides a method for increasing the availability of NADPH in a non-naturally occurring microbial organism, wherein increasing the availability of NADPH yields an increase in 1,3 butanediol (1,3-BDO), methyl methacrylate (MMA), (3R)-hydroxybutyl (3R)-hydroxybutyrate, an amino acid, 3HB-CoA, adipate, caprolactam, 6-ACA, HMDA, or MAA. However, it is understood that the non-naturally occurring microbial organism having increased NADPH can be modified to increase the production of any product that uses NADPH in its production, and the examples provided above are not intended to be limiting.

Also provided herein, is a method of increasing the availability of NADPH in a non-naturally occurring microbial organism thereby increasing the yield of, for example, 1,3-BDO; MMA; (3R)-hydroxybutyl (3R)-hydroxybutyrate; amino acids, such as lysine, threonine, tryptophan, or glutamate; 3HB-CoA; adipate; caprolactam; 6-aminocaproic acid (6-ACA); hexametheylenediamine (HMDA); or methacrylic acid (MAA), via carbohydrate-based carbon feedstock, the method includes culturing the aforementioned non-naturally occurring microbial organism under conditions and for a sufficient period of time to produce a product.

Suitable purification and/or assays to test for the production of NADPH, as well as downstream products, such as for example, 1,3-BDO, (3R)-hydroxybutyl (3R)-hydroxybutyrate, MMA, or amino acids can be performed using well-known methods. Suitable replicates, such as triplicate cultures, can be grown for each engineered strain to be tested. For example, product and byproduct formation in the engineered production host can be monitored. The final product and intermediates, and other organic compounds, can be analyzed by methods, such as HPLC (High Performance Liquid Chromatography), GC-MS (Gas Chromatography-Mass Spectroscopy), and LC-MS (Liquid Chromatography-Mass Spectroscopy), or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., Biotechnol. Bioeng. 90:775-779 (2005)), or other suitable assay and detection methods well known in the art. The individual enzyme or protein activities from the exogenous DNA sequences can also be assayed using methods well known in the art.

The production of compounds whose production utilizes NADPH, such as for example, 1,3-BDO, (3R)-hydroxybutyl (3R)-hydroxybutyrate, MMA, amino acids, 3HB-CoA, adipate, caprolactam, 6-ACA, HMDA, or MAA, can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms having increased availability of NADPH described herein can be cultured to produce and/or secrete the biosynthetic products of the invention. For example, the 1,3-BDO, (3R)-hydroxybutyl (3R)-hydroxybutyrate, MMA, or amino acid producers can be cultured for the biosynthetic production of 1,3-BDO, (3R)-hydroxybutyl (3R)-hydroxybutyrate, MMA, or amino acid.

For the production of, for example, 1,3-BDO, (3R)-hydroxybutyl (3R)-hydroxybutyrate, MMA, or amino acid, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United State publication 2009/0047719, filed Aug. 10, 2007. Fermentations can be performed in a batch, fed-batch or continuous manner, as disclosed herein. In some embodiments, the microbial organisms disclosed herein having increased availability of NADPH will exhibit improved performance under high aerobic conditions.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source that can supply a source of carbon to the non-naturally occurring microorganism. Such sources include, for example, sugars such as glucose, xylose, arabinose, galactose, mannose, fructose, sucrose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention having increased availability of NADPH for the production of, for example, 1,3-BDO, (3R)-hydroxybutyl (3R)-hydroxybutyrate, MMA, or amino acids.

In addition to renewable feedstocks, such as those exemplified above, the microbial organisms of the invention having increased availability of NADPH for the production of, for example, 1,3-BDO, (3R)-hydroxybutyl (3R)-hydroxybutyrate, MMA, or amino acids also can be modified for growth on syngas as its source of carbon. In this specific embodiment, one or more proteins or enzymes are expressed in the 1,3-BDO, (3R)-hydroxybutyl (3R)-hydroxybutyrate, MMA, or amino acid producing organisms having increased availability of NADPH to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, Acetogenesis, pp. 3-60 Chapman and Hall, New York, (1994)). This can be summarized by the following equation:

$$2CO_2+4H_2+n\ ADP+n\ Pi \rightarrow CH_3COOH+2H_2O+n\ ATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions that can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate increased availability of NADPH for the production of 1,3-BDO, (3R)-hydroxybutyl (3R)-hydroxybutyrate, MMA, or amino acid, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Additionally, the reductive (reverse) tricarboxylic acid cycle is and/or hydrogenase activities can also be used for the conversion of CO, $CO_2$ and/or $H_2$ to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, NAD(P)H:ferredoxin oxidoreductase, carbon monoxide dehydrogenase, and hydrogenase. Specifically, the reducing equivalents extracted from CO and/or $H_2$ by carbon monoxide dehydrogenase and hydrogenase are utilized to fix $CO_2$ via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to the 1,3-BDO, (3R)-hydroxybutyl (3R)-hydroxybutyrate, MMA, 3HB-CoA, adipate, caprolactam, 6-ACA, HMDA, or MAA precursors, glyceraldehyde-3-phosphate, phosphoenolpyruvate, and pyruvate, by pyruvate:ferredoxin oxidoreductase and the enzymes of gluconeogenesis. Following the teachings and guidance provided herein for introducing a sufficient number of encoding nucleic acids to generate, for example, a 1,3-BDO pathway, a (3R)-hydroxybutyl (3R)-hydroxybutyrate pathway, a MMA pathway, or an amino acid biosynthesis pathway in an organism constructed to have increased availability of NADPH, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the microbial organisms of the invention such that the modified organism contains the complete reductive TCA pathway will confer syngas utilization ability.

Accordingly, given the teachings and guidance provided herein, those skilled in the art will understand that a non-naturally occurring microbial organism having increased availability of NADPH can be produced that secretes the biosynthesized compounds of the invention when grown on a carbon source, such as a carbohydrate. Such compounds include, for example, 1,3-BDO, (3R)-hydroxybutyl (3R)-hydroxybutyrate, MMA, or amino acids and any of the intermediate metabolites in the 1,3-BDO pathway, the (3R)-hydroxybutyl (3R)-hydroxybutyrate pathway, the MMA pathway, or amino acid biosynthesis pathway. All that is required is to engineer in one or more of the required enzyme or protein activities to achieve biosynthesis of the desired compound or intermediate including, for example, inclusion of some or all of the 1,3-BDO, (3R)-hydroxybutyl (3R)-hydroxybutyrate, MMA, or amino acid biosynthesis pathways. Accordingly, the invention provides a non-naturally occurring microbial organism having increased availability of NADPH that produces and/or secretes 1,3-BDO, (3R)-hydroxybutyl (3R)-hydroxybutyrate, MMA, or amino acids, when grown on a carbohydrate or other carbon source and produces and/or secretes any of the intermediate metabolites shown in the 1,3-BDO, (3R)-hydroxybutyl (3R)-hydroxybutyrate, MMA, or amino acid biosynthesis pathway or 1,3-BDO pathway, respectively, when grown on a carbohydrate or other carbon source. The 1,3-BDO, (3R)-hydroxybutyl (3R)-hydroxybutyrate, MMA, or amino acid producing microbial organisms of the invention can initiate synthesis from an intermediate.

The non-naturally occurring microbial organisms of the invention are constructed using methods well known in the art as exemplified herein to exogenously express at least one nucleic acid encoding an enzyme expressed in a sufficient amount to increase availability of NADPH. In some embodiments, the microbial organisms are further constructed to exogenously express at least one nucleic acid encoding a 1,3-BDO, (3R)-hydroxybutyl (3R)-hydroxybutyrate, MMA, or amino acid biosynthesis pathway enzyme or protein in sufficient amounts to produce 1,3-BDO, (3R)-hydroxybutyl (3R)-hydroxybutyrate, MMA, or an amino acid. It is understood that the microbial organisms of the invention having increased availability of NADPH are cultured under conditions sufficient to produce 1,3-BDO, (3R)-hydroxybutyl (3R)-hydroxybutyrate, MMA, or an amino acid. Following the teachings and guidance provided herein, the non-naturally occurring microbial organisms of the invention having increased availability of NADPH can achieve increased biosynthesis of 1,3-BDO, (3R)-hydroxybutyl (3R)-hydroxybutyrate, MMA, or amino acids resulting in intracellular concentrations between about 0.1-200 mM or more. Generally, the intracellular concentration of 1,3-BDO, (3R)-hydroxybutyl (3R)-hydroxybutyrate, MMA, or amino acids is between about 30-300 mM, particularly between about 50-200 mM and more particularly between about 70-150 mM, including about 70 mM, 80 mM, 90 mM, 100 mM, 110 mM, 120 mM, 130 mM, 140 mM, 150 mM or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic or substantially anaerobic conditions, the 1,3-BDO, (3R)-hydroxybutyl (3R)-hydroxybutyrate, MMA, or amino acid producers having increased availability of NADPH can synthesize, for example, 1,3-BDO, (3R)-hydroxybutyl (3R)-hydroxybutyrate, MMA, or amino acids, respectively, at intracellular concentrations of 5-10 mM or more as well as all other concentrations exemplified herein. It is understood that, even though the above description refers to intracellular concentrations, 1,3-BDO, (3R)-hydroxybutyl (3R)-hydroxybutyrate, MMA, or amino acid producing microbial organisms can produce 1,3-BDO, (3R)-hydroxybutyl (3R)-hydroxybutyrate, MMA, or amino acids, respectively, intracellularly and/or secrete the product into the culture medium.

In addition to the culturing and fermentation conditions disclosed herein, growth conditions for achieving biosynthesis of, for example, 1,3-BDO, (3R)-hydroxybutyl (3R)-hydroxybutyrate, MMA, or amino acids in non-naturally occurring microbial organisms having increased availability of NADPH as disclosed herein can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethyl slfonioproprionate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of, for example, 1,3-BDO, (3R)-hydroxybutyl (3R)-hydroxybutyrate, MMA, or amino acid from a non-naturally occurring microbial organism having increased availability of NADPH includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an N2/$CO_2$ mixture or other suitable non-oxygen gas or gases.

The culture conditions described herein can be scaled up and grown continuously for manufacturing of, for example, 1,3-BDO, (3R)-hydroxybutyl (3R)-hydroxybutyrate, MMA, or amino acids. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of, for example, either 1,3-BDO, (3R)-hydroxybutyl (3R)-hydroxybutyrate, MMA, or amino acid. Generally, and as with non-continuous culture procedures, the continuous and/or near-continuous production of, for example, 1,3-BDO, (3R)-hydroxybutyl (3R)-hydroxybutyrate, MMA, or amino acid will include culturing a non-naturally occurring 1,3-BDO, (3R)-hydroxybutyl (3R)-hydroxybutyrate, MMA, or amino acid producing organism, respectively, of the invention having increased availability of NADPH in sufficient nutrients and medium to sustain and/or nearly sustain growth in an exponential phase. Continuous culture under such conditions can be include, for example, growth for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of, for example, 1,3-BDO, (3R)-hydroxybutyl (3R)-hydroxybutyrate, MMA, or amino acids can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using, for example, the 1,3-BDO, (3R)-hydroxybutyl (3R)-hydroxybutyrate, MMA, or amino acid producers of the invention having increased availability of NADPH for continuous production of substantial quantities of, for example, 1,3-BDO, (3R)-hydroxybutyl (3R)-hydroxybutyrate, MMA, or amino acids, the 1,3-BDO, (3R)-hydroxybutyl (3R)-hydroxybutyrate, MMA, or amino acid producers also can be, for example, simultaneously subjected to chemical synthesis procedures to convert the product to other compounds or the product can be separated from the fermentation culture and sequentially subjected to chemical conversion to convert the product to other compounds, if desired.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 1,3-BDO, (3R)-hydroxybutyl (3R)-hydroxybutyrate, MMA, or amino acid in non-naturally occurring microbial organisms having increased availability of NADPH.

One computational method for identifying and designing metabolic alterations favoring biosynthesis of a desired product is the OptKnock computational framework (Burgard et al., Biotechnol. Bioeng. 84:647-657 (2003)). OptKnock is a metabolic modeling and simulation program that suggests gene deletion or disruption strategies that result in genetically stable microorganisms that overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007, which are incorporated by reference in their entirety.

Another computational method for identifying and designing metabolic alterations favoring biosynthetic production of a product is a SimPheny® metabolic modeling and simulation system. This computational method and system is described in, for example, U.S. publication 2003/0233218, filed Jun. 14, 2002, and in International Patent Application No. PCT/US03/18838, filed Jun. 13, 2003. SimPheny® metabolic modeling and simulation system is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the SimPheny® computational system and OptKnock computational system exemplified above. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., Biotechnol. Prog. 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny® computational system.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny® computational system. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., Biotechnol. Bioeng. 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

As disclosed herein, a nucleic acid encoding a desired activity of an enzyme that increases the production of NADPH can be introduced into a host organism. Similarly, a nucleic acid encoding a desired activity of, for example, an 1,3-BDO, (3R)-hydroxybutyl (3R)-hydroxybutyrate, MMA, or amino acid biosynthesis pathway can be introduced into a host organism. In some cases, it can be desirable to modify the activity of an enzyme that increases the production of NADPH, or, for example, a 1,3-BDO, (3R)-hydroxybutyl (3R)-hydroxybutyrate, MMA, or amino acid biosynthesis pathway enzyme or protein to increase production of, for example, 1,3-BDO, (3R)-hydroxybutyl (3R)-hydroxybutyrate, MMA, or an amino acid, respectively. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, $>10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Otten and Quax. *Biomol.Eng* 22:1-9 (2005); and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity an enzyme that increases the availability of NADPH, or, for example, a 1,3-BDO, (3R)-hydroxybutyl (3R)-hydroxybutyrate, MMA, or amino acid biosynthesis pathway enzyme or protein. Such methods include, but are not limited to EpPCR, which introduces random point mutations by reducing the fidelity of DNA polymerase in PCR reactions (Pritchard et al., *J Theor.Biol.* 234:497-509 (2005)); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., *Nucleic Acids Res.* 32:e145 (2004); and Fujii et al., *Nat. Protoc.* 1:2493-2497 (2006)); DNA or Family Shuffling, which typically involves digestion of two or more variant genes with nucleases such as DNase I or EndoV to generate a pool of random fragments that are reassembled by cycles of annealing and extension in the presence of DNA polymerase to create a library of chimeric genes (Stemmer, *Proc Natl Acad Sci USA* 91:10747-10751 (1994); and Stemmer, *Nature* 370:389-391 (1994)); Staggered Extension (StEP), which entails template priming followed by repeated cycles of 2 step PCR with denaturation and very short duration of annealing/extension (as short as 5 sec) (Zhao et al., *Nat. Biotechnol.* 16:258-261 (1998)); Random Priming Recombination (RPR), in which random sequence primers are used to generate many short DNA fragments complementary to different segments of the template (Shao et al., *Nucleic Acids Res* 26:681-683 (1998)).

Additional methods include Heteroduplex Recombination, in which linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)); Random Chimeragenesis on Transient Templates (RACHITT), which employs DNase I fragmentation and size fractionation of single stranded DNA (ssDNA) (Coco et al., *Nat. Biotechnol.* 19:354-359 (2001)); Recombined Extension on Truncated templates (RETT), which entails template switching of unidirectionally growing strands from primers in the presence of unidirectional ssDNA fragments used as a pool of templates (Lee et al., *J. Molec. Catalysis* 26:119-129 (2003)); Degenerate Oligonucleotide Gene Shuffling (DOGS), in which degenerate primers are used to control recombination between molecules; (Bergquist and Gibbs, Methods Mol.Biol 352:191-204 (2007); Bergquist et al., *Biomol.Eng* 22:63-72 (2005); Gibbs et al., *Gene* 271:13-20 (2001)); Incremental Truncation for the Creation of Hybrid Enzymes (ITCHY), which creates a combinatorial library with 1 base pair deletions of a gene or gene fragment of interest (Ostermeier et al., *Proc. Natl. Acad. Sci. USA* 96:3562-3567 (1999); and Ostermeier et al., *Nat. Biotechnol.* 17:1205-1209 (1999)); Thio-Incremental Truncation for the Creation of Hybrid Enzymes (THIO-ITCHY), which is similar to ITCHY except that phosphothioate dNTPs are used to generate truncations (Lutz et al., *Nucleic Acids Res* 29:E16 (2001)); SCRATCHY, which combines two methods for recombining genes, ITCHY and DNA shuffling (Lutz et al., *Proc. Natl. Acad. Sci. USA* 98:11248-11253 (2001)); Random Drift Mutagenesis (RNDM), in which mutations made via epPCR are followed by screening/selection for those retaining usable activity (Bergquist et al., *Biomol. Eng.* 22:63-72 (2005)); Sequence Saturation Mutagenesis (SeSaM), a random mutagenesis method that generates a pool of random length fragments using random incorporation of a phosphothioate nucleotide and cleavage, which is used as a template to extend in the presence of "universal" bases such as inosine, and replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)); Synthetic Shuffling, which uses overlapping oligonucleotides designed to encode "all genetic diversity in targets" and allows a very high diversity for the shuffled progeny (Ness et al., *Nat. Biotechnol.* 20:1251-1255 (2002)); Nucleotide Exchange and Excision Technology NexT, which exploits a combination of dUTP incorporation followed by treatment with uracil DNA glycosylase and then piperidine to perform endpoint DNA fragmentation (Muller et al., *Nucleic Acids Res.* 33:e117 (2005)).

Further methods include Sequence Homology-Independent Protein Recombination (SHIPREC), in which a linker is used to facilitate fusion between two distantly related or unrelated genes, and a range of chimeras is generated between the two genes, resulting in libraries of single-crossover hybrids (Sieber et al., *Nat. Biotechnol.* 19:456-460 (2001)); Gene Site Saturation Mutagenesis™ (GSSM™), in which the starting materials include a supercoiled double stranded DNA (dsDNA) plasmid containing an insert and two primers which are degenerate at the desired site of mutations (Kretz et al., *Methods Enzymol.* 388:3-11 (2004)); Combinatorial Cassette Mutagenesis (CCM), which involves the use of short oligonucleotide cassettes to replace limited regions with a large number of possible amino acid sequence alterations (Reidhaar-Olson et al. *Methods Enzymol.* 208:564-586 (1991); and Reidhaar-Olson et al. *Science* 241:53-57 (1988)); Combinatorial Multiple Cassette Mutagenesis (CMCM), which is essentially similar to CCM and uses epPCR at high mutation rate to identify hot spots and hot regions and then extension by CMCM to cover a defined region of protein sequence space (Reetz et al., *Angew. Chem. Int. Ed Engl.* 40:3589-3591 (2001)); the Mutator Strains technique, in which conditional is mutator plasmids, utilizing the mutD5 gene, which encodes a mutant subunit of DNA polymerase III, to allow increases of 20 to 4000-X in random and natural mutation frequency during selection and block accumulation of deleterious mutations when selection is not required (Selifonova et al., *Appl. Environ. Microbiol.* 67:3645-3649 (2001)); Low et al., *J. Mol. Biol.* 260:359-3680 (1996)).

Additional exemplary methods include Look-Through Mutagenesis (LTM), which is a multidimensional mutagenesis method that assesses and optimizes combinatorial mutations of selected amino acids (Rajpal et al., *Proc. Natl. Acad. Sci. USA* 102:8466-8471 (2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation), in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., *Proc. Natl. Acad. Sci. USA* 99:15926-15931 (2002)); and Iterative Saturation Mutagenesis (ISM), which involves using knowledge of structure/function to choose a likely site for enzyme improvement, performing saturation mutagenesis at chosen site using a mutagenesis method such as Stratagene QuikChange (Stratagene; San Diego CA), screening/selecting for desired properties, and, using improved clone(s), starting over at another site and continue repeating until a desired activity is achieved (Reetz et al., *Nat. Protoc.* 2:891-903 (2007); and Reetz et al., *Angew. Chem. Int. Ed Engl.* 45:7745-7751 (2006)).

Any of the aforementioned methods for mutagenesis can be used alone or in any combination. Additionally, any one or combination of the directed evolution methods can be used in conjunction with adaptive evolution techniques, as described herein.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

EXAMPLES

Example I

Microaerobic Process Decreased NADPH Levels and Ratio Compared to Anaerobic Processes or BDO Production Strain Under Microaerobic Processes The following example demonstrates that microaerobic processes decreased the levels and ratio of NADPH compared to anaerobic, and a BDO production strain under microaerobic processes.

For the production of 1,3-BDO, strains of *Escherichia coli* (*E. coli*) bacteria were cultured in a medium with carbon source and other essential nutrients. The strains were grown using a BDO producing strain, anaerobic, or microaerobic conditions. Anaerobic conditions were produced by first sparging the medium with nitrogen and then sealing the flasks with a septum and crimp-cap. Microaerobic conditions were established by initially flushing capped anaerobic bottles with nitrogen for 5 min, then piercing the septum with a 23G needle (BectonDickenson) after inoculation. The needle was kept in the bottle during growth to allow a small amount of air to enter. Strains were grown under the respective conditions to produce 1,3-butanediol (1,3-BDO), and the levels of nicotinamide adenine dinucleotide (NAD), reduced nicotinamide adenine dinucleotide (NADH), nicotinamide adenine dinucleotide phosphate (NADP), reduced nicotinamide adenine dinucleotide phosphate (NADPH), total NADP[H], and total NAD[H], as well as the ratios of NADH/NAD and NADPH/NADP were measured.

As shown in FIG. 1, there was a significant drop in the NADPH levels and the ratio of NADPH/NADP in the microaerobic process compared to the other conditions. Alcohol dehydrogenase (ADH) and aldehyde dehydrogenase (ALD) are key enzymes involved in the conversion of 3-hydroxybutyryl-coenzyme A (3HB-CoA) to 1,3-BDO and rely on NADPH. These results indicated that increased availability of NADPH can increase the production of 1,3-BDO.

Example II

NadK and PntAB Overexpression Improved Titer, Rate, and Yield of 1,3-Butanediol The following example demonstrates that strains expressing NAD(P) transhydrogenase subunit alpha part 2 (pntAB) and NAD kinase (nadK) significantly improved the titrate, rate, and yield of 1,3-butandiol production (1,3-BDO).

ECh-10228 *E. coli* strains, with or without plasmids expressing nadK and pntAB were cultured under microaerobic conditions. Briefly, twenty-milliliter bottle cultivations for metabolite production or bioconversion were performed in M9 minimal salts medium (6.78 g/L $Na_2HPO_4$, 3.0 g/L $KH_2PO_4$, 0.5 g/L NaCl, 1.0 g/L $NH_4Cl$, 1 mM $MgSO_4$, 0.1 mM $CaCl_2$))) supplemented with 10 mM $NaHCO_3$, 20 g/L D-glucose and 100 mM MOPS to improve the buffering capacity, 10 μg/ml thiamine and the appropriate antibiotics for plasmid maintenance. Microaerobic conditions were used for all strains, which we established by initially flushing capped anaerobic bottles with nitrogen for 5 min, then piercing the septum with a 23G needle (Becton Dickenson) after inoculation. The needle was kept in the bottle during growth to allow a small amount of air to enter. All cultures were grown at 35° C. Fermentations were performed with 11 initial culture volume in 2-1 Biostat B+ bioreactors (Sartorius-Stedim Biotech® bioreactor) using modified M9 minimal medium (6.78 g/l $Na_2HPO_4$, 3.0 g/l $KH_2PO_4$, 0.5 g/L NaCl, 2.0 g/L $NH_4Cl$, 1.0 g/L $(NH_4)_2SO_4$, 1 mM $MgSO_4$, 0.1 mM $CaCl_2$))) supplemented with 20 g/L D-glucose. The temperature was held at 35° C., and the pH was held at 6.95 using 2 M $NH_4OH$ (aerobic phase) or $Na_2CO_3$ (microaerobic phase). The agitation rate was set at 700 r.p.m. Concentrated glucose was fed in to maintain the glucose concentration in the vessel between 0.5 and 5.0 g/L.

The expression of nadK and pntAB using the expression plasmids was confirmed. As shown in Table 2, the plasmid expression of both pntAB and nadK were greater than the respective wild-type (wt) expression levels, and the pntAB plasmid expression was similar or higher than chromosomal overexpression levels. This demonstrated that the overexpression of pntAB and nadK using plasmids could provide a substantial increase in expression, relative to wild-type levels.

TABLE 2

| Protein | ECh-10228 (no plasmid) | ECh-10228 (p115-nadK-p115-pntAB) | 1,3-BDO production strain |
|---|---|---|---|
| PntAB | 0.08 | 1.13 | 0.67 |
| NadK | 0.02 | 1.98 | 0.03 |

Figure 2:
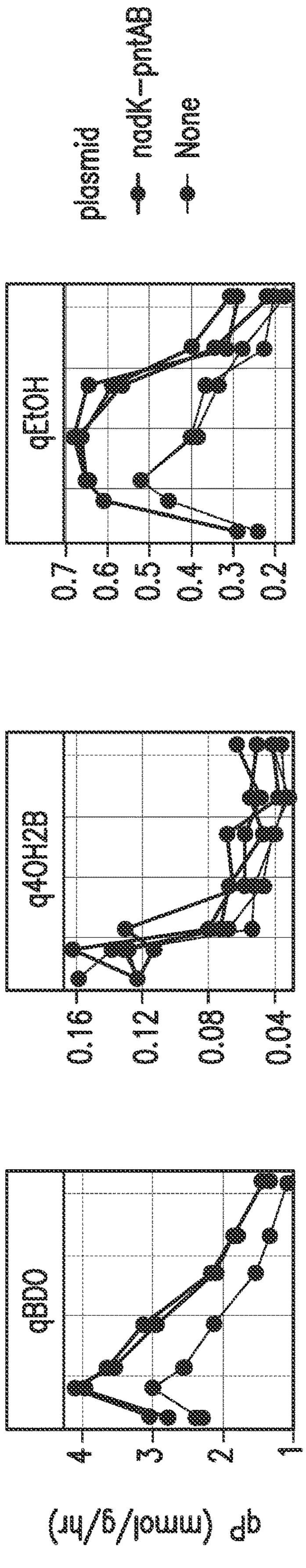
FIG. 2 shows the fermentation results for the specific rate products from the L16182 strain (p115-nadK-p115-pntAB) compared to the L15863 stain (no plasmid). The L16182 strain generated significantly higher specific rates for 1,3-BDO and ethanol, as well as higher 4-hydroxy-2-butanone (4OH2B), and glucose with pntAB-nadK overexpression.

The strains were cultured for 50 hours and the titer, rate, and yield of 1,3-BDO was measured. Strains expressing pntAB and nadK significantly improved 1,3-BDO titer, rate, and yield at low oxygen transfer rate (OTR) conditions (FIG. 1). In addition, overexpression of pntAB and nadK yielded significantly higher specific rates of 1,3-BDO and ethanol (FIG. 2). Higher specific rates of 4-hydroxy-2-butanone (4OH2B) and glucose were also observed after overexpression of pntAB and nadK (FIG. 2). Furthermore, the specific rate of ethanol was maintained longer than the specific rate of 1,3-BDO (FIG. 2). These results demonstrated that overexpression of pntAB and nadK could increase the rate of 1,3-BDO production.

Figure 3:
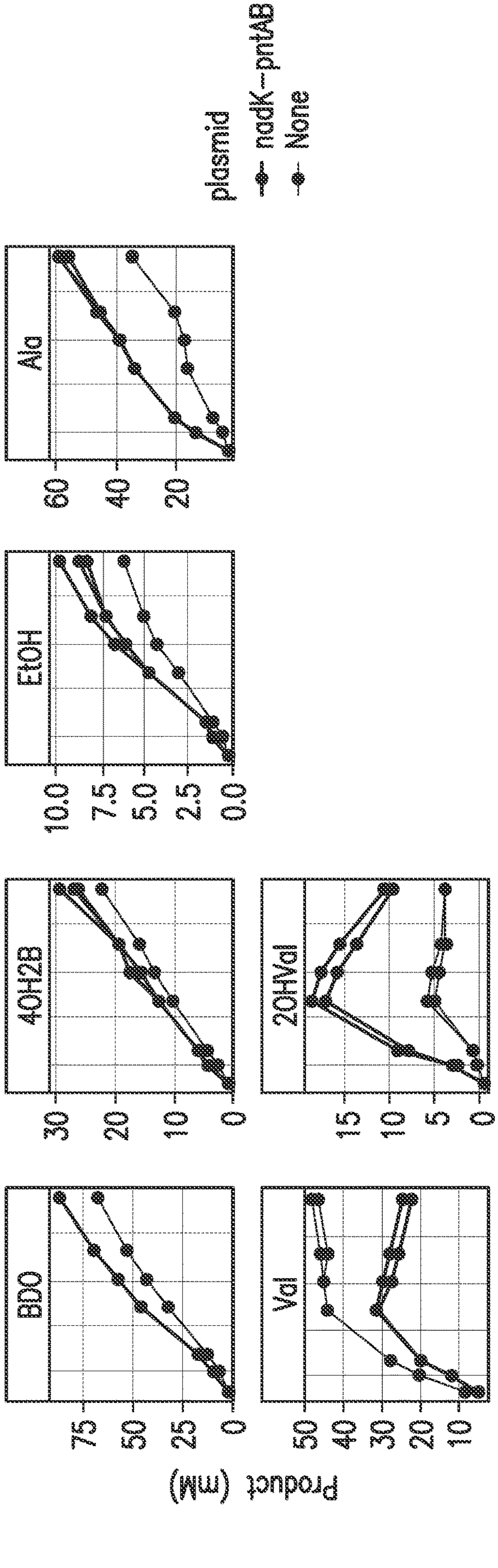
FIG. 3 shows the fermentation results for the concentration of products generated from the L16182 strain (p115-nadK-p115-pntAB) compared to the L15863 stain (no plasmid). The L16182 strain exhibited different pyruvate dynamics, lower C3 byproducts (20H-valerate, valine).

Measurement of the product concentration demonstrated that overexpression of pntAB and nadK produced greater concentrations of 1,3-BDO, ethanol, and the amino acid alanine (FIG. 3). The results also demonstrated different pyruvate dynamics. For example, pntAB and nadK overexpression resulted in lower C3 byproducts, such as valine and 2-hydroxy-valerate (FIG. 3). Furthermore, there was a 4-fold reduction in acetate in the L16182 strain (p115-nadK-p115-pntAB) that overexpressed pntAB and nadK relative to the L15863 host. of acetate in the L16182 strain (p115-nadK-p115-pntAB) compared to the L15863 host. A 4-fold reduction in acetate was observed in the L16182 strain. Taken together, these results demonstrated that pntAB and nadK overexpression increased the titer of 1,3-BDO, as well as ethanol and alanine.

The carbon distribution analysis for the L16182 strain comprised of the ECh-10228 host culture overexpressing nadK and pntAB indicated five key byproducts accounting for more than 10% yield loss. Specifically, ethanol accounted for 4.8%, 3-hydroxybutyrate accounted for 2.1%, 4-hydroxy-2-butanone accounted for 1.3%, alanine accounted for 1.5%, and valine accounted for 1.2%.

In addition, the strain to stain differences of the percent total carbon consumption were determined. Comparison of the L16182 strain comprising the ECh-10228 host with overexpression of pntAB and nadK to the L15863 strain showed a 6.8% increase in 1,3-BDO production. Further, there was approximately a 5% decrease in biomass, a 2% decrease in pyruvate and alanine, and a 1.4% decrease in acetate. Comparison of the L16182 strain comprised of the ECh-10228 host with overexpression of pntAB and nadK, relative to the L15863 host comprised of the ECh-10228 host without overexpression of pntAB and nadK, revealed that there was a 2.1% decrease in biomass, a 2.4% decrease in valine and 2-hydroxy-valerate, and a 0.5% decrease in 3-hydroxybutyrate, pyruvate and lactate in the host overexpressing pntAB and nadK.

Figure 4:
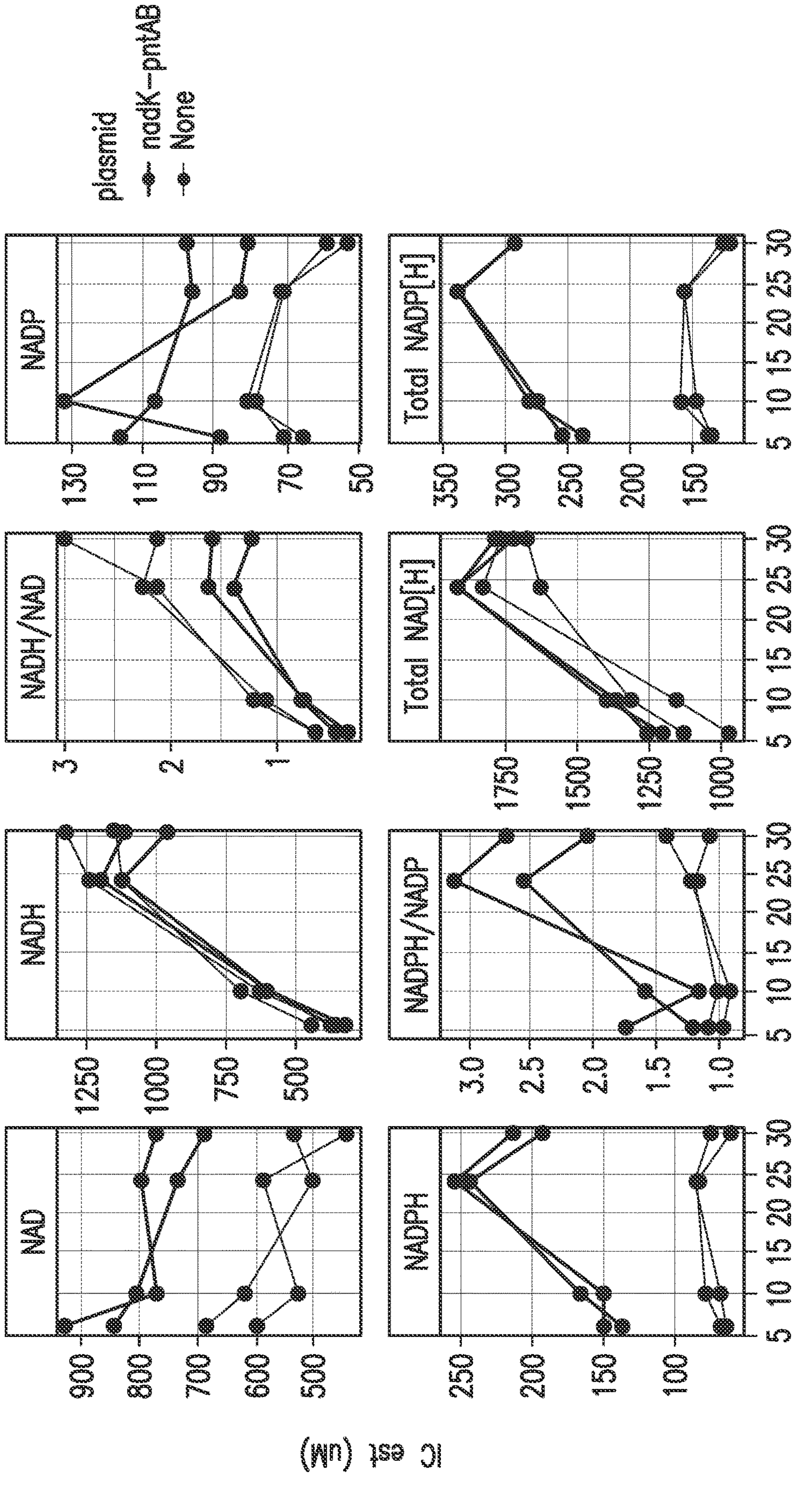
FIG. 4 shows the metabolomics results for the L15863 strain (no plasmid) and the L16182 strain (p115-nadK-p115-pntAB). The L16182 strain yielded a higher concentration of NADPH, and total NADPH, as well as a higher ratio of NADPH/NADP. The increase in total NADPH did not affect the NADH pool.

Next, metabolomics were measured at 6, 10, 24, and 30 hours. The metabolomic results demonstrated that the L16182 strain that overexpressed nadK and pntAB in the ECh-10228 host yielded a higher concentration of total NADPH, as well as a higher ratio of NADPH/NADP (FIG. 4). These redox trends were consistent with pntAB and nadK overexpression in the ECh-9838 host. Importantly, a two fold increase in NADPH pool did not significantly alter the NADH pool (FIG. 4).

Figure 5:
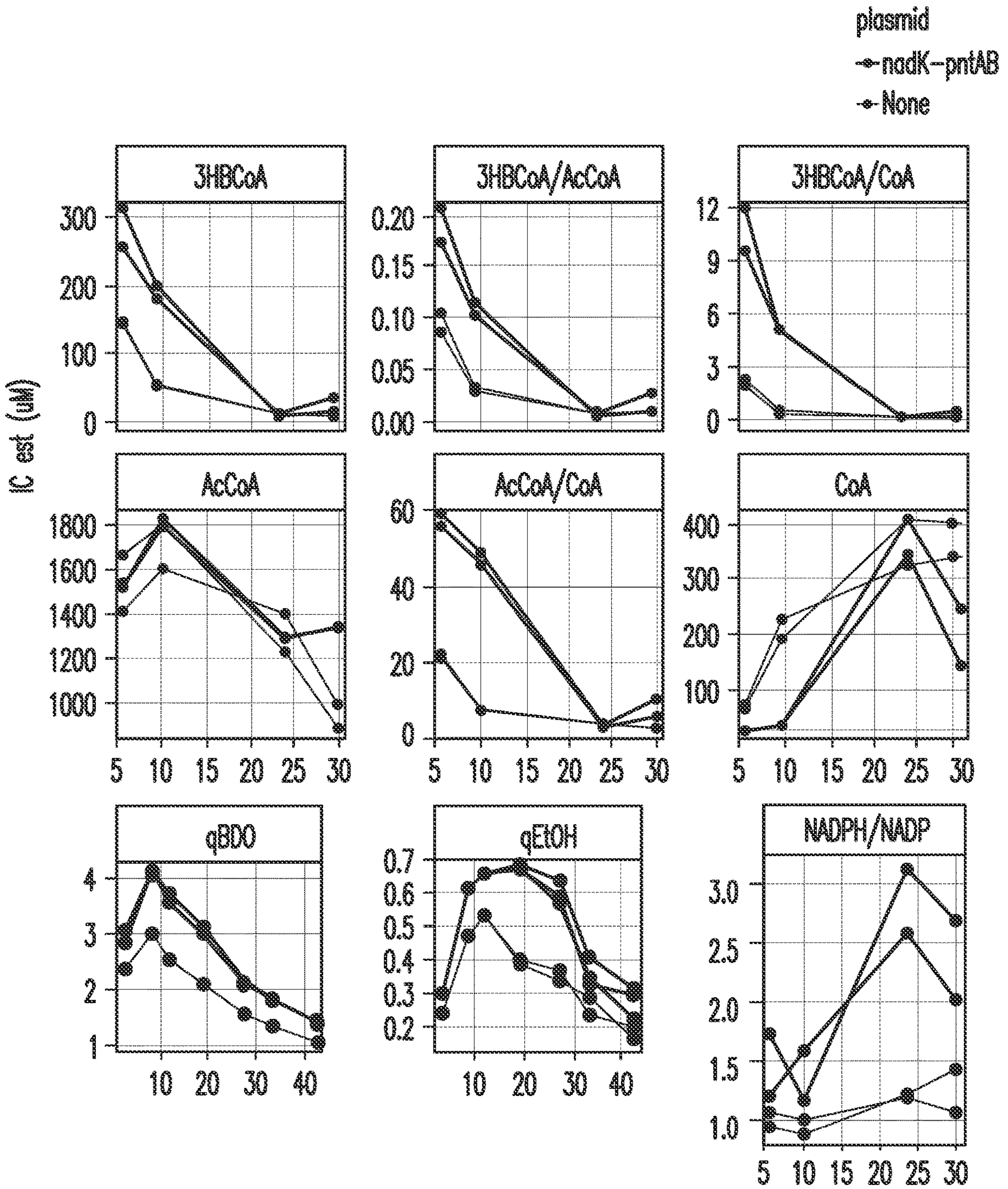
FIG. 5 shows pathway and CoA metabolites for the L15863 strain (no plasmid) and the L16182 strain (p115-nadK-p115-pntAB) measured from 5-48 hours. After 6-10 hours the L16182 strain had 2-3 fold higher concentration of 3HB-CoA, and higher ratios of 3HB-CoA/CoA, and AcCoA/CoA, which was coincident with peak specific rate of BDO and pyruvate levels. By 24-30 hours the L16182 strain had low concentration of 3HB-CoA and low ratio of AcCoA/CoA. After 30-48 hours the L16182 strain had lower specific rates of 1,3-BDO, EtOH, and pyruvate formate-lyase (PFL) flux. 3-hydroxybutyryl coenzyme A (3HB-CoA), acetyl coenzyme A (AcCoA), 1,3-butanediol (BDO), and Ethanol (EtOH).

Measurement of 1,3-BDO pathway and CoA metabolites revealed that after 6-10 hours there was a 2-3 fold higher concentration of 3-hydroxybutyryl-coenzyme A (3HB-CoA), as well as similar increases in the ratio of 3HB-CoA/CoA, and Acetyl-CoA/CoA in strains that overexpressed pntAB and nadK. These increases coincided with peak specific rate of 1,3-BDO and pyruvate reconsumption (FIG. 5). After 24-30 hours the concentration of 3HB-CoA, and the Acetyl-CoA/CoA ratios were low (FIG. 5). After 30-48 hours lower specific rates of 1,3-BDO, ethanol, and pyruvate formate-lyase (PFL) flux were observed (FIG. 5). Taken together, these results indicated that 3HB-CoA availability may contribute to a decrease in the specific rate of 1,3-BDO production. Furthermore, the lower Acetyl-CoA/CoA ratio during the later time period indicated why the specific rate of 1,3-BDO drops while the specific rate of ethanol is maintained.

Comparison of the L16182 strain that overexpressed nadK and pntAB relative to the L15863 strain demonstrated that the overexpression of nadK and pntAB led to a lower 3HB-CoA concentration, as well as lower ratios of 3HB-CoA/CoA, and Acetyl-CoA/CoA. Further, the levels of the byproduct 3HB-CoA in the host that overexpressed nadK and pntAB were even lower than the strain grown in anaerobic conditions. Measurement of CoA levels in the host that overexpressed nadK and pntAB showed that CoA levels were comparable to those produced under anaerobic conditions. The results further demonstrated that pntAB-nadK overexpression yielded lower pentose phosphate intermediates, which was consistent with lower flux through the pentose phosphate pathway.

Collectively, these results demonstrated that nadK-PntAB overexpression significantly increased the ratio of NADPH/NADP and the NADP[H] pool size, without negatively impacting NADH levels. In addition, the overexpression of pntAB and nadK under microaerobic conditions restored the ratio of NADPH/NADP to the levels observed under anaerobic conditions. Importantly, the overexpression of pntAB and nadK also increased the titer, rate, and yield of 1,3-BDO.

Example III

Mutation of nadK Directly Converts NADH into NADPH and Increased Reduced Cofactor Availability, and 1,3-BDO Production The following example demonstrates that strains expressing a nadK variant (ATP-NADH kinase) that directly converts NADH into NADPH increased reduced cofactor availability, and 1,3-BDO production.

Figure 6B:
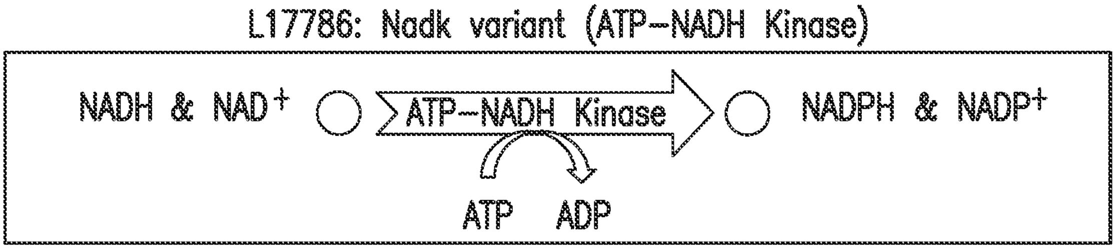
Figure 7:
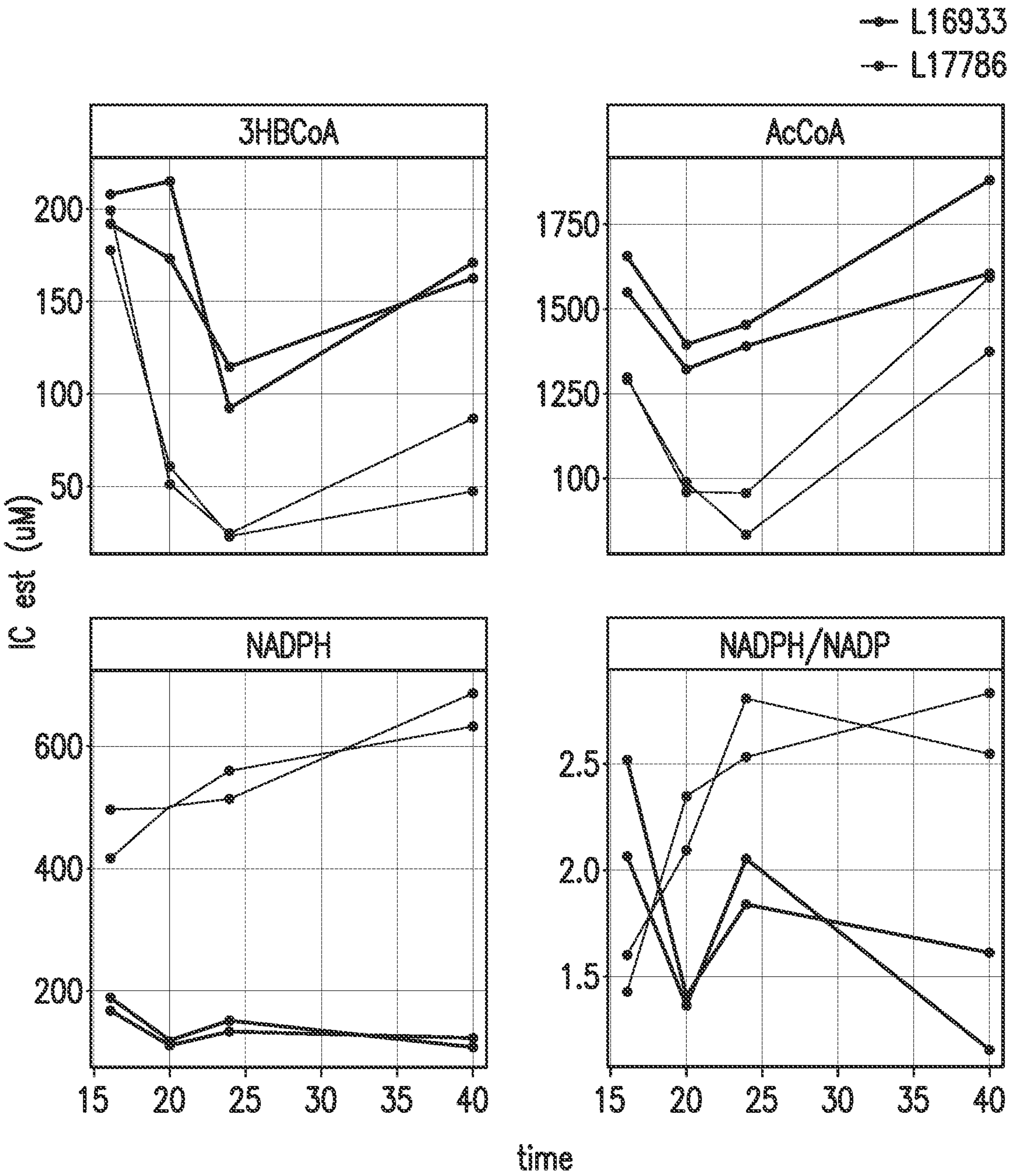
FIG. 7 shows measurement of pathway and CoA metabolites in the L16933 strain overexpressing pntAB and nadK and the L17786 strain overexpressing the nadK variant. Decrease in 3-hydroxybutyryl coenzyme A (3HB-CoA), and acetyl coenzyme A (AcCoA), and higher NAD(P)H and NAD(P)H/NAD(P) ratios was observed in the L17786 strain.

To determine whether a nadK variant that directly convert NADH into NADPH rather than as a two-step process that involves nadK and PntAB, the strain L16933 (nadK and pntAB), was compared to the strain L17786 (overexpressed the nadK variant) (FIG. 6B). When the two strains were grown as described above under high aeration conditions the strain that overexpressed the nadK variant produced higher NAD(P)H levels and had a higher ratio of NAD(P)H/NAD(P) (FIG. 7). Further, the L17786 strain that overexpressed the nadK variant had a decrease in 3HB-CoA and acetyl-CoA accumulation due to better redox in the later phase, which led to a better 1,3-BDO flux (FIG. 7).

Figure 8A:
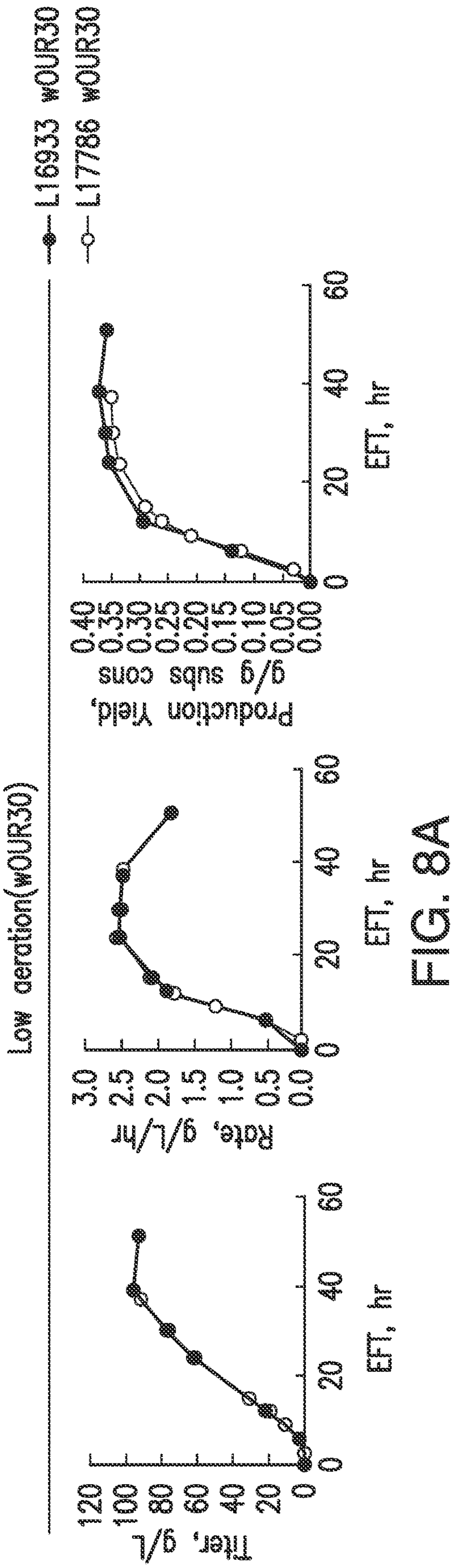
FIG. 8A and FIG. 8B show the effects of low aeration (wOUR30) (FIG. 8A) compared to high aeration (wOUR40) (FIG. 8B) conditions on the production of 1,3-butanediol (1,3-BDO) for the L16933 strain overexpressing pntAB and nadK and the L17786 strain overexpressing the nadK variant. The L17786 strain showed improved performance under high aeration conditions.
Figure 8B:
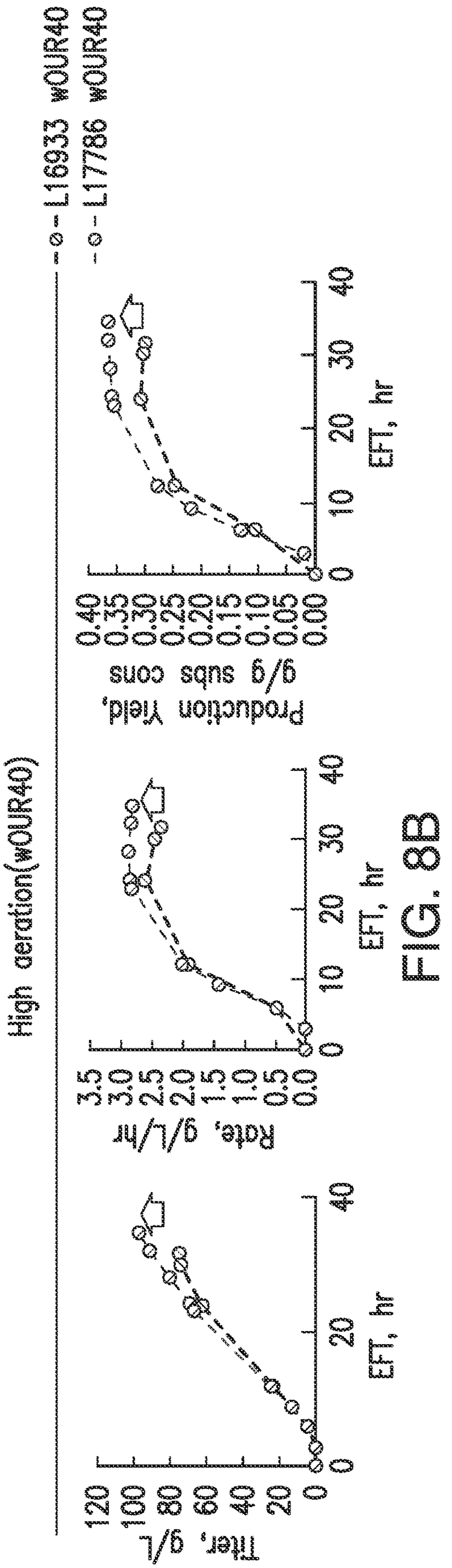
Figure 9A:
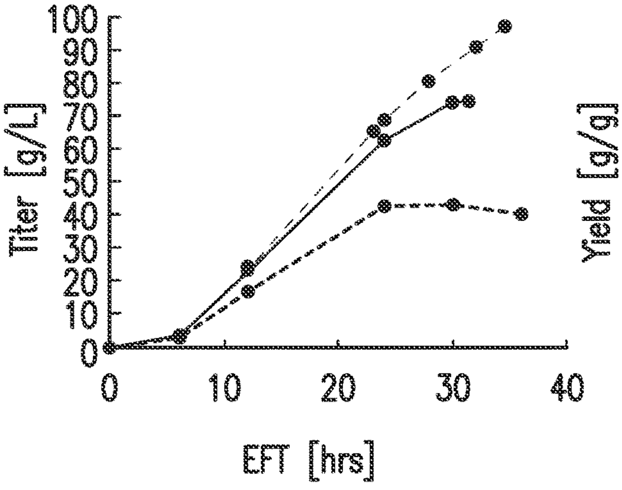
FIG. 9A-FIG. 9D show comparison of 1,3-butanediol (1,3-BDO) titer (FIG. 9A), yield (FIG. 9B), rate (FIG. 9C) and specific rate (FIG. 9D) for the L15086 strain, the L16933 strain overexpressing pntAB and nadK, and the L17786 strain overexpressing the nadK variant under high aerobic conditions. The L17786 strain had greater titer, rate, yield, and specific rate than both the L16933 strain and the L15086 strain.
Figure 9B:
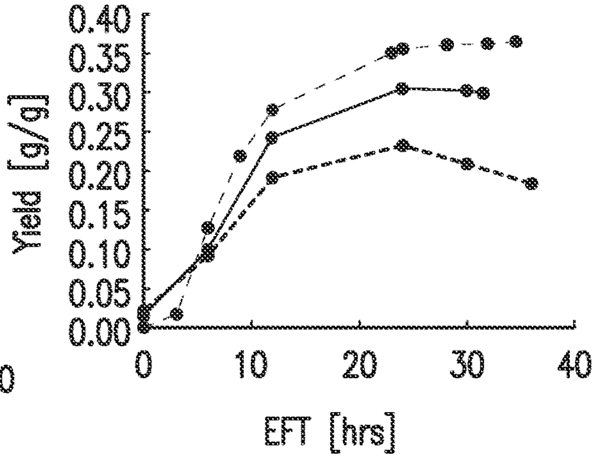
Figure 9C:
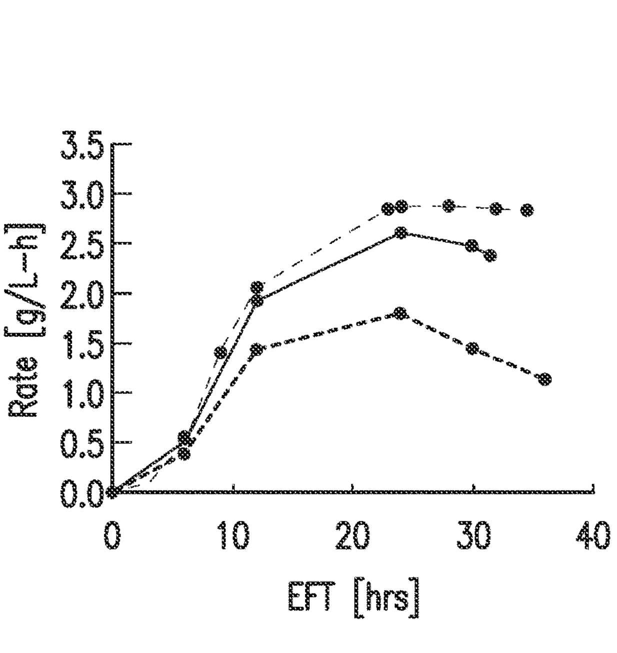
Figure 9D:
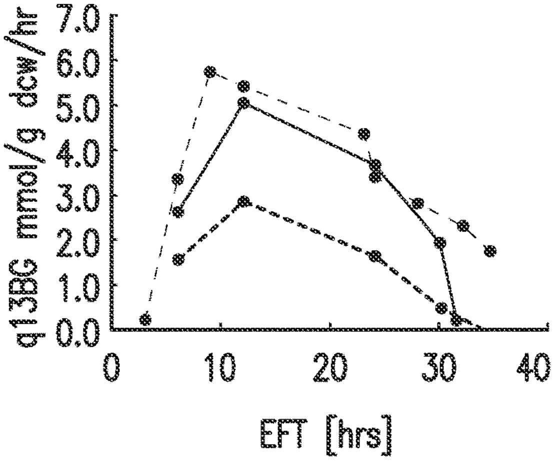
Figure 10A:
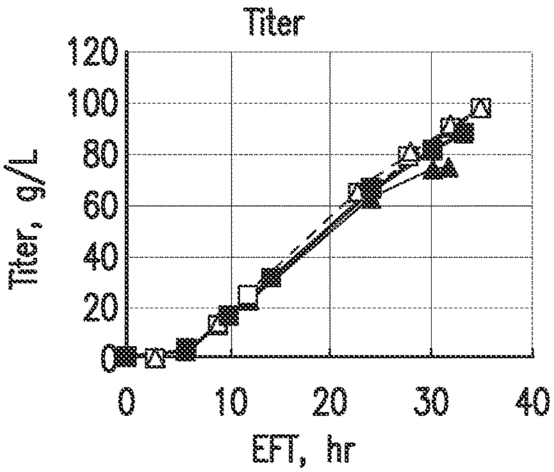
FIG. 10A-FIG. 10D show the titer (FIG. 10A), rate (FIG. 10B), production yield (FIG. 10C), and specific rate (FIG. 10D) of 1,3-butanediol (1,3-BDO) in the L16933 strain overexpressing pntAB and nadK, and the L17786 strain overexpressing the nadK variant under medium and high aerobic conditions. The 1,3-BDO yield was the higher in the L17786 strain under high aerobic conditions.
Figure 10B:
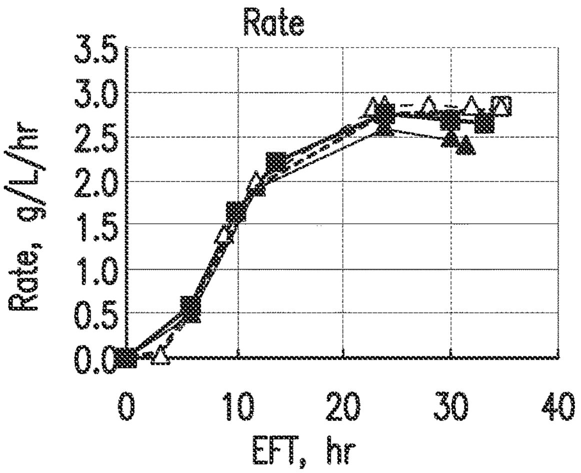
Figure 10C:
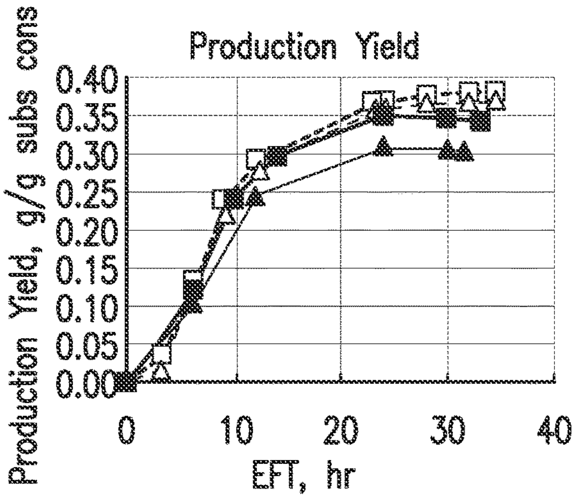
Figure 10D:
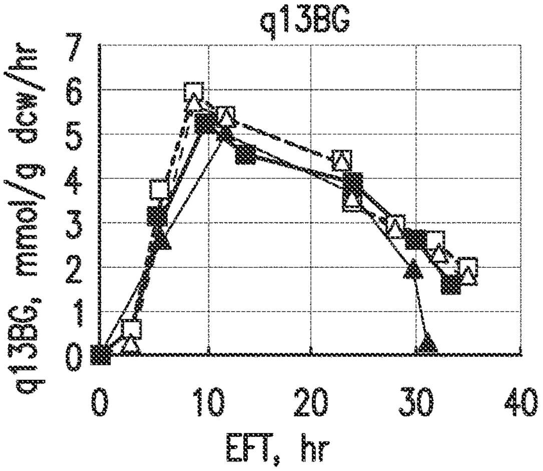
Figure 11:
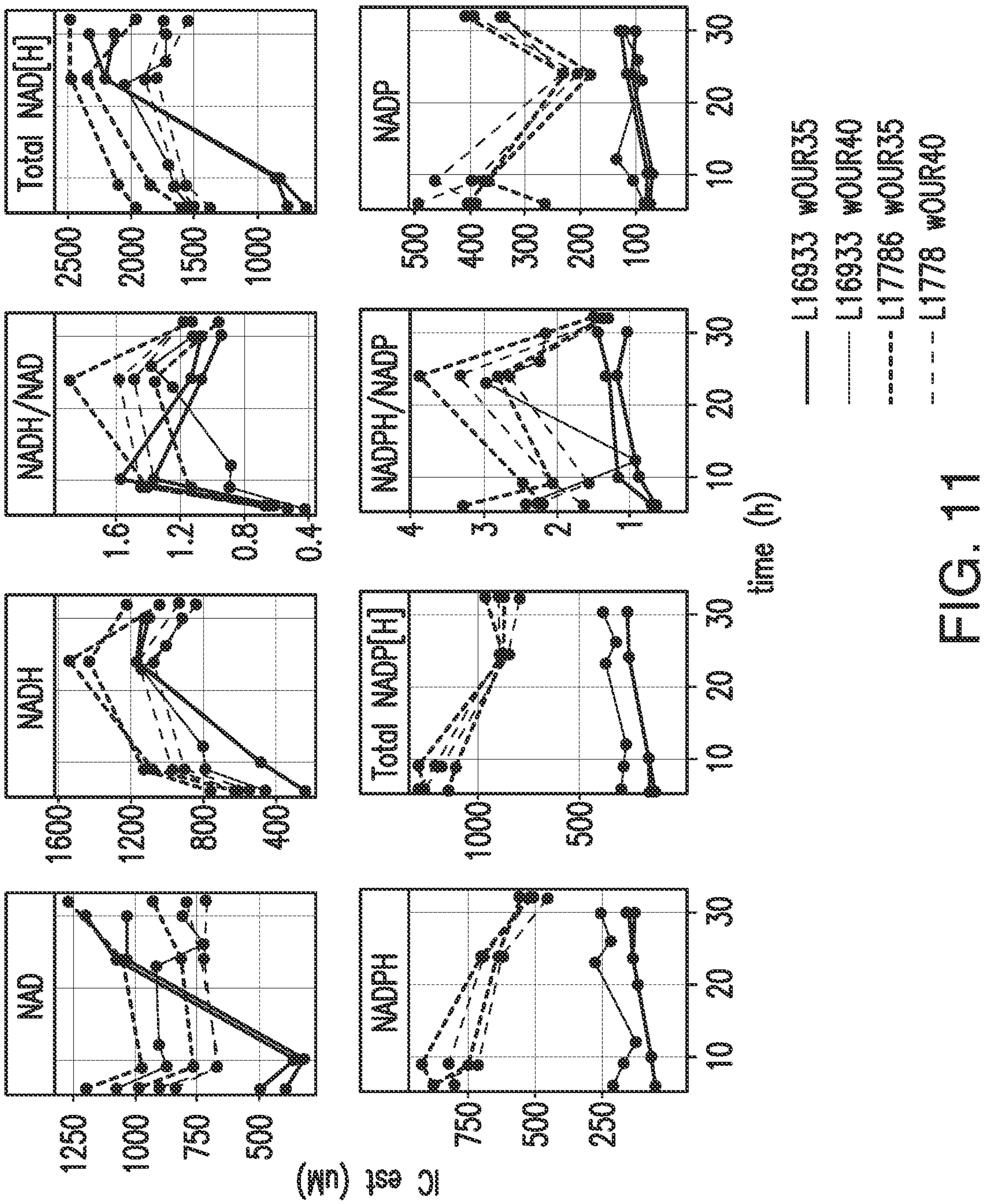
FIG. 11 shows redox metabolite levels for the L16933 strain overexpressing pntAB and nadK, and the L17786 strain overexpressing the nadK variant under medium and high aerobic conditions. The L17786 strain had significantly higher NADPH levels compared to the L16933 strain. The NADH levels were significantly higher in the L16933 strain under medium aerobic conditions.
Figure 12:
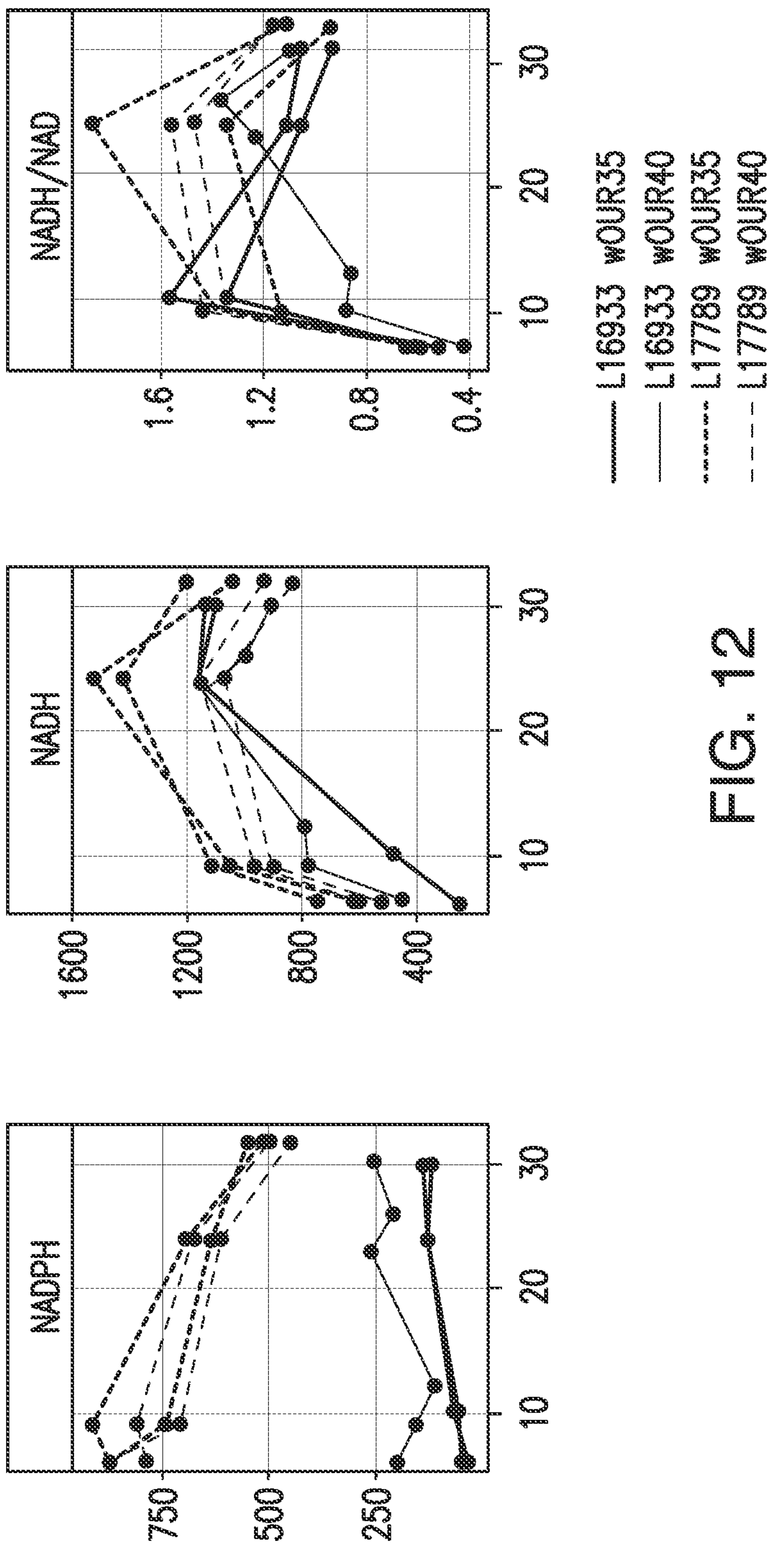
FIG. 12 shows coenzyme-A (CoA) metabolite levels for the L16933 strain overexpressing pntAB and nadK, and the L17786 strain overexpressing the nadK variant under medium and high aerobic conditions. The L17786 strain exhibited a decrease in 3HB-CoA accumulation, whereas 3HB-CoA levels were high at late fermentation for the L16933 strain. The NADH levels were significantly higher in the L16933 strain under medium aerobic conditions. 3-hydroxybutyryl coenzyme A (3HB-CoA), acetyl coenzyme A (AcCoA).

Next, the effects of aeration on 1,3-BDO production in these two strains was monitored. When the two strains were grown under low aeration conditions there was little to no difference in the titer, rate, or production yield of 1,3-BDO production (FIG. 8A and FIG. 8B). However, when the strains were grown under high aeration conditions the L17786 strain that overexpressed the nadK variant displayed a higher titer, a greater rate, and increased production of 1,3-BDO, as compared to the strain L16933 that overexpressed nadK and pntAB. These results demonstrated that the nadK variant was able to perform better under high aeration conditions.

TABLE 3

| Strains (Final Time point) | Yield [g/g] | Titer [g/L] | Rate [g/L/h] |
|---|---|---|---|
| L15086 | 0.182 | 39.6 | 1.10 |
| L16933 | 0.299 | 74.2 | 2.36 |

TABLE 3-continued

| Strains (Final Time point) | Yield [g/g] | Titer [g/L] | Rate [g/L/h] |
|---|---|---|---|
| L17786 - high aeration | 0.365 | 97.1 | 2.81 |

The improvement in 1,3-BDO production was further confirmed by comparing the titer, yield, rate, and specific rate of 1,3-BDO in the L15086 strain, the L16933 (pntAB and nadK) strain, and the L17786 (nadK variant) strain. Consistent with the results described above, the L17786 strain that overexpressed the nadK variant displayed a higher titer, higher yield, greater rate, and specific rate of 1,3-BDO, as compared to the L16933 strain that overexpressed nadK and pntAB (FIG. 9A-FIG. 9D). Furthermore, both strains displayed higher titers, greater rates, increased yield, and greater specific rate production of 1,3-BDO, relative to the L15086 strain (FIG. 9A-FIG. 9D). Quantification of the 1,3-BDO titer, rate, and yield for L16933 (pntAB and nadK) strain relative to the L15086 strain, revealed that the L16933 strain had approximately a 2 fold higher titer, 2 fold higher rate, and 1.5 higher yield. Quantification of the 1,3-BDO titer, rate, and yield for the L17786 (nadK variant) strain relative to the L15086 strain, revealed that the L17786 strain had approximately a 2.5 fold higher titer, 2.5 fold higher rate, and 2.0 higher yield. Furthermore, quantification of the 1,3-BDO titer, rate, and yield for the L17786 (nadK variant) strain relative to the L16933 (pntAB and nadK) strain, revealed that the L17786 strain had approximately a 1.25 fold higher titer, 1.25 fold higher rate, and 1.25 higher yield.

Quantification of the % C-distribution revealed that most of the improvement in 1,3-BDO production is a direct effect of reduction in pyruvate, as well as pyruvate derived byproducts and TCA products. There was no significant difference in the fraction of carbon distributed into the pathway products 1,3-BDO, 3-hydroxybutyrate (3HB), or 4-hydroxy-2-butanone (4OH2B), or the C2 products acetate or ethanol. The effective decrease in biomass led to an increase in the specific rate of 1,3-BDO.

Comparison between either the L16933 (pntAB and nadK) strain or the L17786 (nadK variant) strain relative to the L15086 strain revealed that most of the improvement in 1,3-BDO was a direct effect of reduction in pyruvate and pyruvate derived byproduct, as well as TCA products. There was no significant difference in the fraction of carbon distributed into pathway product and C2. Further, the decrease in biomass led to an increase in the specific rate of 1,3-BDO production.

Consistent with the reduction in pyruvate, the L17786 (nadK variant) strain had lower concentrations of pyruvate and glutamate relative to both the L16933 strain and the L15086 strain. In addition, the biomass was reduced relative to the L15086 strain.

The ability to perform under high aeration was improved in the L17786 (nadK variant) strain and resulted in a significant improvement in the titer, rate, and yield of 1,3-BDO. Measurement of the byproducts of the L17786 (nadK variant) strain revealed that 3-hydroxybutyrate (3HB) and alanine remain the major byproducts under the high aeration conditions. Taken together, these results demonstrated that the L17786 (nadK variant) strain exhibited improvements in 1,3-BDO rate, titer, and yield. Furthermore, the nadK variant strain was able to produce higher NAD(P)H levels and a higher ratio of NAD(P)H/NAD(P), which helped to increase the 1,3-BDO pathway flux. In addition, the nadK variant strain showed improved performance under high aeration.

Example IV

NadK Variant Expressing Strain Exhibited Improved 1,3-BDO Titer, Rate, and Yield Next, the performance of the L16933 strain (nadK and pntAB) was compared to the L17786 strain (nadK variant) under medium aeration and high aeration conditions. The strains were cultured for more than 30 hours and the titer, rate, production yield, and specific rate of 1,3-BDO was continuously measured (FIG. 10A-FIG. 10D). The results indicated that the L17786 strain exhibited an improvement in the titrate, rate, and yield of 1,3-BDO under both aeration conditions, relative to the L16933 strain (Table 4). In addition, it was observed that the 1,3-BDO yield was the highest at medium aeration with the L17786 strain. Importantly, the results demonstrated that there was a significant drop in the titer, rate, production yield, and specific rate of 1,3-BDO for the L16933 strain at high aeration, whereas the L17786 strain had higher titer and higher rate under high aeration conditions.

TABLE 4

| Strains | Yield [g/g] | Titer [g/L] | Rate [g/L/h] |
|---|---|---|---|
| L16933 - medium aeration | 0.339 | 87.6 | 2.64 |
| L16933 - high aeration | 0.299 | 74.2 | 2.36 |
| L17786 - medium aeration | 0.378 | 96.5 | 2.78 |
| L17786 - high aeration | 0.365 | 97.1 | 2.81 |

Comparison of the carbon distribution between the L17786 and L16933 strains under medium aeration or high aeration conditions revealed that the L17786 strain outperformed the L16933 strain under both conditions. Furthermore, higher accumulation of pyruvate and TCA metabolites were observed in the L16933 strain, compared to the L17786 strain.

Comparison of the carbon distribution for L16933 between the medium aeration and high aeration conditions revealed that there was a steep performance drop in the L16933 strain under higher aeration conditions. In contrast, the carbon distribution for L17786 between the medium aeration and high aeration conditions revealed that the L17786 strain is more robust and less sensitive to higher aeration.

The byproduct profile revealed that there was reduced byproduct accumulation with the L17786 strain. Specifically, the L17786 strain displayed lower concentrations of alanine, pyruvate, glutamate, formate, lactate, and acetate, relative to the L16933 strain. However, a steady increase in alanine throughout the microaerobic fermentation was observed despite the pyruvate profile.

The conditions for 1,3-BDO production, and associated byproducts were further analyzed. During the first 12 hours there was an increased flux of 1,3-BDO, 4-hydroxy-2-butanone (4OH2B), C2 byproducts, and redox for both strains under high aeration conditions, relative to the later time points (12h to end) (Table 5). Comparison of the products and byproducts produced during the first 12 hours indicated that the L17786 strain increased 3-hydroxybutyrate (3HB) pathway byproduct, relative to the L16933 strain (Table 5). Pyruvate, C2, and 4OH2B pathway byproducts exhibited reduced flux in the later stages for the L17786 strain, relative to the L16933 strain (Table 5).

TABLE 5

| Condition | Pyr byprod. | C2 byprod. | 1,3-BDO | 4OH2B | 3HB | Redox |
|---|---|---|---|---|---|---|
| L17786 vs L16933 (high aeration) | −56% | −19% | +18% | −40% | +30% | +280% |
| L17786 vs L16933 (high aeration) 0-12 h | −26% | −7% | +15% | −20% | +69% | +150% |
| L17786 vs L16933 (high aeration) 12 h-end | −71% | −23% | +18% | −43% | +15% | +130% |
| L17786 (high aeration) vs L17786 (low aeration) | +13% | −1% | no change | +10% | +13% | −35% |
| L17786 (high aeration) 0-12 hrs vs 12 h-end | −320% | +23% | +20% | +50% | −95% | +80% |
| L16933 (high aeration) 0-12 hrs vs 12 h-EOF | −64% | +41% | +20% | +64% | −32% | +190% |

Pyruvate (pyr); Acetate and ethanol (C2 byprod.); 1,3-butanediol (1,3-BDO); 4-hydroxy-2-butanone (4OH2B); 3-hydroxybutyrate (3HB).

Taken together, these results indicate that the L17786 exhibits improved performance relative to the L16933 strain. In particular, the L17786 strain performs better at high aeration, whereas the L16933 strain exhibited a steep drop in performance at higher aeration conditions.

Example V

Flux Modeling

Figure 13:
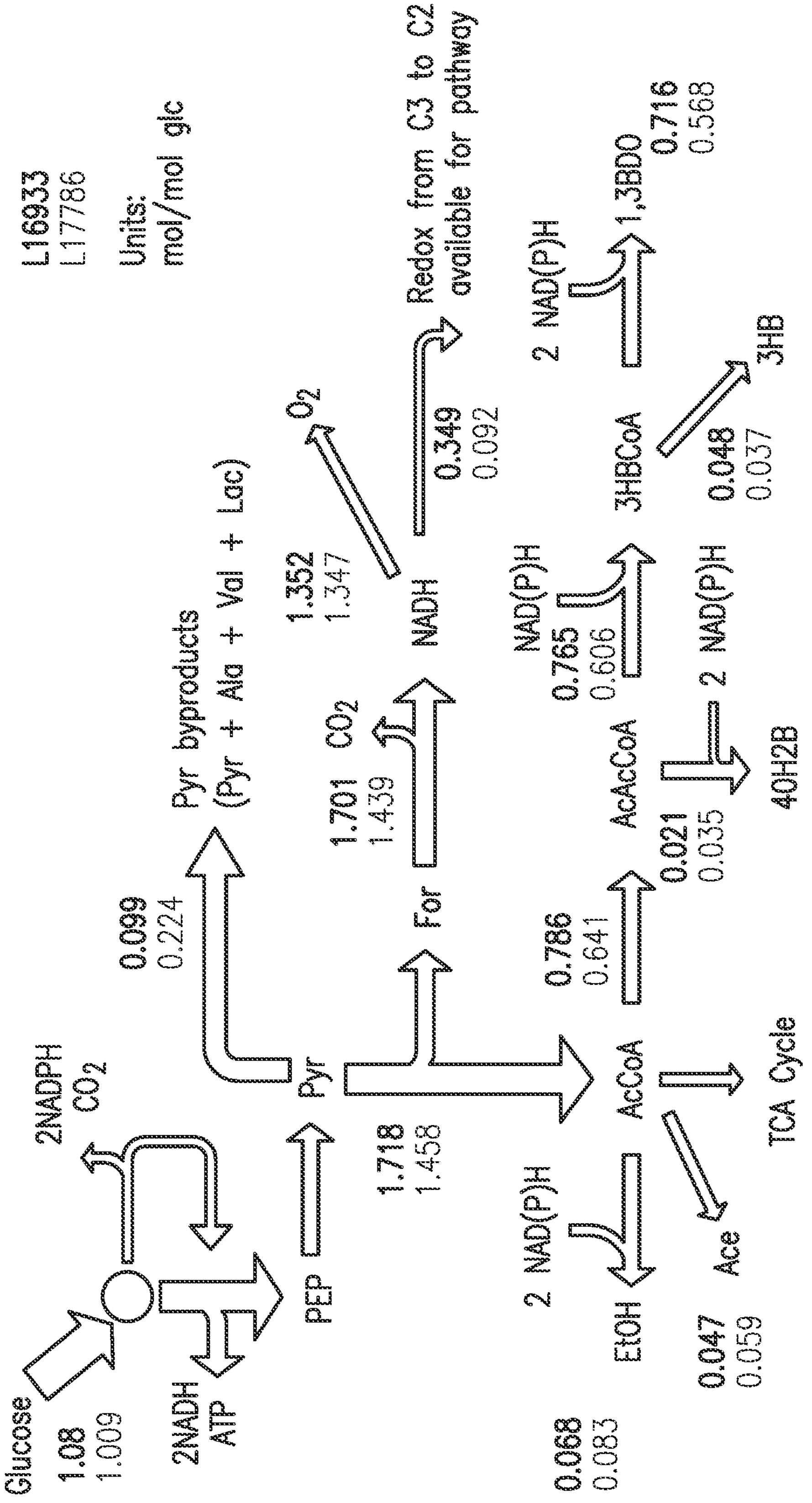
FIG. 13 shows flux modeling for the L17786 (nadK variant) strain compared to the L16933 (nadK and pntAB) strain under high aeration conditions. Phosphoenolpyruvate (PEP), pyruvate (Pyr), formate (For), ethanol (EtOH), acetate (Ace), acetyl coenzyme A (AcCoA), tricarboxylic acid cycle (TCA) cycle, acetoacetyl coenzyme A (AcAcCoA), 4-hydroxy-2-butanone (4OH2B), 3-hydroxybutyryl coenzyme A (3HB-CoA), 3-hydroxybutyrate (3HB), 1,3-butanediol (1,3-BDO), alanine (Ala), valine (Val), lactate (Lac).

Flux modeling of the L17786 strain compared to the L16933 strain under high aeration conditions was performed. Analysis of the overall flux revealed that there was a significant reduction in pyruvate being shuttled towards pyruvate byproducts, mainly alanine and pyruvate (FIG. 13). In addition, there was a decrease in C2 byproducts for the L17786 strain compared to the L16933 strain (FIG. 13). For example, acetate and ethanol were both lower in the L17786 strain compared to the L16933 strain (FIG. 13).

Figure 14:
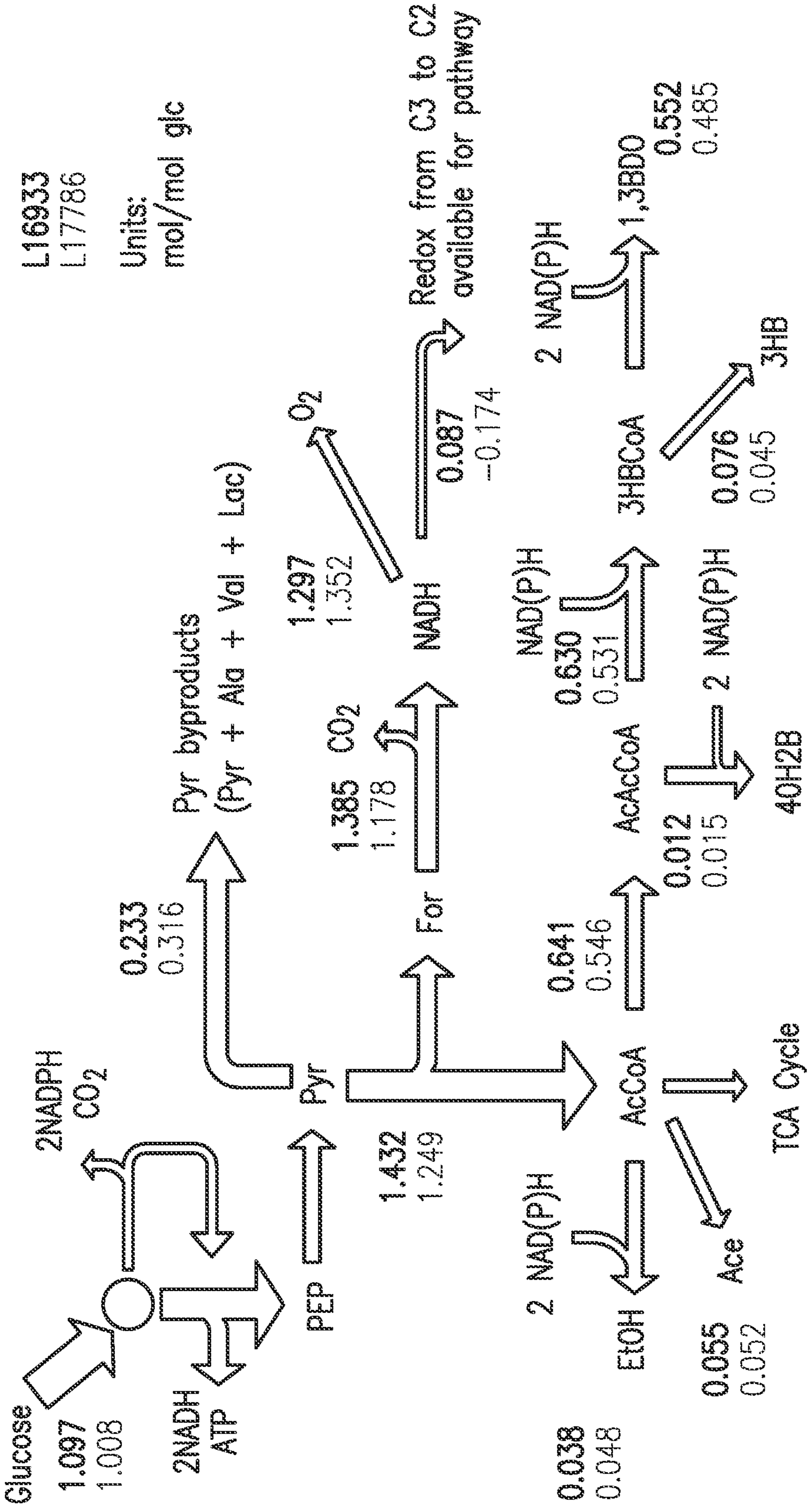
FIG. 14 shows flux modeling for the L17786 (nadK variant) strain compared to the L16933 (nadK and pntAB) strain under high aeration conditions between 0-12 hours. Phosphoenolpyruvate (PEP), pyruvate (Pyr), formate (For), ethanol (EtOH), acetate (Ace), acetyl coenzyme A (AcCoA), tricarboxylic acid cycle (TCA) cycle, acetoacetyl coenzyme A (AcAcCoA), 4-hydroxy-2-butanone (4OH2B), 3-hydroxybutyryl coenzyme A (3HB-CoA), 3-hydroxybutyrate (3HB), 1,3-butanediol (1,3-BDO), alanine (Ala), valine (Val), lactate (Lac).

Measurement of the 1,3-BDO pathway flux was increased approximately 25% (FIG. 13). However, similar levels of the C4 byproducts 4-hydroxy-2-butanone (4OH2B) and 3-hydroxybutyrate (3HB) were observed (FIG. 13). Importantly, there was a significant increase (3.7 fold) in redox available for pathway from C3 to C2 (i.e., pyruvate to acetyl-CoA, acetate and ethanol). Subsequently, the flux modeling of the L17786 strain compared to the L16933 strain under high aeration conditions was further analyzed according to the first 12 hours of fermentation, and between 12 hours to the end. Analysis of the overall flux during the first 12 hours revealed that less pyruvate (26%) is directed towards byproducts for the L17786 strain. In addition, a decrease (8%) in C2 byproducts (acetate and ethanol) was observed for the L17786 strain. Consistent with the results from the total flux modeling, during the first 12 hours there was an increase (14%) in the 1,3-BDO pathway flux for the L17786 strain (FIG. 14). Notably, there was a significant increase (68%) in 3-hydroxybutyrate (3HB), along with higher NAD(P)H levels and NAD(P)H/NAD(P) ratios for the L17786 strain (FIG. 14). These results further indicated that there was a redox limitation for pathway from C3 to C2 for the L16933 strain.

Figure 15:
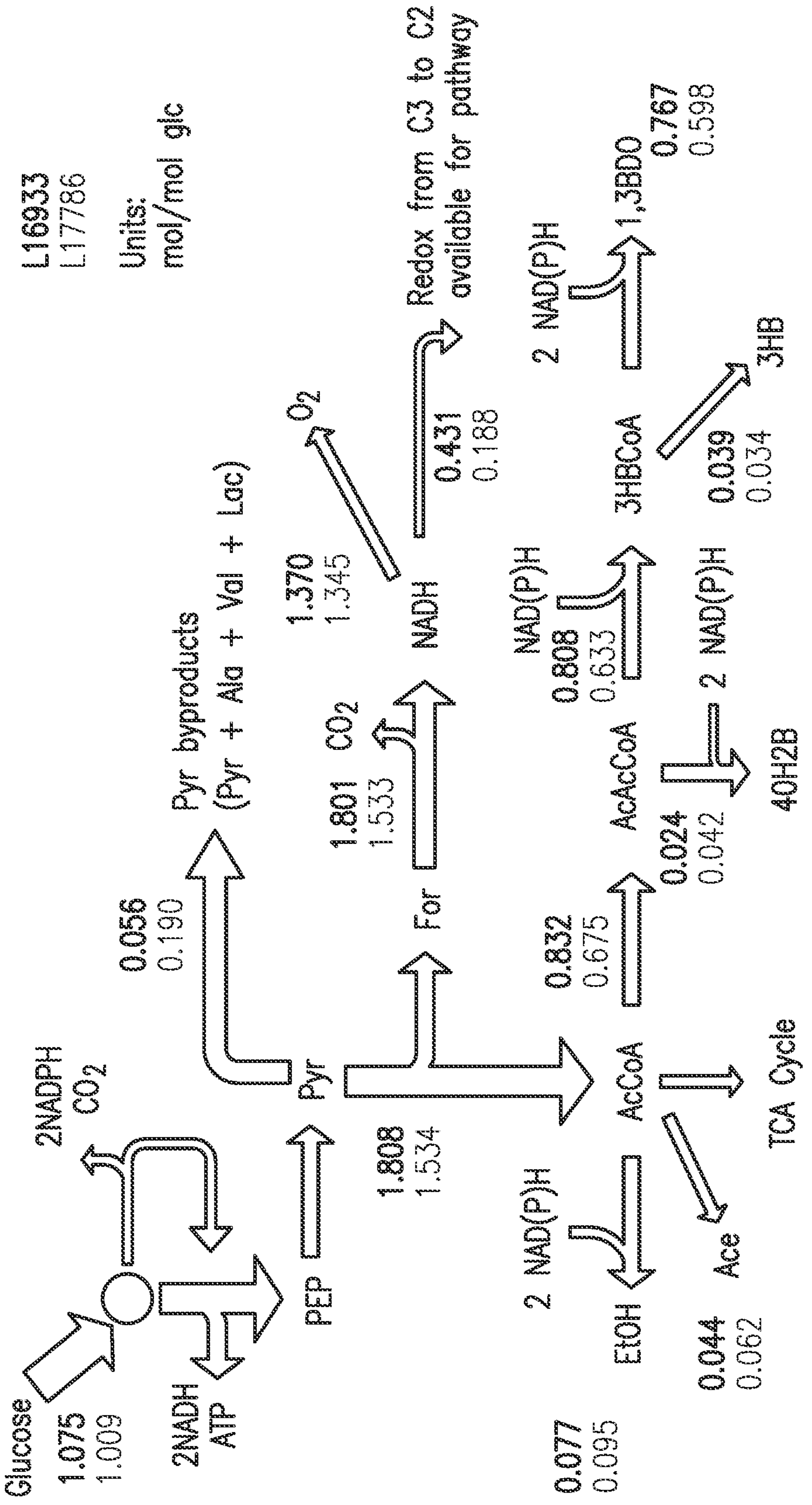
FIG. 15 shows flux modeling for the L17786 (nadK variant) strain compared to the L16933 (nadK and pntAB) strain under high aeration conditions between 12 hours to end of fermentation. Phosphoenolpyruvate (PEP), pyruvate (Pyr), formate (For), ethanol (EtOH), acetate (Ace), acetyl coenzyme A (AcCoA), tricarboxylic acid cycle (TCA) cycle, acetoacetyl coenzyme A (AcAcCoA), 4-hydroxy-2-butanone (4OH2B), 3-hydroxybutyryl coenzyme A (3HB-CoA), 3-hydroxybutyrate (3HB), 1,3-butanediol (1,3-BDO), alanine (Ala), valine (Val), lactate (Lac).

Analysis of the overall flux from twelve hours to the end indicated that there was less pyruvate (70%) directed towards byproducts for the for the L17786 strain (FIG. 15). In addition, there was a decrease (30%) in C2 byproducts (acetate and ethanol) for the L17786 strain (FIG. 15). Measurement of the pathway flux revealed that there was an increase (18%) in the 1,3-BDO pathway flux, and a decrease (40%) in C4 byproducts for the L17786 strain (FIG. 15). A significant increase (2.3-fold) in redox available for pathway from C3 to C2 was also observed for the L17786 strain (FIG. 15).

In summary, these results indicated that higher redox levels, as well as redox ratios, led to better 1,3-BDO titrate, rate, and yield for the L17786 strain. Collectively, this revealed that the L17786 strain is more robust under higher aeration conditions.

Example VI gapA vs. gapN

Figure 16:
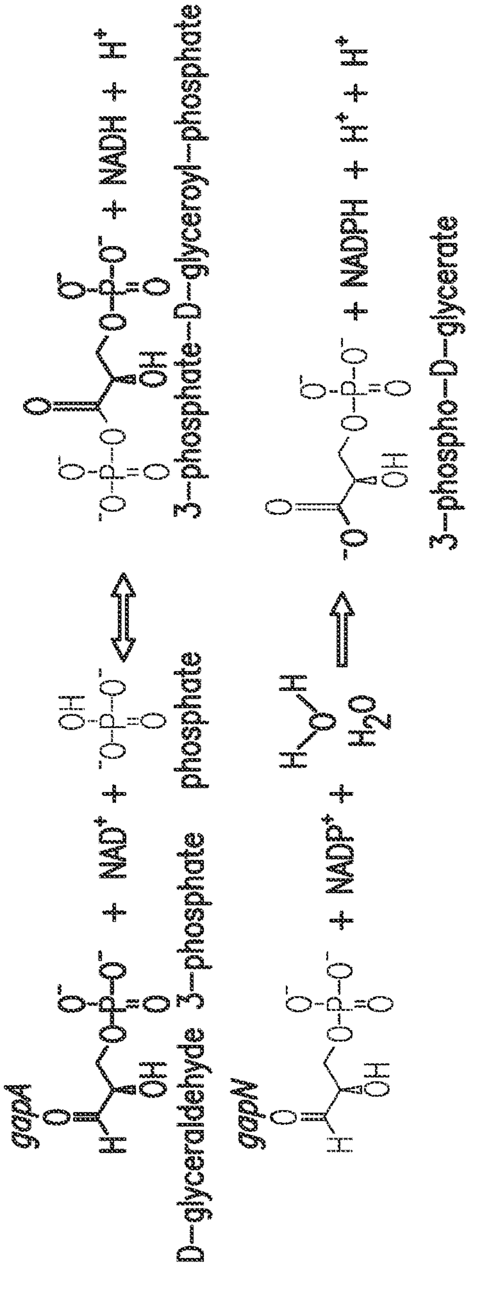
FIG. 16 shows exemplary reactions for the NADH generation gapA and NADPH generating gapN enzymes.

The redox balance analysis of endogenous glyceraldehyde-3-phosphate dehydrogenase A (gapA) was compared to NAD(P)-dependent glyceraldehyde-3-phosphate dehydrogenase (gapN). gapA is an enzyme native to *E. coli* that couples glycolysis flux to NADH generation, where 1 $CO_2$ is generated per redox generation via pyruvate/formate dehydrogenase, tricarboxylic acid (TCA) cycle, or pentose phosphate (PP) pathway (FIG. 16). In contrast, exogenous gapN couples NADPH generation to glycolysis flux. Unlike PP pathway and TCA cycle, no $CO_2$ is generated (FIG. 16). In addition, there is no membrane protein expression for NADPH generation.

In the examples provided above, generation of NADPH was demonstrated to improve the production of 1,3-BDO. To determine if gapN's ability to increase NADPH generation was able to increase 1,3-BDO yield, a parental strain expressing wild-type pntAB was compared to a gapN expressing strain in the absence of pntAB. The results indicated that gapN activity is advantageous over wild-type pntAB activity for 1,3,-BDO yield of higher 0.8 mol/mol. Importantly, without pntAB, gapN activity was found to be proportion to 1,3-BDO.

Furthermore, the 1,3-BDO instantaneous yield was increased during microaerobic growth and was maintained during production phase.

Figure 18:
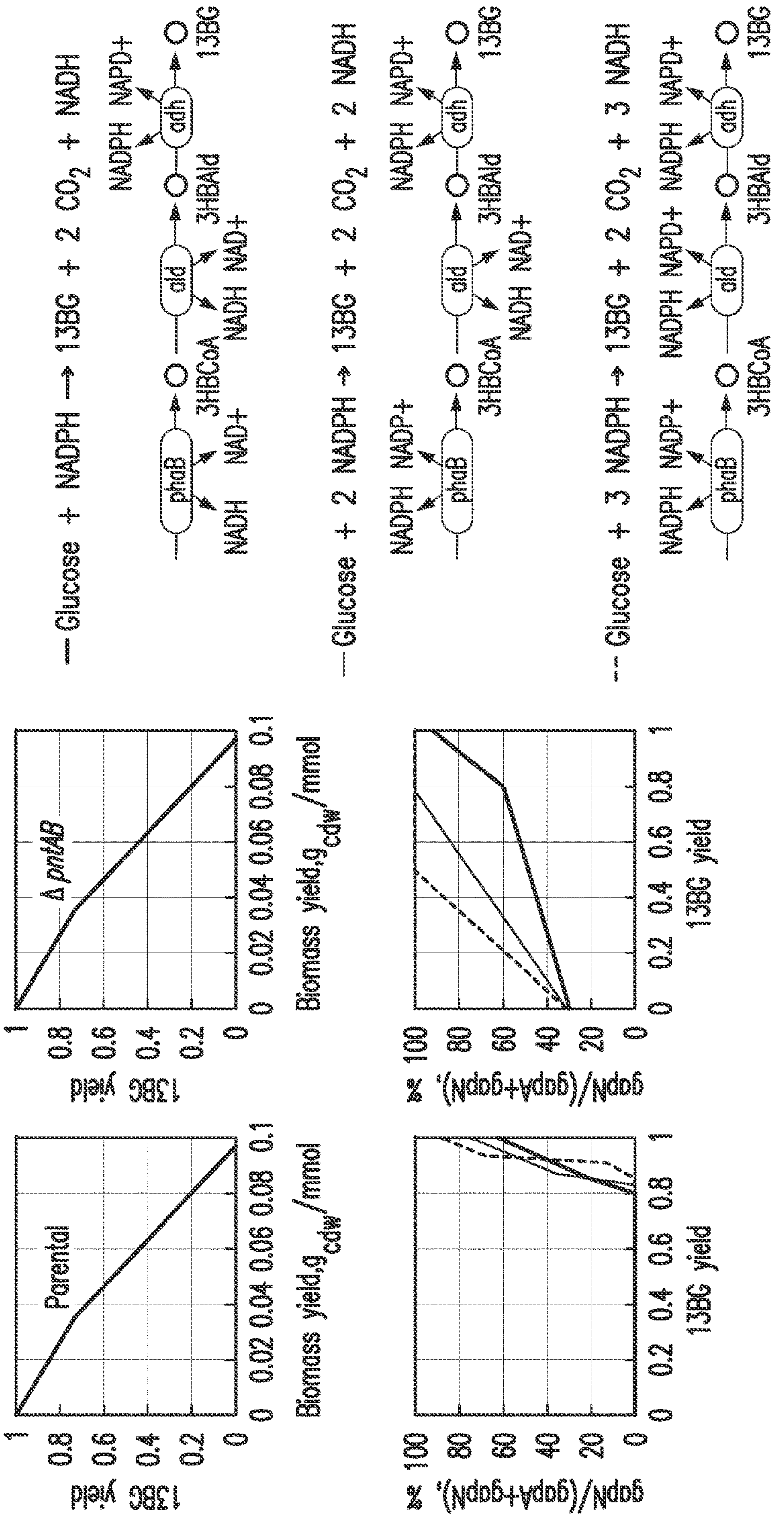
FIG. 18 shows three exemplary NADPH dependent reactions with increasing demand for NADPH. The results show that gapN activity is more beneficial with reactions that require greater NADPH demand.
Figure 19A:
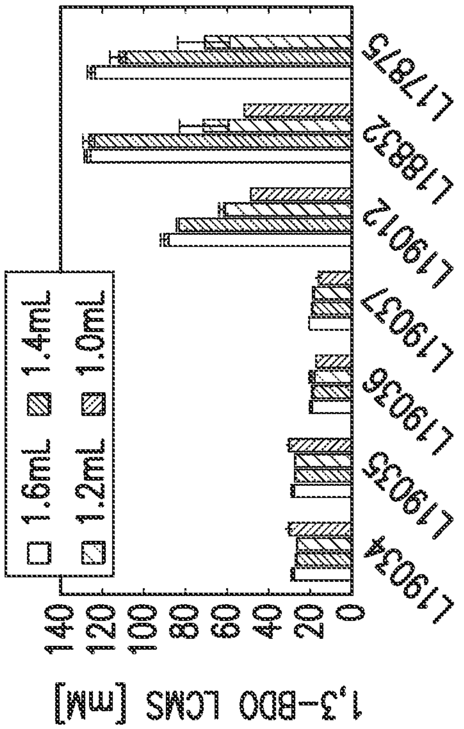
FIG. 19A-FIG. 19D show the titer (FIG. 19A), rate (FIG. 19B), yield (FIG. 19C), and specific rate (FIG. 19D) of 1,3-butanediol (1,3-BDO) production for gapN strains relative to controls. The results demonstrate that gapN strains provide NADPH for 1,3-BDO production.
Figure 19B:
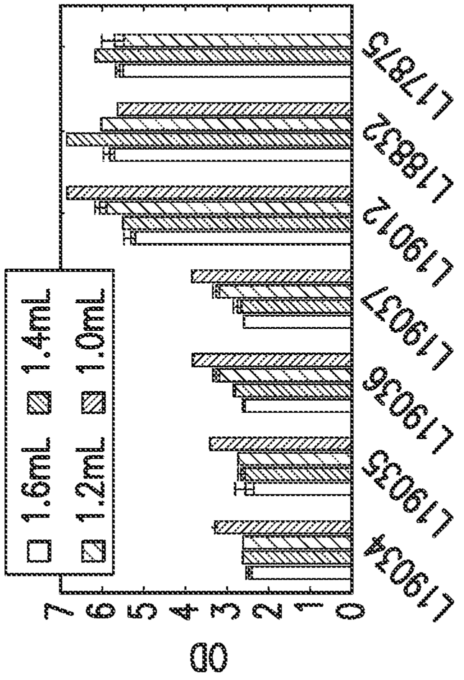
Figure 19C:
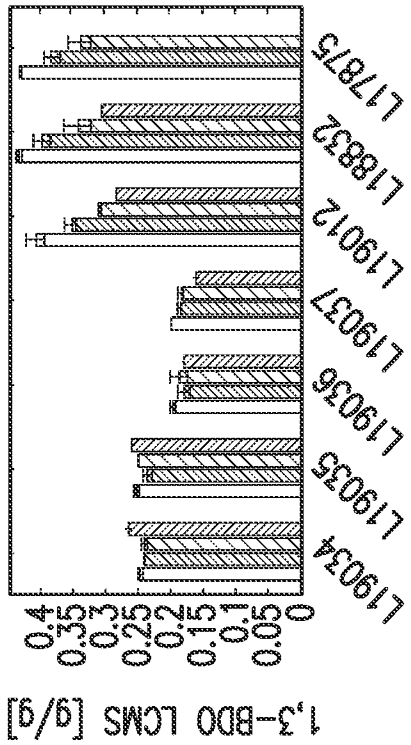
Figure 19D:
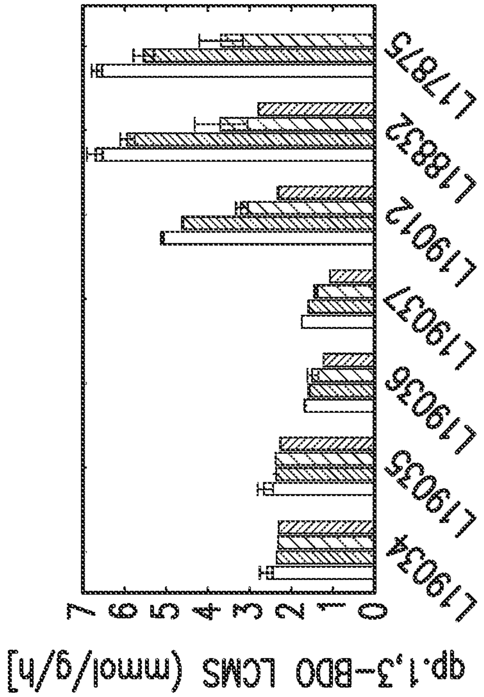

The parental strain expressing wild-type pntAB was then compared to the gapN expressing strain in the absence of pntAB under three different pathways each with an increasing demand for NADPH. In the first pathway, only one NADPH molecule was required when a NADH dependent phaB (phaB 1500AL) was combined with an NADH dependent aldehyde deydrogenases (ald), and an NADPH dependent alcohol dehydrogenase (adh) to convert glucose into 1,3-BDO. In the second pathway, two NADPH molecule were required when a NADPH dependent phaB (phaB 1500GM) was combined with an NADH dependent ald and an NADPH dependent adh to convert glucose into 1,3-BDO. In the third pathway, three NADPH molecule were required when a NADPH dependent phaB (phaB 1500GM) was combined with an NADPH dependent ald and an NADPH dependent adh to convert glucose into 1,3-BDO. With each pathway that required increasing NADPH demand, gapN activity was more beneficial (FIG. 18).

In summary, gapN offered an opportunity to couple glycolysis flux to NADPH generation without losing $CO_2$ or relying on pntAB and nadK. In addition, it was observed that the relative activity of gapN to gapA was increased from microaerobic growth to production phase. Furthermore, in strains where pntAB was deleted, the relative activity of gapN over gapA was proportional to 1,3-BDO yield.

Example VII

Evaluation of gapN Strains

Next, gapN strains were evaluated for their ability to produce 1,3-BDO. Seven different strains with varying modifications were compared and evaluated (Table 6).

TABLE 6

| Strain | Background |
|---|---|
| L19034 | ΔgapA::P119-cds_10662A (BMP) |
| L19035 | ΔgapA::P119-cds_10663A (BMM) |
| L19036 | ΔnadK variant, WTpntAB<br>ΔgapA::P119-cds_10662A |
| L19037 | ΔnadK variant, WTpntAB<br>ΔgapA::P119-cds_10663A |
| L19012 | ΔnadK variant, WTpntAB |
| L18832 | Control strain |
| L17875 | 2017 q2 strain plate control |

The strains were grown for 24 hours at a constant agitation of 400 rpm, under 100% air (300 standard cubic centimeter per minute; sccm) in a plexibox. SSM5 2% glucose flask preculture, and SSM5 4% glucose 48WP mainculture. The initial optical density (OD) was 0.4, and fill volumes included 1.6 mL, 1.4 mL, 1.2 mL, and 1.0 mL with technical duplicates.

Measurement of the titrate, rate, and yield of 1,3-BDO in the gapN strains L19034, L19035, L19036, and L19037 revealed that the gapN strains produced 1,3-BDO (FIG. 19A-FIG. 19D). This demonstrated the ability of gapN strains to provide NADPH for 1,3-BDO production. However, it was also observed that the titer was lower for the gapN strains. Since the complete deletion of gapA is expected to decrease NADH production, these results indicated tuning gapA to gapN expression rather than complete deletion would be beneficial.

Example VIII

GapN and GapA Expression Tuning

The expression of gapA and gapN can be modified in order to increase redox availability. In order to increase the production of NADPH, without decreasing the production of NADH, gapN levels can be overexpressed in a strain that expresses endogenous gapA. The gapN levels can be overexpressed such that they are higher than the gapA levels. As a result, both gapA and gapN will be expressed, but exogenous gapN will expressed at a higher level.

Figure 17:
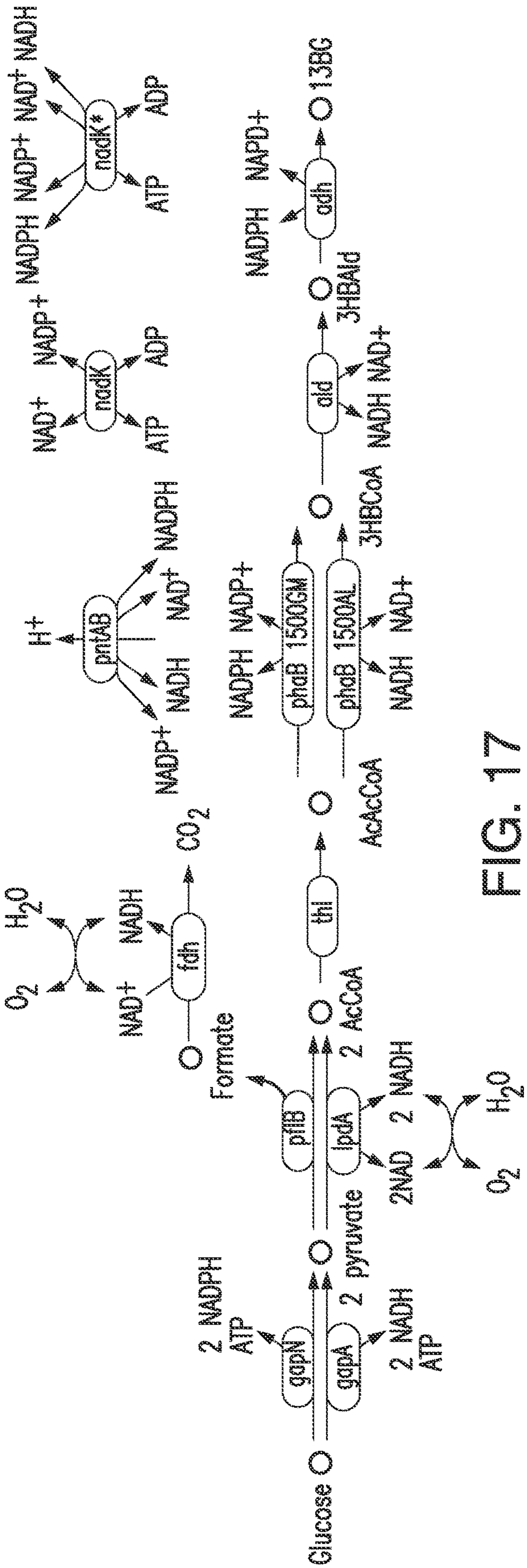
FIG. 17 shows an exemplary pathway for generating 1,3-BDO from glucose optionally using (i) either the NADH generation gapA or the NADPH generating gapN enzymes, (ii) nadK and pntAB or the nadK variant, and (iii) NADH dependent phaB (phaB 1500AL) or NADPH dependent phaB (phaB 1500GM). NAD(P)-dependent glyceraldehyde-3-phosphate dehydrogenase (gapN), glyceraldehyde-3-phosphate dehydrogenase A (gapA), formate acetyltransferase (pflB), dihydrolipoyl dehydrogenase (lpdA), thiolase (thl), acetoacetyl-CoA reductase (phaB), aldehyde dehydrogenases (ald), alcohol dehydrogenase (adh), 1,3-butanediol (1,3-BG), formate dehydrogenase (fdh), NAD(P) transhydrogenase subunit alpha part 2 (pntAB), NAD kinase (nadK), and ATP-NADH kinase (nadK*).

To increase the redox availability further, strain construction can be performed using an NADPH dependent phaB (phaB 1500GM) or an NADH dependent phaB (phaB 1500AL) (FIG. 17). In addition, redox availability can be increased even further stain construction can be performed using a nadK variant that allows direct conversion of NADH into NADPH (FIG. 17).

The collective effect of the increase in NADPH availability can facilitate the conversion of 3-hydroxybutyraldehyde (3HB-Ald) to 1,3-BDO and result in an increase in 1,3-BDO production. Similarly, maintaining endogenous gapA levels can facilitate the production of NADH and thereby enable 3HB-CoA conversion to 3HB-Ald. Taken together, this demonstrates that GapN and GapA expression tuning can enable an increase in redox availability. This increase in redox cofactor availability can increase the production of 1,3-BDO.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A non-naturally occurring microbial organism having an increased availability of reduced nicotinamide adenine dinucleotide phosphate (NADPH), comprising (a) two exogenous nucleic acids encoding an NAD(P) transhydrogenase subunit alpha part 2 and an ATP NAD+ kinase expressed in an amount to increase availability of NADPH as compared to the microbial organism without the two exogenous nucleic acids, and (b) a gene attenuation occurring in a gene encoding a non-proton-translocating NADH dehydrogenase II that results in an increased ratio of NADPH to NADH present in the cytosol of said non-naturally occurring microbial organism following said attenuation, as compared to the microbial organism without (a) and (b).

2. The non-naturally occurring microbial organism of claim 1, further comprising an exogenous nucleic acid encoding: (a) an ATP-NADH kinase; or (b) a NADP-dependent glyceraldehyde-3-phosphate dehydrogenase.

3. The non-naturally occurring microbial organism of claim 1, further comprising an exogenous nucleic acid encoding an ATP-NADH kinase and a NADP-dependent glyceraldehyde-3-phosphate dehydrogenase.

4. The non-naturally occurring microbial organism of claim 1, wherein said microbial organism comprises three exogenous nucleic acids, wherein optionally said three exogenous nucleic acids encode: (a) an ATP-NADH kinase, a NAD (P) transhydrogenase subunit alpha part 2 and an ATP NAD+ kinase and an ATP NAD+ kinase; or (b) a NADP-dependent glyceraldehyde-3-phosphate dehydrogenase, a NAD (P) transhydrogenase subunit alpha part 2 and an ATP NAD+ kinase.

5. The non-naturally occurring microbial organism of claim 1, wherein said microbial organism comprises four exogenous nucleic acids, wherein optionally said four exogenous nucleic acids encode a NADP-dependent glyceraldehyde-3-phosphate dehydrogenase, an ATP-NADH kinase, a NAD (P) transhydrogenase subunit alpha part 2 and an ATP NAD+ kinase, and an ATP NAD+ kinase.

6. The non-naturally occurring microbial organism of claim 1, wherein said microbial organism comprises an exogenous nucleic acid encoding ATP-NADH kinase, and wherein said ATP-NADH kinase is a variant ATP-NAD+ kinase.

7. The non-naturally occurring microbial organism of claim 1, wherein:

(i) said exogenous nucleic acids are regulated by a promoter selected from the group consisting of an endogenous promoter, a constitutive promoter, and an inducible promoter;

(ii) said microbial organism is a species of bacteria, yeast, or fungus; or (iii) said non-naturally occurring microbial organism is in a substantially anaerobic culture medium.

8. The non-naturally occurring microbial organism of claim 1, wherein said microbial organism further comprises an exogenous nucleic acid encoding a NADP-dependent glyceraldehyde-3-phosphate dehydrogenase, and wherein said NADP-dependent glyceraldehyde-3-phosphate dehydrogenase: (a) is expressed at a higher level than an endogenous glyceraldehyde-3-phosphate dehydrogenase A, and optionally a ratio of said NADP-dependent glyceraldehyde-3-phosphate dehydrogenase to an endogenous glyceraldehyde-3-phosphate dehydrogenase A plus said NADP-dependent glyceraldehyde-3-phosphate dehydrogenase is at least about 10% to about 90%; (b) increases production of NADPH; (c) is from a methanotrophic bacteria; or (d) is from *Bacillus methanolicus*.

9. The non-naturally occurring microbial organism of claim 8, wherein endogenous glyceraldehyde-3-phosphate dehydrogenase A comprises an attenuated glyceraldehyde-3-phosphate dehydrogenase A, and wherein optionally said attenuated glyceraldehyde-3-phosphate dehydrogenase A comprises reduced expression of glyceraldehyde-3-phosphate dehydrogenase A.

10. The non-naturally occurring microbial organism of claim 1, wherein said gene attenuation in the gene encoding non-proton-translocating NADH dehydrogenase II comprises a deletion of non-proton-translocating NADH dehydrogenase II and/or a decrease in NADPH consumption as compared to the microbial organism without said attenuation.

11. The non-naturally occurring microbial organism of claim 1, further comprising a 1,3-butanediol (1,3-BDO) pathway, a methyl methacrylate (MMA) pathway, a (3R)-hydroxybutyl (3R)-hydroxybutyrate pathway, an amino acid production pathway, a 3-hydroxybutyryl-coenzyme A (3HB-CoA) pathway, an adipate pathway, a caprolactam pathway, a 6-aminocaproic acid (6-ACA) pathway, a hexamethеylenediamine (HMDA) pathway, or a methacrylic acid (MAA) pathway.

12. The non-naturally occurring microbial organism of claim 11, wherein said microbial organism comprises an 1,3-BDO pathway, wherein optionally said 1,3-BDO pathway comprises an acetoacetyl-CoA reductase (CoA-dependent, aldehyde forming); a 3-oxobutyraldehyde reductase (ketone reducing); a 3-hydroxybutyraldehyde reductase; an acetoacetyl-CoA reductase (CoA-dependent, alcohol forming); a 3-oxobutyraldehyde reductase (aldehyde reducing); a 4-hydroxy, 2-butanone reductase; an acetoacetyl-CoA reductase (ketone reducing); a 3-hydroxybutyryl-CoA reductase (aldehyde forming); and a 3-hydroxybutyryl-CoA reductase (alcohol forming).

13. The non-naturally occurring microbial organism of claim 11, wherein said microbial organism comprises an (3R)-hydroxybutyl (3R)-hydroxybutyrate pathway, wherein optionally said (3R)-hydroxybutyl (3R)-hydroxybutyrate pathway comprises a (3R)-hydroxybutyl (3R)-hydroxybutyrate ester forming enzyme; a (3R)-hydroxybutyryl-CoA: (R)-1,3-butanediol alcohol transferase; a (3R) hydroxybutyl 3-oxobutyrate ester forming enzyme; an acetoacetyl-CoA: (R)-1,3-butanediol alcohol transferase; a (3R)-hydroxybutyl 3-oxobutyrate reductase; a (3R)-hydroxybutyryl-ACP: (R)-1,3-butanediol ester synthase, and an acetoacetyl-ACP: (R)-1,3-butanediol ester synthase.

14. The non-naturally occurring microbial organism of claim 11, wherein said microbial organism comprises an 1,3-BDO pathway or an (3R)-hydroxybutyl (3R)-hydroxybutyrate pathway, and wherein said microbial organism comprises a nucleic acid encoding an acetoacetyl-CoA reductase.

15. The non-naturally occurring microbial organism of claim 14, wherein said acetoacetyl-CoA reductase is a mutant acetoacetyl-CoA reductase, and wherein optionally said mutant acetoacetyl-CoA reductase uses NADH as a substrate.

16. The non-naturally occurring microbial organism of claim 11, wherein said microbial organism comprises a 3HB-CoA pathway, wherein optionally said 3HB-CoA pathway comprises an acetyl-CoA thiolase, and a 3-hydroxybutyryl-CoA dehydrogenase.

17. The non-naturally occurring microbial organism of claim 11, wherein said microbial organism comprises a first MMA pathway and optionally a second MMA pathway, wherein said first MMA pathway optionally comprises:

(a) a 4-hydroxybutyryl-CoA dehydratase, a crotonase, a 2-hydroxyisobutyryl-CoA mutase, a 2-hydroxyisobutyryl-CoA dehydratase, and a methacrylic acid (MAA)-CoA: methanol transferase; or (b) a 4-hydroxybutyryl-CoA dehydratase, a crotonase, a 2-hydroxyisobutyryl-CoA mutase, a 3-hydroxyisobutyryl-CoA: methanol transferase, and a methyl-2-hydroxyisobutyrate dehydratase, and wherein said second MMA pathway optionally comprises:

(i) a methacrylic acid (MAA)-CoA: methanol transferase, a 4-hydroxybutyryl-CoA mutase, and a 3-hydroxyisobutyryl-CoA dehydratase; or (ii) a 4-hydroxybutyryl-CoA mutase, a 3-hydroxyisobutyryl-CoA: methanol transferase, and a methyl-3-hydroxyisobutyrate dehydratase.

18. The non-naturally occurring microbial organism of claim 11, wherein said microbial organism comprises an amino acid production pathway, wherein optionally said amino acid production pathway comprises a tryptophan production pathway, a threonine production pathway, a lysine production pathway, or a glutamate production pathway.

19. The non-naturally occurring microbial organism of claim 11, wherein said microbial organism comprises a 6-ACA pathway, wherein optionally said 6-ACA pathway comprises a 2-amino-7-oxosubarate keto-acid decarboxylase, a 2-amino-7-oxoheptanoate decarboxylase, a 2-amino-7-oxoheptanoate oxidoreductase, a 2-aminopimelate decarboxylase, a 6-aminohexanal oxidoreductase, a 2-amino-7-oxoheptanoate decarboxylase, or a 2-amino-7-oxosubarate amino acid decarboxylase.

20. The non-naturally occurring microbial organism of claim 11, wherein said microbial organism comprises a caprolactam pathway, wherein optionally said caprolactam pathway comprises a 3-oxoadipyl-CoA thiolase, a 3-oxoadipyl-CoA reductase, a 3-hydroxyadipyl-CoA dehydratase, a 5-carboxy-2-pentenoyl-CoA reductase, an adipyl-CoA reductase (aldehyde forming), a 6-aminocaproate transaminase, a 6-aminocaproate dehydrogenase, a 6-aminocaproyl-CoA/acyl-CoA transferase, and a 6-aminocaproyl-CoA synthase.

21. The non-naturally occurring microbial organism of claim 11, wherein said microbial organism comprises an adipate pathway, wherein optionally said adipate pathway comprises a 3-oxoadipyl-CoA thiolase, a 3-oxoadipyl-CoA reductase, a 3-hydroxyadipyl-CoA dehydratase, a 5-carboxy-2-pentenoyl-CoA reductase, an adipyl-CoA hydrolase, an adipyl-CoA ligase, an adipyl-CoA transferase and a phosphotransadipylase/adipate kinase.

22. The non-naturally occurring microbial organism of claim 11, wherein said microbial organism comprises a hexamethylenediamine (HMDA) pathway, wherein optionally said HMDA pathway comprise a 3-oxoadipyl-CoA thiolase, a 3-oxoadipyl-CoA reductase, a 3-hydroxyadipyl-CoA dehydratase, a 5-carboxy-2-pentenoyl-CoA reductase, an adipyl-CoA reductase (aldehyde forming), a 6-aminocaproate transaminase, a 6-aminocaproate dehydrogenase, a 6-aminocaproyl-CoA/acyl-CoA transferase, a 6-aminocaproyl-CoA synthase, a 6-aminocaproyl-CoA reductase (aldehyde forming), a HMDA transaminase, and a HMDA dehydrogenase.

23. The non-naturally occurring microbial organism of claim 11, wherein said microbial organism comprises a MAA pathway, wherein optionally said MAA pathway comprises:

(a) (i) a succinyl-CoA transferase, ligase, or synthetase;
 (ii) a methylmalonyl-CoA mutase;
 (iii) a methylmalonyl-CoA epimerase;
 (iv) a methylmalonyl-CoA reductase (aldehyde forming);
 (v) a methylmalonate semialdehyde reductase; and
 (vi) a 3-hydroxyisobutyrate dehydratase;

(b) (i) a succinyl-CoA transferase, ligase, or synthetase;
 (ii) a methylmalonyl-CoA mutase;
 (iii) a methylmalonyl-CoA reductase (aldehyde forming);
 (iv) a methylmalonate semialdehyde reductase; and
 (v) a 3-hydroxyisobutyrate dehydratase; or (c) (i) a succinyl-CoA transferase, ligase, or synthetase;
 (ii) a methylmalonyl-CoA mutase;
 (iii) a methylmalonyl-CoA reductase (alcohol forming); and
 (iv) a 3-hydroxyisobutyrate dehydratase.

24. A method for increasing the availability of NADPH in a non-naturally occurring microbial organism, comprising culturing the non-naturally occurring microbial organism of claim 1, under conditions and for a sufficient period of time to increase the availability of NADPH.

25. The method of claim 24, wherein increasing the availability of NADPH yields an increase in one or more compounds selected from the group consisting of 1,3-BDO, MMA, (3R)-hydroxybutyl (3R)-hydroxybutyrate, amino acids, 3HB-CoA, adipate, caprolactam, 6-ACA, HMDA, and MAA.

* * * * *